(12) United States Patent
Darisse et al.

(10) Patent No.: US 9,649,163 B2
(45) Date of Patent: May 16, 2017

(54) INTRODUCTION DEVICES FOR HIGHLY ARTICULATED ROBOTIC PROBES AND METHODS OF PRODUCTION AND USE OF SUCH PROBES

(75) Inventors: Ian J. Darisse, Allston, MA (US); Arnold E. Oyola, Northborough, MA (US); Joseph A. Stand, Holden, MA (US); Robert A. DiDomenico, Norfolk, MA (US); Samuel F. Straface, Duxbury, MA (US); J. Christopher Flaherty, Auburndale, FL (US)

(73) Assignee: Medrobotics Corporation, Raynham, MA (US)

( * ) Notice: Subject to any disclaimer, the term of this patent is extended or adjusted under 35 U.S.C. 154(b) by 0 days.

(21) Appl. No.: 13/884,407

(22) PCT Filed: Nov. 10, 2011

(86) PCT No.: PCT/US2011/060214
§ 371 (c)(1),
(2), (4) Date: Sep. 19, 2013

(87) PCT Pub. No.: WO2012/078309
PCT Pub. Date: Jun. 14, 2012

(65) Prior Publication Data
US 2014/0012288 A1    Jan. 9, 2014

Related U.S. Application Data

(60) Provisional application No. 61/412,733, filed on Nov. 11, 2010, provisional application No. 61/472,344, (Continued)

(51) Int. Cl.
A61B 1/04    (2006.01)
A61B 19/00    (2006.01)
(Continued)

(52) U.S. Cl.
CPC ........ *A61B 19/2203* (2013.01); *A61B 1/0011* (2013.01); *A61B 1/0016* (2013.01);
(Continued)

(58) Field of Classification Search
USPC .......................... 600/114, 121–125, 139–142
See application file for complete search history.

(56) References Cited

U.S. PATENT DOCUMENTS 3,060,972 A    10/1962    Sheldon
3,557,780 A    1/1971    Sato
(Continued)

FOREIGN PATENT DOCUMENTS

EP    653922    11/2005
EP    1015068    9/2011
(Continued)

OTHER PUBLICATIONS

Reynolds, O., "On Efficiency of Belts or Straps as Communicators of Work", The Engineer, 1874, p. 396.
(Continued)

*Primary Examiner* — Matthew J Kasztejna
(74) *Attorney, Agent, or Firm* — Onello & Mello, LLP

(57) ABSTRACT

In an introduction assembly for an articulated probe, a feeding mechanism has actuators for controlling the articulated probe. The introduction device is fixed in a positional relationship to the feeding mechanism. The introduction device includes a support member configured to support an articulated probe. A proximal end of the support member has an entrance configured to guide the articulated probe into contact with the support member. A distal end of the support member has an exit configured to guide the articulated probe from the support member into a region of interest.

28 Claims, 34 Drawing Sheets

Related U.S. Application Data filed on Apr. 6, 2011, provisional application No. 61/492,578, filed on Jun. 2, 2011, provisional application No. 61/534,032, filed on Sep. 13, 2011.

(51) Int. Cl.
*A61B 1/00* (2006.01)
*A61B 1/005* (2006.01)
*A61B 17/00* (2006.01)
*A61B 17/34* (2006.01)
*A61B 34/00* (2016.01)
*A61B 90/00* (2016.01)
*A61B 34/30* (2016.01)

(52) U.S. Cl.
CPC ........ *A61B 1/0055* (2013.01); *A61B 1/00154* (2013.01); *A61B 34/30* (2016.02); *A61B 34/76* (2016.02); *A61B 1/0053* (2013.01); *A61B 1/0057* (2013.01); *A61B 2017/00314* (2013.01); *A61B 2017/3445* (2013.01); *A61B 2034/301* (2016.02); *A61B 2034/715* (2016.02); *A61B 2034/742* (2016.02); *A61B 2090/064* (2016.02); *A61B 2090/3614* (2016.02)

(56) References Cited

U.S. PATENT DOCUMENTS

| | | |
|---|---|---|
| 3,572,325 A | 3/1971 | Bazell et al. |
| 3,583,393 A | 6/1971 | Takahashi |
| 3,625,200 A | 12/1971 | Muller |
| 3,638,973 A | 2/1972 | Poletti |
| 3,643,653 A | 2/1972 | Takahashi et al. |
| 3,703,968 A | 11/1972 | Uhrich et al. |
| 3,739,770 A | 6/1973 | Mori |
| 3,790,002 A | 2/1974 | Germond et al. |
| 3,892,228 A | 7/1975 | Mitsui |
| 3,920,972 A | 11/1975 | Corwin, Jr. et al. |
| 4,078,670 A | 3/1978 | Francois et al. |
| 4,108,211 A | 8/1978 | Tanaka |
| 4,150,329 A | 4/1979 | Dahlstrom |
| 4,221,997 A | 9/1980 | Flemming |
| 4,259,876 A | 4/1981 | Belyanin et al. |
| 4,260,319 A | 4/1981 | Motoda et al. |
| 4,299,533 A | 11/1981 | Ohnaka |
| 4,351,323 A | 9/1982 | Ouchi et al. |
| 4,432,349 A | 2/1984 | Oshiro |
| 4,445,184 A | 4/1984 | Noguchi |
| 4,474,174 A | 10/1984 | Petruzzi |
| 4,475,375 A | 10/1984 | Hill |
| 4,479,914 A | 10/1984 | Baumrucker |
| 4,494,417 A | 1/1985 | Larson et al. |
| 4,496,278 A | 1/1985 | Kaise |
| 4,502,830 A | 3/1985 | Inaba et al. |
| 4,517,963 A | 5/1985 | Michel |
| 4,531,885 A | 7/1985 | Molaug |
| 4,535,207 A | 8/1985 | Lindqvist |
| 4,564,179 A | 1/1986 | Hollingsworth |
| 4,600,355 A | 7/1986 | Johnson |
| 4,655,257 A | 4/1987 | Iwashita |
| 4,661,032 A | 4/1987 | Arai |
| 4,666,366 A | 5/1987 | Davis |
| 4,700,693 A | 10/1987 | Lia et al. |
| 4,706,001 A | 11/1987 | Nakashima et al. |
| 4,726,355 A | 2/1988 | Okada |
| 4,780,045 A | 10/1988 | Akeel et al. |
| 4,787,369 A | 11/1988 | Allred, III et al. |
| 4,790,294 A | 12/1988 | Allred, III et al. |
| 4,796,607 A | 1/1989 | Allred, III et al. |
| 4,804,897 A | 2/1989 | Gordon et al. |
| 4,805,477 A | 2/1989 | Akeel |
| 4,806,066 A | 2/1989 | Rhodes et al. |
| 4,830,569 A | 5/1989 | Jannborg |
| 4,831,547 A | 5/1989 | Ishiguro et al. |
| 4,838,859 A | 6/1989 | Strassmann |
| 4,863,133 A | 9/1989 | Bonnell |
| 4,864,888 A | 9/1989 | Iwata |
| 4,873,965 A | 10/1989 | Danieli |
| 4,888,708 A | 12/1989 | Brantmark et al. |
| 4,900,218 A | 2/1990 | Sutherland |
| 4,941,457 A | 7/1990 | Hasegawa |
| 4,943,296 A | 7/1990 | Funakubo et al. |
| 4,947,827 A | 8/1990 | Opie et al. |
| 4,949,927 A | 8/1990 | Madocks et al. |
| 4,950,116 A | 8/1990 | Nishida |
| 4,956,790 A | 9/1990 | Tsuchihashi et al. |
| 4,979,949 A | 12/1990 | Matsen, III et al. |
| 4,984,563 A * | 1/1991 | Renaud .............. A61B 1/00082 600/106 |
| 4,998,916 A | 3/1991 | Hammerslag et al. |
| 5,005,558 A | 4/1991 | Aomori |
| 5,006,035 A | 4/1991 | Nakashima et al. |
| 5,012,169 A | 4/1991 | Ono et al. |
| 5,037,391 A | 8/1991 | Hammerslag et al. |
| 5,044,063 A | 9/1991 | Voellmer |
| 5,046,375 A | 9/1991 | Salisbury, Jr. et al. |
| 5,064,340 A | 11/1991 | Genov et al. |
| 5,078,140 A | 1/1992 | Kwoh |
| 5,086,401 A | 2/1992 | Glassman et al. |
| 5,105,819 A | 4/1992 | Wollschlager et al. |
| 5,108,368 A | 4/1992 | Hammerslag et al. |
| 5,127,393 A * | 7/1992 | McFarlin ........... A61B 1/00154 600/114 |
| 5,143,475 A | 9/1992 | Chikama |
| 5,167,221 A | 12/1992 | Chikama |
| 5,174,277 A | 12/1992 | Matsumaru |
| 5,176,126 A | 1/1993 | Chikama |
| 5,178,129 A | 1/1993 | Chikama et al. |
| 5,179,935 A | 1/1993 | Miyagi |
| 5,180,276 A | 1/1993 | Hendrickson |
| 5,193,963 A | 3/1993 | McAffee et al. |
| 5,195,968 A | 3/1993 | Lundquist et al. |
| 5,200,679 A | 4/1993 | Graham |
| 5,201,325 A | 4/1993 | McEwen et al. |
| 5,203,380 A | 4/1993 | Chikama |
| 5,203,772 A | 4/1993 | Hammerslag et al. |
| 5,217,003 A | 6/1993 | Wilk |
| 5,217,453 A | 6/1993 | Wilk |
| 5,236,432 A | 8/1993 | Matsen, III et al. |
| 5,251,611 A | 10/1993 | Zehel et al. |
| 5,254,088 A | 10/1993 | Lundquist et al. |
| 5,257,669 A | 11/1993 | Kerley et al. |
| 5,266,875 A | 11/1993 | Slotine et al. |
| 5,271,381 A | 12/1993 | Ailinger et al. |
| 5,297,443 A | 3/1994 | Wentz |
| 5,318,526 A | 6/1994 | Cohen |
| 5,327,905 A | 7/1994 | Avitall |
| 5,337,732 A | 8/1994 | Grundfest et al. |
| 5,386,741 A | 2/1995 | Rennex |
| 5,448,989 A | 9/1995 | Heckele |
| 5,512,034 A * | 4/1996 | Finn .................. A61B 1/00089 600/138 |
| 5,524,180 A | 6/1996 | Wang et al. |
| 5,681,262 A * | 10/1997 | Isse ........................ A61B 1/012 600/104 |
| 5,725,479 A * | 3/1998 | Knight .................. A61B 1/018 600/183 |
| 5,759,151 A | 6/1998 | Sturges |
| 5,815,640 A | 9/1998 | Wang et al. |
| 5,841,950 A | 11/1998 | Wang et al. |
| 5,907,664 A | 5/1999 | Wang et al. |
| 5,921,916 A | 7/1999 | Aeikens et al. |
| 6,032,673 A * | 3/2000 | Savage .............. A61B 18/1485 128/898 |
| 6,080,181 A | 6/2000 | Jensen et al. |
| 6,132,368 A | 10/2000 | Cooper |
| 6,223,100 B1 | 4/2001 | Green |
| 6,234,958 B1 * | 5/2001 | Snoke et al. ................. 600/114 |
| 6,328,730 B1 * | 12/2001 | Harkrider, Jr. ................. 604/523 |
| 6,346,072 B1 | 2/2002 | Cooper |
| 6,352,503 B1 * | 3/2002 | Matsui et al. ................. 600/104 |
| 6,440,061 B1 * | 8/2002 | Wenner et al. ................. 600/114 |

(56) References Cited

U.S. PATENT DOCUMENTS

| | | |
|---|---|---|
| 6,450,948 B1 | 9/2002 | Matsuura et al. |
| 6,458,076 B1 * | 10/2002 | Pruitt .......................... 600/146 |
| 6,743,239 B1 | 6/2004 | Kuehn et al. |
| 6,837,846 B2 | 1/2005 | Jaffe et al. |
| 6,837,847 B2 | 1/2005 | Ewers et al. |
| 6,916,306 B1 | 7/2005 | Jenkins et al. |
| 7,182,764 B2 | 2/2007 | Jenkins et al. |
| 7,357,774 B2 | 4/2008 | Cooper |
| 7,654,989 B2 | 2/2010 | Knapp |
| 7,789,875 B2 | 9/2010 | Brock et al. |
| 7,819,885 B2 | 10/2010 | Cooper |
| 7,850,642 B2 | 12/2010 | Moll et al. |
| 7,854,109 B2 | 12/2010 | Zubiate et al. |
| 7,854,738 B2 | 12/2010 | Lee et al. |
| 7,867,241 B2 | 1/2011 | Brock et al. |
| 7,883,475 B2 | 2/2011 | Dupont et al. |
| 7,918,845 B2 | 4/2011 | Saadat et al. |
| 7,946,546 B2 | 5/2011 | Zubiate et al. |
| 8,075,476 B2 * | 12/2011 | Vargas .......................... 600/114 |
| 8,100,031 B2 | 1/2012 | Zubiate et al. |
| 8,192,422 B2 | 6/2012 | Zubiate et al. |
| 8,257,303 B2 | 9/2012 | Moll et al. |
| 8,394,082 B2 | 3/2013 | Okamoto et al. |
| 8,459,138 B2 | 6/2013 | Zubiate et al. |
| 8,460,276 B2 | 6/2013 | Hashimoto et al. |
| 8,597,261 B2 | 12/2013 | Knapp |
| 8,617,102 B2 | 12/2013 | Moll et al. |
| 8,647,257 B2 * | 2/2014 | Jansen ................... A61B 1/005 600/104 |
| 8,771,173 B2 * | 7/2014 | Fonger ..................... A61B 1/32 600/106 |
| 8,801,661 B2 | 8/2014 | Moll et al. |
| 8,911,415 B2 | 12/2014 | Knapp |
| 8,945,096 B2 | 2/2015 | Zubiate et al. |
| 9,011,318 B2 | 4/2015 | Choset et al. |
| 9,295,811 B2 | 3/2016 | Knapp |
| 9,457,168 B2 | 10/2016 | Moll et al. |
| 9,505,125 B2 | 11/2016 | Zubiate et al. |
| 2001/0013764 A1 | 8/2001 | Blumenkranz et al. |
| 2002/0091374 A1 | 7/2002 | Cooper |
| 2002/0133174 A1 | 9/2002 | Charles et al. |
| 2002/0161281 A1 | 10/2002 | Jaffe et al. |
| 2003/0135203 A1 | 7/2003 | Wang et al. |
| 2003/0225312 A1 | 12/2003 | Suzuki et al. |
| 2004/0138529 A1 | 7/2004 | Wiltshire et al. |
| 2004/0193146 A1 | 9/2004 | Lee et al. |
| 2004/0204629 A1 | 10/2004 | Knapp |
| 2005/0021050 A1 | 1/2005 | Cooper |
| 2005/0033287 A1 | 2/2005 | Sra |
| 2005/0065397 A1 | 3/2005 | Saadat et al. |
| 2005/0090811 A1 | 4/2005 | Doyle et al. |
| 2005/0113640 A1 * | 5/2005 | Saadat et al. .................. 600/106 |
| 2005/0215992 A1 | 9/2005 | Jenkins et al. |
| 2005/0216033 A1 | 9/2005 | Lee et al. |
| 2006/0025654 A1 | 2/2006 | Suzuki et al. |
| 2006/0052664 A1 | 3/2006 | Julian et al. |
| 2007/0299387 A1 | 12/2007 | Williams et al. |
| 2008/0027279 A1 | 1/2008 | Abou El Kheir |
| 2008/0119868 A1 | 5/2008 | Sharp et al. |
| 2008/0147091 A1 | 6/2008 | Cooper |
| 2008/0163603 A1 | 7/2008 | Zubiate et al. |
| 2008/0188869 A1 | 8/2008 | Weitzner et al. |
| 2008/0245173 A1 | 10/2008 | Schwerin et al. |
| 2009/0030428 A1 | 1/2009 | Omori et al. |
| 2009/0171151 A1 | 7/2009 | Choset et al. |
| 2009/0326556 A1 | 12/2009 | Diolaiti et al. |
| 2010/0022825 A1 | 1/2010 | Yoshie |
| 2010/0063354 A1 | 3/2010 | Hashimoto et al. |
| 2010/0160735 A1 | 6/2010 | Bakos |
| 2010/0160736 A1 | 6/2010 | Padget et al. |
| 2010/0204713 A1 | 8/2010 | Ruiz Morales |
| 2010/0224022 A1 | 9/2010 | Choi et al. |
| 2010/0280325 A1 | 11/2010 | Ibrahim et al. |
| 2010/0318100 A1 | 12/2010 | Okamoto et al. |
| 2011/0028790 A1 | 2/2011 | Farr et al. |
| 2011/0028990 A1 | 2/2011 | Cooper |
| 2011/0056320 A1 | 3/2011 | Zubiate et al. |
| 2011/0066161 A1 | 3/2011 | Cooper |
| 2011/0098678 A1 | 4/2011 | Dupont et al. |
| 2011/0152613 A1 | 6/2011 | Zubiate et al. |
| 2011/0184241 A1 | 7/2011 | Zubiate et al. |
| 2011/0213384 A1 | 9/2011 | Jeong |
| 2011/0238083 A1 | 9/2011 | Moll et al. |
| 2011/0313243 A1 | 12/2011 | Zubiate et al. |
| 2012/0065467 A1 | 3/2012 | Moll et al. |
| 2012/0209073 A1 | 8/2012 | McWeeney et al. |
| 2012/0209174 A1 | 8/2012 | Moll et al. |
| 2013/0150673 A1 | 6/2013 | Kakehashi |
| 2014/0012287 A1 | 1/2014 | Oyola et al. |
| 2014/0081292 A1 | 3/2014 | Moll et al. |
| 2014/0088356 A1 | 3/2014 | Matsuo et al. |
| 2014/0296875 A1 | 10/2014 | Moll et al. |
| 2015/0164491 A1 | 6/2015 | Choset et al. |
| 2016/0174816 A1 | 6/2016 | Choset et al. |

FOREIGN PATENT DOCUMENTS

| | | |
|---|---|---|
| JP | 2003299663 | 10/2003 |
| JP | 2006522657 | 10/2006 |
| JP | 2008504072 | 2/2008 |
| JP | 2009500086 | 1/2009 |
| JP | 2009514610 | 4/2009 |
| JP | 2010057919 | 3/2010 |
| WO | 2007005976 | 1/2007 |
| WO | 2009149421 | 12/2009 |
| WO | 2010050771 | 5/2010 |
| WO | 2010055745 | 5/2010 |
| WO | 2012015659 | 2/2012 |

OTHER PUBLICATIONS

Swift, H. W., "Power Transmission by Belts: An Investigation of Fundamentals", The Institution of Mechanical Engineers, 1928.

Smith, G. A. et al., "Surgery", 1950, p. 817-821.

"Baby Robot", http://cyberneticzoo.com/wp-content/uploads/2010/03/Ticket-robot-russian-1973.pdf, 1970.

Rajac, "Variable-Pitch Transfer Mechanism", IBM Technical Disclosure Bulletin, 1974.

ZH Luo , "Theoretical and Experimental Study on Control of Flexible Robot Arms Using Direct Strain Feedback", 1992.

Bu Yonghong, Wang Yi, "The Identification of Geometric Link Parameters of Robot Manipulators", ACTAAutomatica Sinica, 1992.

Zheng Nanning Wang Long Hu chao Liu Jianqin, "Improved BP Neural Net and its Application to Handwritten Numeral Recognition", 1992.

Stefano Chiaverini, Bruno Siciliano, Olav Egeland, Robot Control in Singular Configurations—Analysis and Experimental Results, Experimental Robotics II, 1993, p. 25-34.

Antonio Bicchi, J. Kenneth Salisbury, David L. Brock, Experimental Evaluation of Friction Characteristics With an Articulated Robotic Hand, Experimental Robotics II, 1993, p. 153-167.

Claudio Melchiorri, Gabriele Vassura, Mechanical and Control Issues for Integration of an Arm-Hand Robotic System, Experimental Robotics II, 1993, p. 136-152.

Andrew K. Rist, Ellen Y. Lin, Bartholomew O. Nnaji, Ralph Application for Surface Mount Assembly, International Journal of Flexible Manufacturing Systems, 1993, p. 27-52.

R.H. Taylor, et al, A Model-Based Optimal Planning and Execution System With Active Sensing and Passive Manipulation for Augmentation of Human-Precision in Computer-Integrated Surgery, Lecture Notes in Control and Information Sciences; Experimental Robo, Jun. 25-27, 1991. pp. 179-195.

Nobuyuki Furuya, Masatomo Matubara, An Algorithm of Motor Control by Software Servo System (2nd Report): Application to 4-Axes Scara Robot, Journal of the Japan Society of Precision Engineering, 1993, p. 423-428.

H.S. Moon, S.Y. Lee, S.J. Na, A Study on Selection of Gas Metal Arc Welding Parameters of Fillet Joints Using Neural Network, Journal of the Korean Welding Society, 1993, p. 151-160.

(56) References Cited

OTHER PUBLICATIONS

Byong Suk Kim, Computer-Assisted System for Accident Analysis and Mul-Function Protection in Industrial Robot, Papersearch.net (Korean Studies Information Co.), 1993, p. 61-64.
J. I. Arocena, R. W. Daniel, P. Elosegul, End Point Control of Compliant Robots, Experimental Robotics II, 1993, p. 435-449.
Ho Kyung Kim, Nonlinear Static Analysis and Determination of Initial Equilibrium States of Suspension Bridges, 1993, p. 177-186.
Gimdongha, imhyeongyo (Dong Ha Kim, Hyeon Kyo Lim), Safe Speed Limit of Robot Arm During Teaching and Maintenance Work, 1993, p. 64-70.
Chang-Boo Kim, Seung-Hoon Lee, Inverse Dynamic Analysis of a Flexible Robot Arm With Multiple Joints by Using the Optimal Control Method, Journal of the Korean Society of Precision Engineering, 1993, p. 133-140.
Chang-Soo Han, The Optimum Design of a 6 D.O.F. Fully-Parallel Micromanipulator for Enhanced Robot Accuracy, Journal of the Korean Society of Precision Engineering, 1993, p. 42-51.
Nicholas Jackson, The Story Behind the Russian Robot Collie Patent Sketches, The Atlantic, 2011.
Oh Joong Chan, Jong Sik Boong, Choi Ko Bong, Kwon Key Jo, Design a Mobile Robot's Tracking Control System Using Fuzzy Theory, Sung Kyun Kwan Univ., 1992, p. 112-115.
Sang-Gwon Lim, Jin-Won Lee, Yong-Ky Moon, Dong-Lyeol Jeon, Sang-Hyun Jin, In-Hwan Oh, Dong-Il Kim, Sung-Kwun Kim, Development of AC Servo Motor Controller for Industrial Robotand CNC Machine System, Control R/D Team, Samsung Electronics, 1992, p. 1211-1214.
E.S. Jeon, S.H. Park, J.E. Oh, Singylarty Control of Robot Wrist Joints Using Euler Parameters, Journal of the Korean Society of Precision Engineering, 1992, p. 11-152.
Yoon Seok Chang, Hakil Kim, Motion Estimation of Moving Objects Using Frequency Domain Transforms, 1992, p. 92-99.
Nam Gu Lee, Chong Soo Lee, Chong-Xuk Park, Dynamic Hybrid Position/Force Controller for Two Cooperating Robots, 1992, p. 103-107.
Jong-Wu Moon, Jeung Park, Chong-Xuk Park, Adaptibe Control of a Flexible Robot Manipulator—Using ARMA Prediction Model, 1992, p. 122-127.
Dae-Gab Gweon, Choong-Min Jung, Development of a Robot Wrist for the Assembly of Chamferless Parts, Journal of the Korean Society of Precision Engineering, 1992, p. 36-43.
Fumio Harashima, Yaskuhiko Dote, Sensor-Based Robot Systems, Proc. IEEE Int. Symposium; Muroran Institute of Tech. (Japan), 1992, p. 10-19.
Chang-Boo Kim, Seung-Hoon Lee, Formulation of the Equation of Motion for Flexible Robotics Arms by Using the Finite Element Method, Inha Univ., Daewoo Heavy Industries Ltd, 1992, p. 233-238.
Jin-Geol Kim, A Study on the Robust Digital Tracking Control of a Robot With Flexible Joints, Journal of the Korean Society of Precision Engineering, 1992, p. 92-100.
Han-Sig Lee, The Prospects for the Future on Research of Flexible Automation and Robot System, 1992, p. 37-38.
Young Hood Joo, Seok Joo Yi, San Yeob Cha, Kwang Bang Woo, Hyung Woo Yoon, Gun Woong Hae, Sung Kwun Kim, A Study on Optimal Navigation of Autonomous Mobile Robot, Production of Eng. Division, Samsung Electronics Co., 1992, p. 128-133.
H. C. Shen, W. P. Yan, G. E. Taylor, Intelligent Sensory Decision-Making for Error Identification in Autonomous Robotics Systems, The International Journal of Advanced Manufacturing Technology, 1993, p. 377-384.
Morris R. Driels, W. Swayze, S. Potter, Full-Pose Calibration of a Root Manipulator Using a Coordinate-Measuring Machine, The International Journal of Advanced Manufacturing Technology, 1993, p. 34-41.
M. Wu, B. C. Jiang, Y. R. Shiau, Controlling a Robot's Position Using Neural Networks, The International Journal of Advanced Manufacturing Technology, 1993, p. 216-226.
Joachim O. Berg, Path and Orientation Accuracy of Industrial Robots, The International Journal of Advanced Manufacturing Technology, 1993, p. 29-33.
Shaheen Ahmad, Mohamed Zribi, Lyapunov-Based Control Design for Multiple Robots Handling a Common Object, Dynamics and Control, 1993, p. 127-157.
S.D. Park, K.W. Jeong, W.K. Chung, Y. Youm, Development of a Control Method Using Both Electric and Pneumatic Actuators for a Heavy Load Handing Robot, Journal of the Korean Society of Precision Engineering, 1993, p. 14-21.
Nicolay V. Kim, Algorithms of Observation Information Synthesis, International Conference on Electronics, Informations and Communications, 1993, p. 120-124.
Sung Do Chi, Seok Pil Lee, Wang Jae Lee, San Hui Park, Hierarchical Design of Intelligent Robot System, Hankuk Aviation Univ., Yonsel Univ., 1993, p. 213-216.
Cai Zi-Xing, Jiang Zhiming, High-Level Expert System-Based Robot Planning, 1993.
Yong-Deuk Seo, Dong-Joon Choi, Ki-Sang Hong, Hong Joeng, The Development of Intelligent Robot Using Vision and Speech Recognition System, Department of EE, POSTECH, 1993, p. 39-44.
Jae-Hun Jung, Yong-Hyun Jung, Jong-Mo Kim, Suck-Gyu Lee, Dal-Hae Lee, Motion Control of Autonomous Mobile Robot With Fuzzyalgorithm, Yeungnam Univ., 1993, p. 362-365.
Jin-Seob Choi, Dong-Won Kim, Sung-Mo Yang, A Study on the Pseudoinverse Kinematic Motion Control of 6-Axis Arc Welding Robot, Journal of the Korean Society of Precision Engineering, 1993, p. 170-177.
A Study on a Basic System Configuration for the PC Interface and the Robot Trajectory Generation, 1993, p. 354-358.
G.T. Yang, S.D. Ahn, S.C. Lee, Tip Position Control of Flexible Robot Arm by Self-Tuning Fuzzy Algorithm, Chonbuk Univ., 1993, p. 213-217.
Jeong Park, Hoe-Young Yoo, The Study of the Method of Position Control for the One-Link Flexible Robot Arm, 1993, p. 57-60.
Asea Industrial Robot System IRb-60, 1975, p. 1-8.
Robots Take a Hold on Production, 1982, p. 122-129.
M. Peter Heilburn, M.D., J., Preliminary Experience With Brown-Robert-Wells (BRW) Computerized Tomography Stereotaxis Guidance System, Neurourgery, 1983, p. 217-221.
International Machine Intelligence Robot System Users Manual, International Machine Intelligence, 1983.
Orbitran Wafer Handling Robot, Genmark Automation, 1989, p. 2,3,4.
H Kojima, R Toyama, Development of Wall Cleaning Robot, 1992.
Expo-70 Robot—Vadim Matskevich's students, http://cyberneticzoo.com/wp-content/uploads/2010/03/Expo-70-MK-1969-02-p31-3.pdf, 1969.
Conductor Robot, http://cyberneticzoo.com/wp-content/uploads/2010/03/Ticket-robot-russian-1973.pdf, 1973.
Michael L. Rhodes, "Computer Graphics and an Interactive Stereotactic System for CT-Aided Neurosurgery", IEEE Computer Graphics and Application, Computer Graphics in Medicine & Biology, 1983, p. 31-37.
Lee E. Weiss, Arthur C. Sanderson, Charles P. Neuman, "Dynamic Sensor Based Control of Robots with Visual Feedback", IEEE Journal of Robotics and Automation, 1987, p. 404-417.
Jean-Jacques E. Slotine, Weiping Li, "Composite adaptive control of robot manipulators", Automatica; Nonlinear Systems Laboratory, Massachusetts Institute of Technology, Cambridge, MA. 02139, U.S.A., 1989, p. 509-519.
Weiping Li, Jean-Jacques E. Slotine, "An indirect adaptive robot controller", Systems & Control Letters; Nonlinear Systems Laboratory, Massachusetts Institute of Technology Cambridge, MA 02139, U.S.A., 1989, p. 259-266.
Xu Hongbin, "Stability and performance robustness analysis of hybrid control for robot manipulators", Journal of UEST of China, vol. 22 No. 5, Oct. 1993, p. 501-505.
Francois Chaumette, Patrick Rives, Bernard Espiau, "Positioning of a Robot With Respect to an Object, Tracking it and Estimating its Velocity by Visual Servoing", IEEE International Conf. on Robotics and Automation, 1991, p. 2248-2253.

(56) References Cited

OTHER PUBLICATIONS

A.V. Timofejev, N.V. Ivanova, "Expert System of the Control Programs Designing of Adaptive Robots", The Lenigrand Institute of Aircraft Instrumentation, 1991, p. 912-915.
W Szczepiński, "Theory of polyhedrons of positioning accuracy of manipulators", Mechanism and Machine Theory; Institute of Fundamental Technological Research, Polish Academy of Sciences, 00-049 Warsaw, Swietokrzyska 21, Poland, 1991, p. 697-709.
Junji Furusho, Hiroshi Nagao, Naruse Makoto, "Multivariable Root Loci of Control Systems of Robot Manipulators with Flexible Driving Systems* : Distortion Feedback", JSME International Journal, 1992, p. 65-73.
Potemkin, E., Astafurov, P., Osipov, A., Malenkov, M., Mishkinyuk, V., Sologub, P., "Remote-controlled robots for repair and recovery in the zones of high radiation levels", Robotics and Automation, IEEE, 1992, p. 80-82.
S. L. Shishkin, "Adaptive control of a biped robot walking across a horizontal plane", International Journal of Adaptive Control and Signal Processing, 1992, p. 259-264.
Henk Nijmeijer, "Global regulation of robots using only position measurements", Systems and Control Letters; Department of Electrical Engineering, Mechatronics Research Centre Twente, University of Twente, P.O. Box 217, 7500 AE Enschede, Netherlands, 1992, p. 289-293.
Hitoshi Maekawa, Kazuhito Yokoi, Kazuo Tanie, Makoto Kaneko, Nobuo Kimura, Nobuaki Imamura, "Development of a three-fingered robot hand with stiffness control capability", Mechatronics; Mechanical Engineering Laboratory, 1992, p. 483-494.
J.D. Moon, D.W. Cho, "A component mode synthesis applied to mechanisms for an investigation of vibration", Journal of Sound and Vibration; Department of Mechanical Engineering, Pohang Institute of Science and Technology, Pohang, Korea, 1992, p. 67-79.
Timopheev, A.V., Prokhorov, D.V., "Neural networks processing systems in recognition and control problems", Neuroinformatics and Neurocomputers; IEEE, 1992, p. 820-828.
Jianguo Fu, Naresh K. Sinha, "An iterative learning scheme for motion control of robots using neural networks: A case study", Journal of Intelligent & Robotic Systems, 1993, p. 375-398.
Troccaz, J. Lavallee, S. Hellion, E., "A passive arm with dynamic constraints: a solution to safety problems in medical robotics", Systems Engineering in the Service of Humans', Conference Proceedings, 1993, p. 166-171.
Swarup, M. Gopal, "Comparative study on linearized robot models", Journal of Intelligent & Robotic Systems, 1993, p. 287-300.
H. Azaria, A. Dvir, "Algorithm optimization using a rule-based system. A case study: The Direct Kinematic Solution in robotics", Journal of Intelligent & Robotic Systems, 1993, p. 309-324.
Erick-Garcia-Benitez; Stephen Yurkovich; Kevin M. Passino, "Rule-Based Supervisory Control of a Two-Link Flexible Manipulator", Journal of Intelligent and Robotic Systems, 1993, p. 195-213.
K. Periyasamy, V. S. Alagar, T. D. Bui, "A formal framework for design and verification of robotic agents", Journal of Intelligent & Robotic Systems, 1993, p. 173-200.
S. Nicosia, A. Tornambè, P. Valigi, "State estimation in robotic manipulators: Some experimental results", Journal of Intelligent & Robotic Systems,, 1993, p. 321-351.
Dimitrios M Emiris, Vassilios D. Tourassis, "Singularity-robust decoupled control of dual-elbow manipulators", Journal of Intelligent & Robotic Systems, 1993, p. 225-243.
M.M Bayoumi, "Adaptive Control of Robots with Rigid Links: A Status Report", Department of Electrical Engineering, Queen's University, Ontario, Canada (IEEE), 1993, p. 232-236.
Y. Edan, B. A. Engel, G. E. Miles, "Intelligent control system simulation of an agricultural robot", Journal of Intelligent & Robotic Systems, 1993, p. 267-284.
Chun-Yi Su, "Adaptive sliding mode control of nonlinear robotic systems with time-varying parameters", Systems and Control Letters; Department of Mechanical Engineering, University of Victoria, Victoria, B.C. Canada V8W 3P6, 1993, p. 35-41.

Yalou Huang; Guizhang Lu, "Force Analysis and Hybrid Control Scheme for Multiple Robot Manipulators", Artificial Intelligence and Robotics Research Laboratories; Dept of Computer and System Sciences; Nankal University, China (Proceedings of the 1993 IEEE/RSJ International Conference on Intelligent Robots and Systems in Japan), 1993, p. 1530-1534.
C.M. Lim; T. Hiyama, "Experimental implementation of a fuzzy logic control scheme for a servomotor", Mechatronics; Department of Electronics Engineering, Ngee Ann Polytechnic, Singapore 2159 Singapore, Mechanics, vol. 3, No. 1. pp. 37-47. 1993.
E. Al-Gallaf, A.J. Allen, K. Warwick, "Dextrous hands: Issues relating to a four-finger articulated hand", Mechatronics; Department of Cybernetics, School of Engineering and Information Sciences, University of Reading, Reading, Berks RG6, 2AY, U.K., 1993, p. 329-342.
A. Swarup, M. Gopal, "On robustness of decentralized control for robot manipulators", Robotics and Autonomous Systems; Department of Electrical Engineering, Indian Institute of Technology, New Delhi—110016, India, 1993, p. 109-112.
L. Behara, M. Gopal, Santanu Chaudhury, "Trajectory tracking of robot manipulator using Gaussian networks", Dept. of Electrical Engineering, Indian Institute of Technolgy, Delhi, Hauz Khas, New Delhi 110 016, India, 1993.
E. V. Panteley, A. A. Stotsky, "Adaptive trajectory/force control scheme for costrained robot manipulators", International Journal of Adaptive Control and Signal Processing, 1993, p. 489-496.
Filaretov, V.F., "A Synthesis Of Adaptive Control Systems For Industrial Robots", Electronic Mfg Technology Symposium, 1993, p. 168-171.
S. Zenkevich, A. Maximov, A. Nazarova, A. Korshunov, "Control of robot-based assembly cell", Lecture Notes in Control and Information Sciences, 1993, p. 418-427.
D.E. Whitney, "The Mathematics of Coordinated Control of Prosthetic Arms and Manipulators", Asme Publication, 1972.
Shapiro, "Digital Technology Enables Robots to See", Computer Design, 1978.
Bejczy, A. K., Salisbury, Jr., J. K., "Kinesthetic Coupling Between Operator and Remote Manipulator", Advances in Computer Technology, 1980.
"An Improved CT-Aided Stereotactic Neurosurgery Technique", Fifth Annual Symposium on Computer Applications in Medical Care, 1981, p. 591-595.
Michael L. Thodes, Ph.D, "Stereotactic Neurosurgery Using 3D Image Data From Computed Tomography", Journal of Medical Systems, 1982, p. 106-118.
Salisburg, Jr., J. Kenneth, "Kinematic and Force Analysis of Articulated Hands", 1982.
"Minicomputer Control Robot's Six Electrohydraulic Servoactuators", Hydraulics & Pneumatics, 1982, p. 53-58.
F.M. Kulakov, "Modeling Robot Control in Assembly Operations", Modern Robot Engineering, Moscow, MIR Publishers, 1982, p. 100-116.
Bejczy et al., "Controlling Remote Manipulators Through Kinesthetic Coupling", Computers in Mechanical Engineering, 1983, p. 48-60.
L.E. Weiss, "Dynamic Visual Servo Control of Robots: an adaptive image-based approach, Technical Report", Carnegie Mellon, 1984.
Dennis E. Bullard, "CT-Guided Stereotactic Biopsies Using a Modified Grame and Gildenberg Techniques", Journal of Neurology, Neurosurgery and Psychiatry, 1984, p. 590-595.
M. Caporali et al., "Design and Construction of a Five Fingered Robotic Hand", Robotics Age, 1984, p. 14-20.
Salisbury, Jr., J. K., "Design and Control of an Articulated Hand", International Symposium on Dessign and Synthesis, 1984.
L. Dade Lunsford, M.D., "Stereotactic Exploration of the Brain in the Era of Computed Tomography", Surg. Neurol, 1984, p. 222-230.
Jacobsen, S.C., Iversen, E.K., Knutti, D. F., Johnson, R.T., Biggers, K. B., "Design of the Utah/MIT Dexterous Hand", Conf. on Robotics and Automation, 1986.
S. Hayati, M. Mirmirani, "Improving the Absolute positioning Accuracy of Robot Manipulators", Journal of Robotic Systems, 1986, p. 397-413.

(56) References Cited

OTHER PUBLICATIONS

Vertut, J., Coiffet, P., "Teleoperations and Robotics Evolution and Development", Robot Technology, 1986, p. 191-194.
L.E. Weiss; A.C. Sanderson, "Dynamic Sensor-based Control of Robots with Visual Feedback", IEEE Journal of Robotics and Automation, 1987, p. 5.
Townsend, W.T., Salisbury, Jr. J. K., "The Effect of Coulomb Friction and Stiction on Force Control", Conf. on Robotics and Automation, 1987.
P. Rives, F. Chaumette, B. Espiau, "Visual Servoing Based on a Task Function Approach", International Symposium on Experimental Robotics (Canada), 1989.
B.L. Davies, R.D. Hibberd, A. Timoney, J.E.A. Wickham, "A surgeon robot for prostatectomies", Proc. of 2nd Int. Conference on Robotics in Medicine (UK), 1989.
J.T. Feddema, C.S.G. Lee, O.R. Mitchell, "Automatic selection of image features for visual servoing of a robot manipulator", Conf. IEEE Robotics and Automation (USA), 1989, p. 14-19.
J.T. Feddema, O.R. Mitchell, "Vision-Guided Servoing with Feature-Based Trajectory Generation", IEEE Transaction on Robotics and Automation, 1989.
Pierre J. de Smet, Eugene I. Rivin, Yongle Lou, D. Kegg, "Robot Performance as Influenced by Mechanical System", CIRP Annals—Manufacturing Technology, 1990, p. 383-386.
Mills, J.K., "Hybrid actuation of robotic manipulators: an integral manifold control approach", Intelligent Control, IEEE, 1990, p. 817-823.
John T. Feddema, C. S. George Lee, "Adaptive Image Feature Prediction and Control for Visual Tracking with a Hand-eye Coordinated Camera", IEEE Transactions on Systems, man, and Cybernetics, 1990, p. 1172-1183.
Rafiqul I. Noorani, "Microcomputer-based robot arm control", Mathematical and Computer Modelling, 1990, p. 450-455.
Elysseev S., Kuznetzov, N., Lukyanov A., "Control of Robot Vibrations", 1990.
C. Samson, B. Espiau, "Robot Control: The Task Function Approach", Oxford Univ., 1990.
Adams, L, Krybus, W., Meyer-Ebrecht, D., Rueger, R., Gilsbach, J.M., Moesges, R., Schloendorff, G., "Computer Assisted Surgery", IEEE Computer Graphics and Application, 1990, p. 43-51.
B. Espiau, F. Chaumette, P. Rives, "A new approach to visual servoing in robotics", Research Report; IRISA/INRIA (France), 1990.
Korikov, Anatoliim, Syriamkin, Vladimiri, Titov, Vitaliis, "Correlation robot vision systems", 1990, p. 264.
Sadegh N, Hopowitz R, "Stability and robustness analysis of a class of adaptive controller for robotic manipulator", The International Journal of Robotics Research, 1990.
Rocheleau, D.N., Crane, C.D., III, "Development of a graphical interface for robotic operation in a hazardous environment", Systems, Man, and Cybernetics, 1991, p. 1077-1081.
J.C. Latombe, "Robot Motion Planning", The Kluwer International Series in Engineering and Computer Science, Kluwer Academic Publishers, 1991.
Kubota, T., Sato, M., Harashima, F., "Visual Control of Robotic Manipulator Based on Neural Networks", Industrial Electronics, IEEE, 1992, p. 490-496.
Nakamura, H., Shimada, T., Kobayashi, H., "An inspection robot for feeder cables-snake like motion control", Industrial Electronics, Control, Instrumentation, and Automation, 1992, p. 849-852.
P. Kazanzides, J. Zuhars, B. Mittelsstadt, R.H. Taylor, "Force sensing and control for a surgical robot", IEEE conference on Robotics and Automation (Nice), 1992, p. 612-617.
Vsevolod I. Astafyev Farus, Yakutsk, Russia Yuri M. Gorsky, "Homeostatics", Cybernetics and applied systems, 1992, p. 7-22.
S. Lavallee, J. Troccaz, L. Gaborit, A.L. Benabid, D. Hoffman, "Image guided operating robot: A clinical application in stereotactic neurosurgery", IEEE Conference on Robotics and Automation (Nice), 1992.
H.A. Paul, B. Mittelstadt, W.L. Bargar, B. Musits, R.H. Taylor, P. Kazanzides, J. Zuhars, B. Williamson, W. Hanson, "A surgical robot for total hip replacement surgery", IEEE Conference on Robotics and Automation (Nice), 1992, p. 606-611.
R.H. Taylor, et. al, Augmentation of Human Precision in Computer-Integrated Surgery, Innov. Tech. Biol. Med., 1992.
Takashi Matsui, Mochizuki Yoshihiro, Effect of Positive Angular Velocity Feedback on Torque Control of Hydraulic Actuator, JSME international journal, 1992, p. 406-412.
Ph, Cinquin, et. al, IGOR: Image Guided Operating Robot. Methodology, Medical Applications, Results, Innov. Tech. Biol. Med., 1992, p. 1048-1049.
Heung-Joo Jeon, Bum-Hee Lee, Robot Motion Planning for Time-Varying Obstacle Avoidance Using the Distance Function, 1992, p. 1429-1438.
Bose, B., Kalra, A.K., Thukral, S., Sood, A., Guha, S.K., Anand, S., Tremor Compensation for Robotics Assisted Microsurgery, Engineering in Medicine and Biology Society, 1992, p. 1067-1068.
Kenneth L. Hillsley, Stephen Yurkovich, Vibration Control of a Two-Link Flexible Robot Arm, Dynamics and Control, 1993, p. 261-280.
Canudas de Wit, C., Ortega, R., Seleme, S.I., Robot Motion Control Using Induction Motor Drives, Robotics and Automation, 1993, p. 533-538.
James K. Mills, Hybrid Actuator for Robot Manipulators: Design, Control and Performance, Robotics and Automation, IEEE Conference, 1993, p. 19-38.
Pietro Fanghella, Carlo Galletti; An Approach to Symbolic Kinematics to Multiloop Robot Mechanisms, RoManSy9, 1993, pp. 33-40.
Yozo Fujino, Pennung Warnitchal, B.M. Pacheco, Active Stiffnes Control of Cable Vibration, Journal of Applied Mechanics, 1993, p. 948-953.
Ng, W.S. Davies, B.L. Hibberd, R.D. Timoney, A.G., Robotic Surgery, Engineering in Medicine and Biology Magazine, 1993, p. 120-125.
J.L. Dallaway, R.M. Mahoney, R.D. Jackson, R.G. Gosine, An Interactive Robot Control Environment for Rehabilitation Applications, Robotica, 1993, p. 541-551.
Giulio E. Lancioni, Domenico Bellini, Doretta Oliva, "A robot to provide multi-handicaped blind persons with physical guidance and activity choices", Journal of Developmental and Physical Disabilities, 1993, p. 337-348.
Melzer A, Schurr MO, Kunert W, Buess G, Voges U, Meyer JU., Intelligent Surgical Instrument System ISIS. Concept and Preliminary Experimental Application of Components and Prototypes, Endosc Surg Allied Technol., 1993, p. 165-170.
John G. Hunter, Jonathan M. Sackier, Minimally Invasive Surgery, McGraw Hill, Inc., Health Professions Division, 1993.
Zhao Yu-shan Gu Liang-xian, Generalized Dynamic Model for Multibodies Manipulator, 1993.
F.M. Kulakov, Russian Research on Robotics, Intelligent Autonomous Systems, 1995, p. 53-62.
Shevtsova N.A., Faure A., Klepatch A.A., Podladchikova L.N., Rybak I.A., Model of Foveal Visual Preprocessor, Intelligent Robots and Computer Vision XIV: Algorithms, Techniques, Active Vision, and Materials Handling, 1995, p. 588-596.
International Search Report dated May 31, 2012, issued in corresponding International Application No. PCT/US2011/060214.
International Search Report and Written Opinion dated Nov. 28, 2012, issued in related International Application No. PCT/US2012/040414.
International Search Report and Written Opinion dated Feb. 27, 2013, issued in related International Application No. PCT/US2012/054802.
International Search Report and Written Opinion dated Apr. 25, 2013, issued in related International Application No. PCT/US2012/070924.
International Search Report and Written Opinion dated Apr. 6, 2012 issued in related International Application No. PCT/US2011/044811.
International Search Report and Written Opinion dated May 31, 2012, issued in related PCT/US2011/060214.

(56) References Cited

OTHER PUBLICATIONS

Australia Office Action dated Jun. 19, 2014, issued in related Australia Application No. 2011283048.
International Search Report and Written Opinion dated Dec. 9, 2013, issued in related International Application No. PCT/US2013/054326.
Extended European Search Report dated Sep. 16, 2014 issued in European Application No. 12793169.9-1660 / 2713931.
PCT ISRWO dated May 19, 2014, issued in International application No. PCT/US2014/010808.
International Search Report and Written Opinion dated May 30, 2012, issued in related International Application No. PCT/US2011/057282.
Japanese OA and English-language summary therof, dated Dec. 16, 2014 issued in corresponding Japanese Application No. 2013-538895.
Office Action Summary dated Aug. 18, 2015 from related Japanese Application 2013-538895.
Office Action Summary dated Jul. 21, 2015 from related Japanese Application 2013-538895.
Examination Report dated Feb. 11, 2016 in related Australian Application No. 2011338931.
Extended European Search Report dated Mar. 10, 2016 issued in corresponding European Application No. 11846539.2.
Decision of Rejection dated Jun. 21, 2016 in related Japanese Application No. 2013-538895 and English-language summary.
Examination Report dated Dec. 7, 2016 issued in corresponding Australian Application No. 2011338931.
Office Action dated Dec. 13, 2016 issued in corresponding Japanese Application No. 2013-538895, with English language summary.
Office Action dated Nov. 29, 2016 issued in corresponding Korean Application No. 9-5-2016-086038064.
European Office Action dated Feb. 7, 2017 issued in corresponding European Application No. 11846539.2.

\* cited by examiner

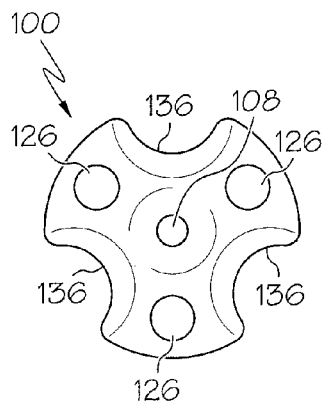
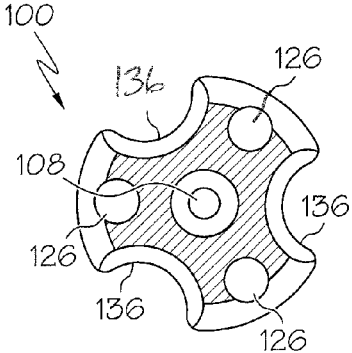
FIG. 17A  FIG. 17B
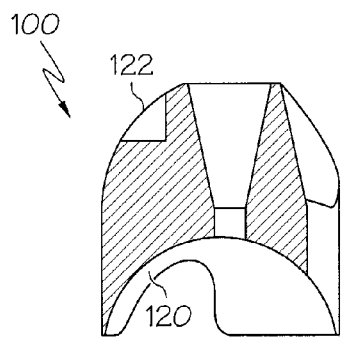
FIG. 17C
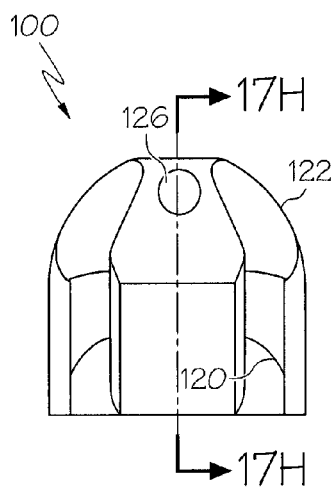
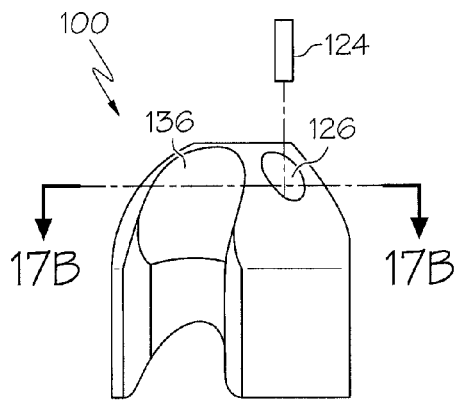
FIG. 17D  FIG. 17E

INTRODUCTION DEVICES FOR HIGHLY ARTICULATED ROBOTIC PROBES AND METHODS OF PRODUCTION AND USE OF SUCH PROBES

RELATED APPLICATIONS

This application claims the benefit of U.S. Provisional Application No. 61/412,733, filed Nov. 11, 2010, the content of which is incorporated herein by reference in its entirety.

This application claims the benefit of U.S. Provisional Application No. 61/534,032, filed Sep. 13, 2011, the content of which is incorporated herein by reference in its entirety.

This application claims the benefit of U.S. Provisional Application No. 61/472,344, filed Apr. 6, 2011, the content of which is incorporated herein by reference in its entirety.

This application claims the benefit of U.S. Provisional Application No. 61/492,578, filed Jun. 2, 2011, the content of which is incorporated herein by reference in its entirety.

This application is related to U.S. Provisional Application No. 61/406,032, filed Oct. 22, 2010, the content of which is incorporated herein by reference in its entirety.

This application is related to PCT Application No PCT/US2011/057282, filed Oct. 21, 2011, the content of which is incorporated herein by reference in its entirety.

This application is related to U.S. Provisional Application No. 61/368,257, filed Jul. 28, 2010, the content of which is incorporated herein by reference in its entirety.

This application is related to PCT Application No PCT/US2011/044811, filed Jul. 21, 2011, the content of which is incorporated herein by reference in its entirety.

This application is related to U.S. patent application Ser. No. 11/630,279, filed Dec. 20, 2006, published as U.S. Patent Application Publication No. 2009/0171151, the content of which is incorporated herein by reference in its entirety.

FIELD

Embodiments relate generally to the field of robotics and, more particularly, to an introduction device for three dimensional, flexible, steerable robotic devices.

BACKGROUND

There are numerous types of steerable multi-linked probes, and such devices are utilized in a variety of different applications. Robert Sturges' U.S. Pat. No. 5,759,151, which is hereby incorporated by reference in its entirety, discloses a flexible, steerable device for conducting exploratory procedures. The device includes at least one spine, each having stiffening means for selectively rendering the spine rigid and flexible along its length. A flexible sheath surrounds the spine and is axially slidably moveable relative to the spine so that the sheath will follow and conform to the shape of a spine in the rigid state and resist further flexure when the spine is in a relaxed state. A steerable distal tip is provided on the distal end of the device. Controls for the distal tip are mounted on the proximal end of the device. Mechanisms are provided on the distal end of the device for selectively activating and deactivating the stiffening means of the spine. An instrument conduit may be mounted on the sheath. Howard Choset's U.S. patent application Ser. No. 11/630, 279, which is hereby incorporated by reference in its entirety, discloses a feeder mechanism for advancing and retracting both an inner core and an outer sleeve, as well as selectively applying tension to control cables used for steering and causing either the inner core or outer sleeve to transition between a rigid state and a limp state.

U.S. Pat. No. 6,610,007, incorporated herein by reference, discloses a steerable endoscope having an elongated body with a selectively steerable distal portion and an automatically controlled proximal portion. The endoscope body is inserted into a patient and the selectively steerable distal portion is used to select a desired path within the patient's body. When the endoscope body is advanced, an electronic motion controller operates the automatically controlled proximal portion to assume the selected curve of the selectively steerable distal portion. Another desired path is selected with the selectively steerable distal portion and the endoscope body is advanced again. As the endoscope body is further advanced, the selected curves propagate proximally along the endoscope body, and when the endoscope body is withdrawn proximally, the selected curves propagate distally along the endoscope body. This creates a serpentine motion in the endoscope body allowing it to negotiate tortuous curves along a desired path through or around and between organs within the body.

For medical use and other critical applications, it is extremely important that each device not only perform as intended and within known specifications, but have repeatable performance and otherwise consistent operation from use to use. For these and other reasons, there is a need for improved systems, devices, and methods.

SUMMARY

An introduction assembly for an articulated probe, comprising: a feeding mechanism having at least one actuator for controlling the articulated probe; and an introduction device having a proximal end fixed in a positional relationship to the feeding mechanism, wherein the introduction device is configured to receive the articulated probe and provide a supporting force to the articulated probe.

In some embodiments, the introduction device is further configured to guide the articulated probe into a region of interest.

In some embodiments, the region of interest is selected from the group consisting of: the esophagus; the gastrointestinal tract; the pericardial space; the peritoneal space; and combinations thereof.

In some embodiments, the introduction device is connected to the feeding mechanism.

In some embodiments, the introduction device is configured to be disconnected from the feeding mechanism.

In some embodiments, the introduction device further comprises: a support member configured to support the articulated probe; an entrance positioned at the proximal end of the support member configured to guide the articulated probe into proximity with the support member; and an exit positioned at a distal end of the support member configured to guide the articulated probe from the support member into a region of interest.

In some embodiments, the introduction assembly further comprises a tool shaft guide.

In some embodiments, the tool shaft guide is configured to perform one or more of the following functions: slidingly receive a shaft of a tool; guide the shaft of a tool; provide a supporting force for a tool; and combinations thereof.

In some embodiments, the introduction assembly further comprises a collar attaching the tool shaft guide to the introduction device.

In some embodiments, the tool shaft guide is rotatably attached to the introduction device.

In some embodiments, the tool shaft guide is rotatably attached to the introduction device with one degree of freedom.

In some embodiments, the tool shaft guide is rotatably attached to the introduction device with multiple degrees of freedom.

In some embodiments, the introduction assembly further comprises a second tool shaft guide.

In some embodiments, the first tool shaft guide comprises a first geometry and the second tool shaft guide comprises a second geometry different than the first geometry.

In some embodiments, the tool shaft guide comprises multiple coaxial tubes.

In some embodiments, the tool shaft guide comprises a first tube comprising a first rigidity and a second tube comprising a second rigidity different than the first rigidity.

In some embodiments, the first tube slidingly receives the second tube.

In some embodiments, the first tube rigidity is greater than the second tube rigidity.

In some embodiments, the tool shaft guide comprises a proximal end and a tapered opening positioned on the proximal end.

In some embodiments, the tool shaft guide comprises a first portion and a second portion.

In some embodiments, the tool shaft guide further comprises a joint connecting the first portion and the second portion.

In some embodiments, the joint is selected from the group consisting of: a spherical joint; a hinged joint; and combinations thereof.

In some embodiments, the tool shaft guide comprises a bend portion constructed and arranged to allow an operator to modify the geometry of the tool shaft guide.

In some embodiments, the bend portion comprises a plastically deformable material.

In some embodiments, the articulated probe comprises a plurality of proximal links and a plurality of distal links.

In some embodiments, the plurality of proximal links and plurality of distal links are outer links.

In some embodiments, at least one of the plurality of proximal links comprises a first diameter, and at least one of the plurality of distal links comprises a second diameter, wherein the first diameter is less than the second diameter.

In some embodiments, the plurality of distal links are constructed and arranged to remain external to the introduction device.

In some embodiments, the introduction device comprises a distal end, and wherein one or more of the plurality of proximal links are constructed and arranged to pass through the introduction device distal end.

In another aspect, an introduction device for an articulated probe comprises: a support member configured to support an articulated probe; an entrance positioned at a proximal end of the support member configured to guide the articulated probe into proximity with the support member; and an exit positioned at a distal end of the support member configured to guide the articulated probe from the support member into a surrounding environment.

In some embodiments, the surrounding environment is selected from the group consisting of: the esophagus; the gastrointestinal tract; the pericardial space; the peritoneal space; and combinations thereof.

In some embodiments, the proximal end is configured to be attached to a feeding mechanism, and the entrance is configured to guide the articulated probe from the feeding mechanism into proximity with the support member.

In some embodiments, the proximal end is configured to be integral with the distal end of the feeding mechanism.

In some embodiments, the proximal end is configured to be removably attached to the distal end of the feeding mechanism.

In some embodiments, the distal end is configured to be inserted into a lumen.

In some embodiments, the lumen comprises a lumen of a patient's body.

In some embodiments, the support member comprises a rigid material.

In some embodiments, the support member comprises a flexible material.

In some embodiments, the support member comprises an axially curved member.

In some embodiments, the support member comprises a cylindrical tube.

In some embodiments, an inner diameter of the support member is larger than the outer diameter of the articulated probe.

In some embodiments, the support member comprises a first surface and a second surface.

In some embodiments, the first surface faces the second surface.

In some embodiments, a cross section perpendicular to the first surface and the second surface is substantially a circle.

In some embodiments, the support member surrounds a lumen.

In some embodiments, the introduction device further comprises a clamp configured to stabilize the articulated probe relative to the support member.

In some embodiments, the clamp is selected from the group consisting of: a lever, a cam, an expandable member such as a balloon; a piston such as a hydraulic or pneumatic piston; an electromagnetically activated actuator such as a solenoid; and combinations thereof.

In some embodiments, the clamp is configured to prevent the articulated probe from moving in one or more of the following ways: movement in a radial direction; movement in an axial direction; rotation; and combinations thereof.

In some embodiments, the support member surrounds a lumen.

In some embodiments, the inner diameter of the support member is larger than the outer diameter of the articulated probe.

In some embodiments, the clamp comprises a balloon configured to controllably expand and apply pressure on an outer surface of the articulated probe, such that the articulated probe can be stabilized in an axial direction; stabilized in a radial direction; and/or stabilized to prevent rotation relative to the introduction device.

In some embodiments, the clamp is configured to transmit a force between the support member and the articulated probe, said force applied to a surface area of the articulated probe of at least one square millimeter.

In some embodiments, the clamp is configured to transmit a force between the support member and the articulated probe, said force applied to a surface area of the articulated probe of at least ten square millimeters.

In some embodiments, the clamp is configured to transmit a force between the support member and the articulated probe, said force applied to a surface area of the articulated probe of at least one hundred square millimeters.

In some embodiments, the introduction device further comprises at least one channel extending at least partially along a longitudinal axis of the support member.

In some embodiments, the at least one channel comprises two or more channels.

In some embodiments, the two or more channels are positioned equidistantly apart on the introduction device.

In some embodiments, the at least one channel is constructed and arranged to slidingly receive the shaft of one or more tools.

In some embodiments, the at least one channel comprises a curvilinear channel.

In some embodiments, the introduction device further comprises a tool shaft guide.

In some embodiments, the tool shaft guide is configured to perform one or more of the following functions: slidingly receive a shaft of a tool; guide the shaft of a tool; provide a supporting force for a tool; and combinations thereof.

In some embodiments, the introduction device further comprises a collar attaching the tool shaft guide to the introduction In some embodiments, the tool shaft guide is rotatably attached to the introduction device.

In some embodiments, the tool shaft guide is rotatably attached to the introduction device with one degree of freedom.

In some embodiments, the tool shaft guide is rotatably attached to the introduction device with multiple degrees of freedom.

In some embodiments, the introduction device further comprises a second tool shaft guide.

In some embodiments, the first tool shaft guide comprises a first geometry and the second tool shaft guide comprises a second geometry different than the first tool shaft guide geometry.

In some embodiments, the tool shaft guide comprises multiple coaxial tubes.

In some embodiments, the tools shaft guide comprises a first tube comprising a first rigidity and a second tube comprising a second rigidity different than the first rigidity.

In some embodiments, the first tube slidingly receives the second tube.

In some embodiments, the first tube rigidity is greater than the second tube rigidity.

In some embodiments, the tool shaft guide comprises a proximal end and a tapered opening positioned on the proximal end.

In some embodiments, the tool shaft guide comprises a first portion and a second portion.

In some embodiments, the tool shaft guide further comprises a joint connecting the first portion and the second portion.

In some embodiments, the joint is selected from the group consisting of: a spherical joint; a hinged joint; and combinations thereof.

In some embodiments, the tool shaft guide comprises a bend portion constructed and arranged to allow an operator to modify the geometry of the tool shaft guide.

In some embodiments, the bend portion comprises a plastically deformable material.

In some embodiments, the articulated probe comprises a plurality of proximal links and a plurality of distal links.

In some embodiments, the plurality of proximal links and plurality of distal links are outer links.

In some embodiments, at least one of the plurality of proximal links comprises a first diameter, and at least one of the plurality of distal links comprises a second diameter, wherein the first diameter is less than the second diameter.

In some embodiments, the plurality of distal links are constructed and arranged to remain external to the introduction device.

In some embodiments, the introduction device comprises a distal end, and wherein one or more of the plurality of proximal links are constructed and arranged to pass through the introduction device distal end.

In some embodiments, the introduction device further comprises at least one tool channel on an outer surface of the introduction device and extending along a longitudinal axis of the introduction device, configured to guide a filament into a probe side port located on an outer surface of an articulated probe.

In some embodiments, the tool channel comprises a shaft connected to a tool port positioned on an outer surface of the introduction device.

In some embodiments, the at least one tool channel comprises a closed ring configured to slidingly receive the filament.

In some embodiments, the at least one tool channel comprises a ring and a slot in said ring, wherein the slot is configured to receive the filament.

In some embodiments, the slot is further configured to release the filament.

In another aspect, a method of introducing an articulated probe to a region of interest comprises: providing a support member configured to support an articulated probe and having a proximal end with an entrance and a distal end with an exit; inserting the support member into the region of interest; inserting the articulated probe into the entrance; and extending the articulated probe out of the exit such that a distal end of the articulated probe leaves the support member and enters the region of interest.

In some embodiments, inserting the articulated probe into the entrance is performed prior to inserting the support member into the region of interest.

In some embodiments, the method further comprises advancing a distal end of the articulated probe to a location proximate the exit prior to inserting the support member into the region of interest.

In some embodiments, the distal end of the articulated probe is advanced while the probe is in a flexible state.

In some embodiments, the distal end of the articulated probe is advanced manually.

In some embodiments, the distal end of the articulated probe is advanced by transitioning an outer sleeve of the articulated probe between a rigid state and a flexible state.

In some embodiments, the method further comprises: providing a feeding mechanism, wherein the proximal end is configured to be fixed in a positional relationship to the feeding mechanism, and wherein the articulated probe is guided from the feeding mechanism into the entrance.

In some embodiments, the region of interest comprises a lumen.

In some embodiments, the region of interest is selected from the group consisting of: the esophagus; the gastrointestinal tract; the pericardial space; the peritoneal space; and combinations thereof.

In some embodiments, the support member comprises an axially curved member.

In some embodiments, the support member comprises a cylindrical tube.

In some embodiments, an inner diameter of the support member is larger than the outer diameter of the articulated probe.

In some embodiments, the method further comprises controllably clamping the articulated probe within the support member so as to stabilize the articulated probe.

In some embodiments, the clamp comprises a balloon configured to controllably expand and apply pressure on an outer surface of the articulated probe, such that the articulated probe can be stabilized in an axial and/or radial direction within the support member.

In some embodiments, the method further comprises: providing at least one channel extending at least partially along a longitudinal axis of the support member; and extending a filament through the channel.

In some embodiments, the method further comprises: providing at least one tool channel on an outer surface of the support member and extending along a longitudinal axis of the support member, configured to guide a filament into a probe side port located on an outer surface of the articulated probe; and extending a filament through the tool channel.

In some embodiments, the tool channel comprises a shaft connected to a tool port positioned on an outer surface of the support member.

In another aspect, the present inventive concepts are directed to an introduction assembly as described in reference to the figures.

In another aspect, the present inventive concepts are directed to an introduction device as described in reference to the figures.

In another aspect, the present inventive concepts are directed to a method of introducing an articulated probe as described in reference to the figures.

BRIEF DESCRIPTION OF THE DRAWINGS

The foregoing and other objects, features and advantages of embodiments of the present inventive concepts will be apparent from the more particular description of embodiments, as illustrated in the accompanying drawings in which like reference characters refer to the same elements throughout the different views. The drawings are not necessarily to scale, emphasis instead being placed upon illustrating the principles of the embodiments. In the drawings.

DETAILED DESCRIPTION OF EMBODIMENTS

Embodiments of the present inventive concepts will now be described more fully hereinafter with reference to the accompanying drawings. This inventive concepts may, however, be embodied in different forms and should not be construed as limited to the embodiments set forth herein. Like numbers refer to like elements throughout the specification.

It will be understood that, although the terms first, second, third etc. may be used herein to describe various limitations, elements, components, regions, layers and/or sections, these limitations, elements, components, regions, layers and/or sections should not be limited by these terms. These terms are only used to distinguish one limitation, element, component, region, layer or section from another limitation, element, component, region, layer or section. Thus, a first limitation, element, component, region, layer or section discussed below could be termed a second limitation, element, component, region, layer or section, and vice-versa, without departing from the teachings of the present application.

It will be understood that when an element is referred to as being "on" or "connected" or "coupled" to another element, it can be directly on or connected or coupled to the other element or intervening elements can be present. In contrast, when an element is referred to as being "directly on" or "directly connected" or "directly coupled" to another element, there are no intervening elements present. Other words used to describe the relationship between elements should be interpreted in a like fashion (e.g., "between" versus "directly between," "adjacent" versus "directly adjacent," etc.). When an element is referred to herein as being "over" another element, it can be over or under the other element, and either directly coupled to the other element, or intervening elements may be present, or the elements may be spaced apart by a void or gap.

The terminology used herein is for the purpose of describing particular embodiments and is not intended to be limiting of the invention. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements, and/or components, but do not preclude the presence or addition of one or more other features, integers, steps, operations, elements, components, and/or groups thereof.

Overview of Highly Articulated Robotic Probe

Figure 1A:
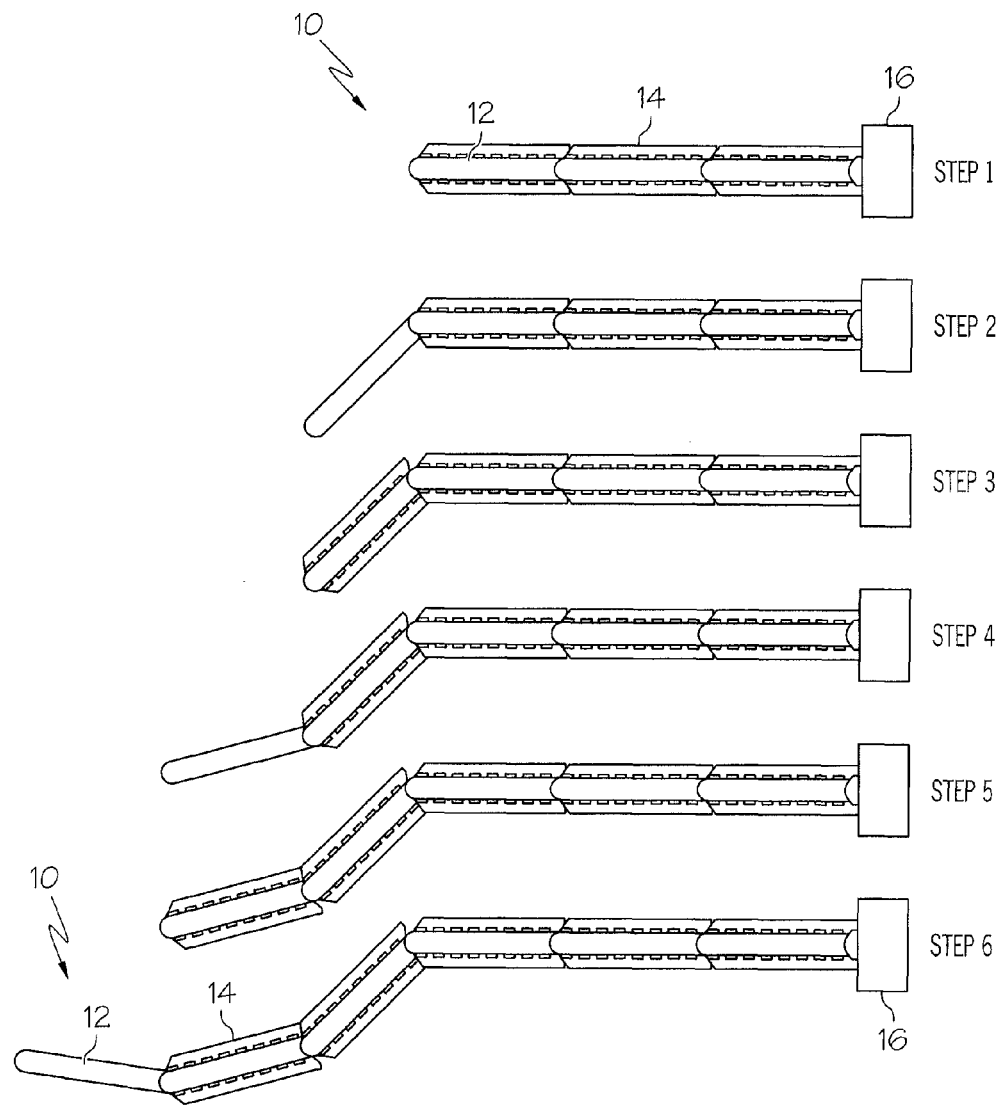
FIGS. 1A-1C are graphic demonstrations of a highly articulated probe device, consistent in accordance with the present inventive concepts.
Figure 1B:
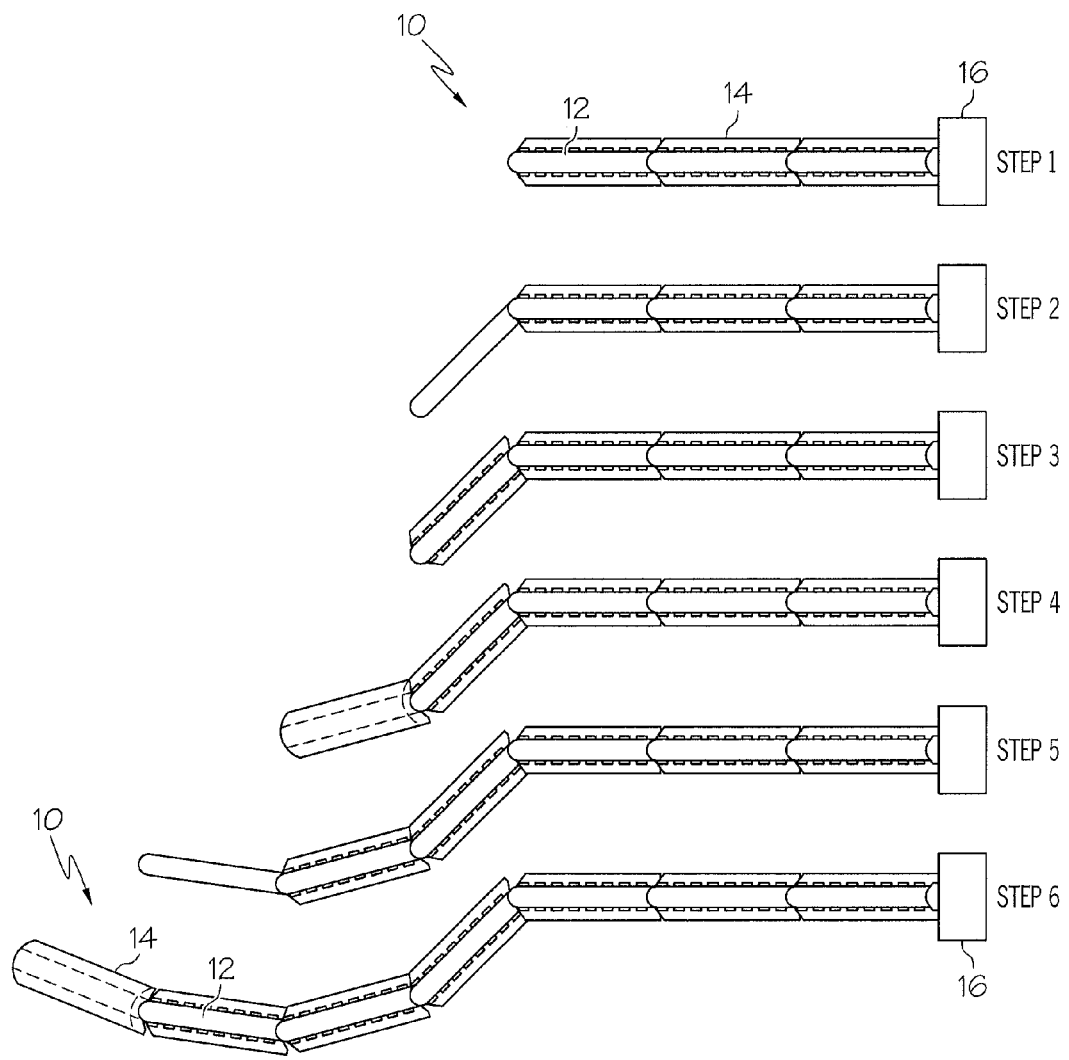
Figure 1C:
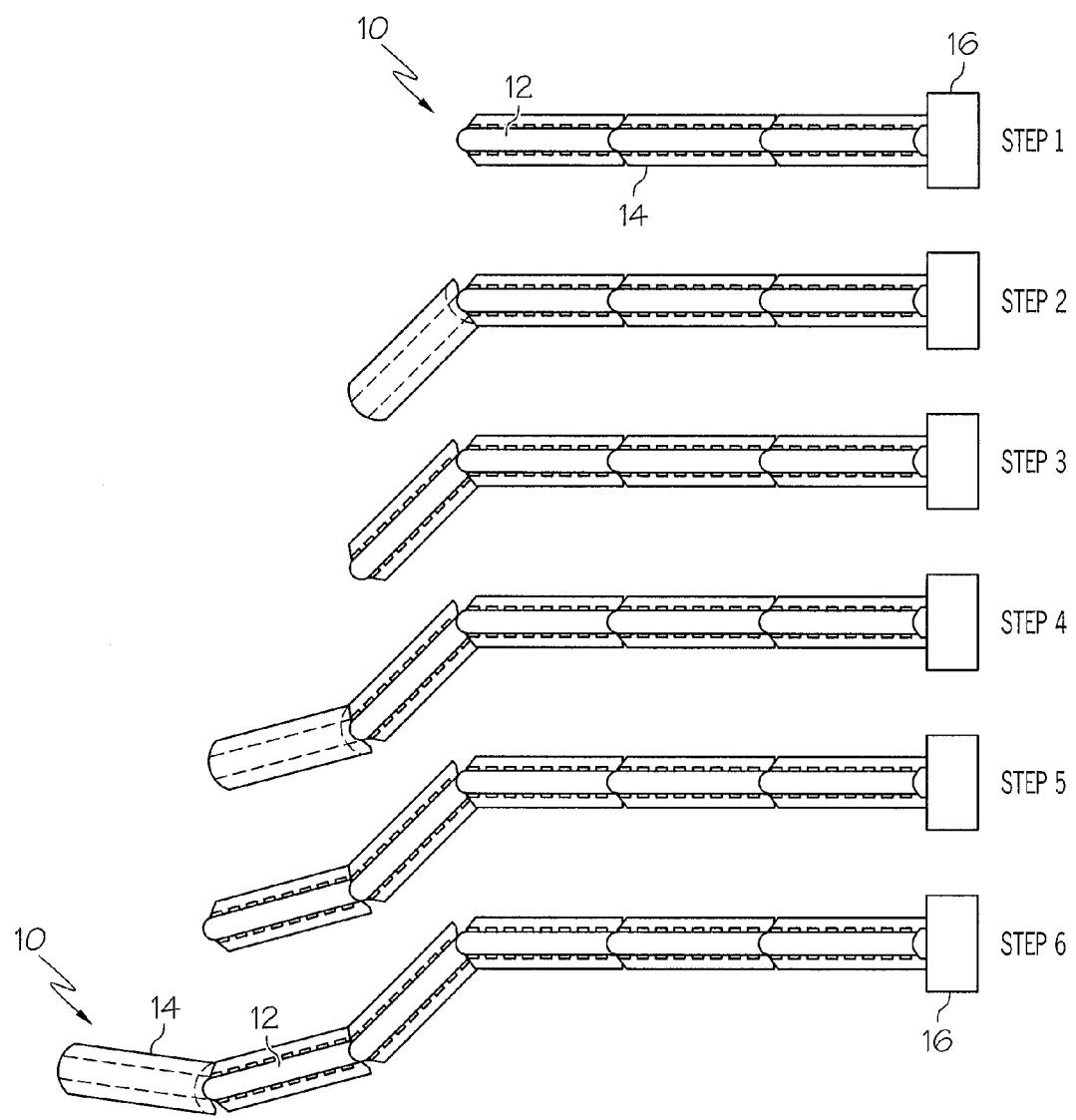

A highly articulated robotic probe 10, according to one embodiment shown in FIGS. 1A-1C, is essentially two concentric mechanisms, an outer one and an inner one, each of which can be viewed as a steerable mechanism. FIGS. 1A-1C show the concept of how different embodiments of the probe 10 operate. Referring to FIG. 1A, the inner mechanism is referred to as a first mechanism, an inner core or inner core mechanism 12. The outer mechanism is referred to as a second mechanism, an outer sleeve or outer sleeve mechanism 14. Each mechanism can alternate between being rigid and limp. In the rigid mode or state, the mechanism is just that—rigid. In the limp mode or state, the mechanism is highly flexible and thus either assumes the shape of its surroundings or can be reshaped. It should be noted that the term "limp" as used herein does not denote a structure that passively assumes a particular configuration dependent upon gravity and the shape of its environment; rather, the "limp" structures described in this application are capable of assuming positions and configurations that are desired by the operator of the device, and therefore are articulated and controlled rather than flaccid and passive.

With this probe 10, one mechanism starts limp and the other starts rigid. For the sake of explanation, assume the sleeve 14 is rigid and the core 12 is limp, as seen in step 1 in FIG. 1A. Now, the core 12 is both pushed forward by a feeding mechanism 16, described below, and its "head" or distal end is steered, as seen in step 2 in FIG. 1A. Now, the core 12 is made rigid and the sleeve 14 is made limp. The sleeve 14 is then pushed forward until it catches up or is coextensive with the core 12, as seen in step 3 in FIG. 1A. Now, the sleeve 14 is made rigid, the core 12 limp, and the procedure then repeats. One variation of this approach is to have the sleeve 14 be steerable as well. The operation of such a device is illustrated in FIG. 1B. In FIG. 1B it is seen that each mechanism is capable of catching up to the other and then advancing one link beyond. That requires an additional camera on the sleeve 14 but would potentially allow for quicker deployment of the probe 10. According to one embodiment, the sleeve 14 is steerable and the core 12 is not. The operation of such a device is shown in FIG. 1C.

In medical applications, once the probe 10 arrives at a desired location, the operator, typically a surgeon, can remove the inner core 12 and slide either a conventional device or a custom tool through the rigid sleeve 14 to perform various operations or insert the tool through a hole in the sleeve 14, as described below. The probe 10 is not limited to surgery, but can be used in engine inspection, engine repairs, and engine retrofitting. Other applications include tank inspection, spying or surveillance applications, bomb disarming, and inspection or repairs in tightly confined spaces such as submarines or within nuclear weapons. Other applications include structural (e.g. building) inspections, hazardous waste remediation and bioterrorists sample recovery. Clearly, the device of the present disclosure has a wide variety of applications and should not be taken as being limited to any particular application.

Figure 2A:
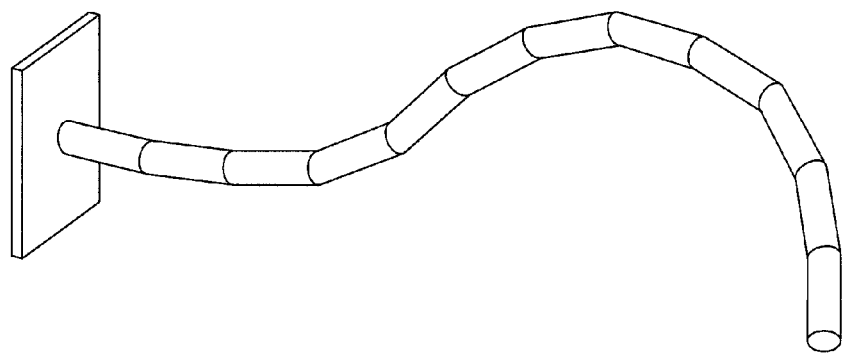
FIGS. 2A-2B illustrate various configurations assumed by a highly articulated probe, in accordance with the present inventive concepts.
Figure 2B:
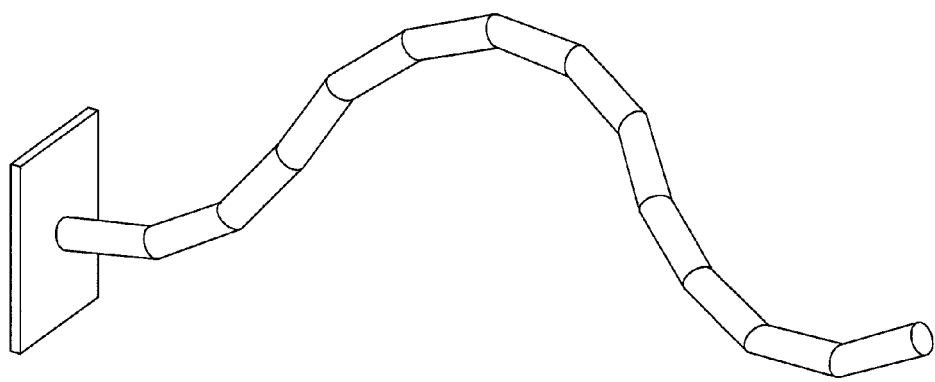
Figure 3A:
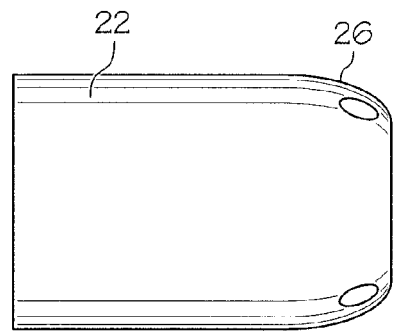
FIGS. 3A-3D illustrate various views of a cylinder of an outer sleeve, in accordance with the present inventive concepts.
Figure 3B:
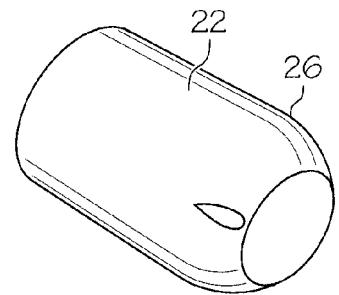
Figure 3C:
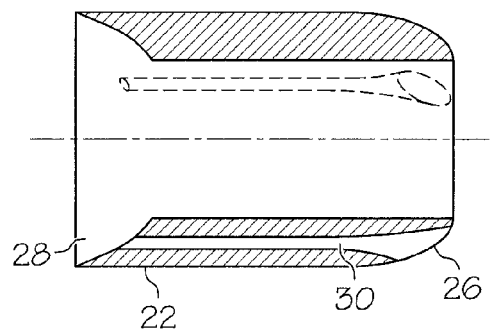
Figure 3D:
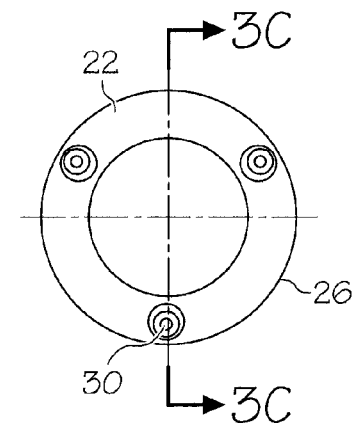
Figure 4B:
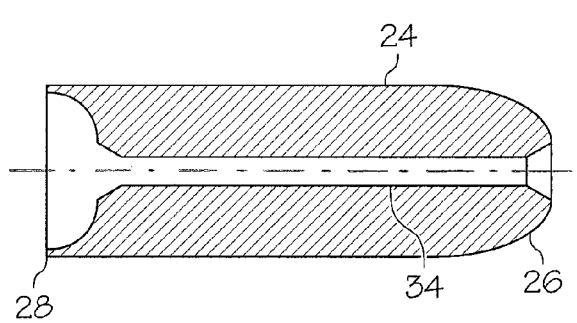
FIGS. 4A and 4B illustrate end and cross-sectional views, respectively, of a cylinder of an inner core, in accordance with the present inventive concepts.
Figure 4A:
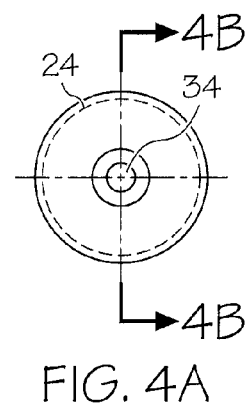

Inner core 12 and/or outer sleeve 14 are steerable and the inner core 12 and outer sleeve 14 can be made both rigid and limp, allowing probe 10 to drive anywhere in three-dimensions. Probe 10 can "remember" its previous configurations and for this reason, probe 10 can go anywhere in a three dimensional volume such as the intracavity spaces in a body. FIGS. 2A-2B illustrate examples of various configurations assumable by probe 10.

As can be seen in FIGS. 3A-3D and 4A and 4B, according to one embodiment, the outer sleeve 14 and inner core 12, respectively, can be made up of concentric cylinders 22, 24, respectively, although links of other shapes may be used, e.g. a dog bone configuration (not shown) as well as links of a type that are not concentric, e.g. backbone configuration, among others. The ends of the links 22, 24 are not flat but instead one end 26 is an "outer" or convex hemisphere and the other end 28 is an "inner" or concave hemisphere, both with similar radii of curvature. The links 22 of the outer sleeve 14 are "chained" back-to-back such that the concave end 28 of one mates with the convex end 26 of an adjacent cylinder. Similarly, the links 24 of the inner core 12 are chained back-to-back. The result is a spherical-like joint, from a kinematic point of view. In the current embodiment, each link is able to rotate on the adjacent link's head, acting as a spherical joint with approximately 10-20 degrees range of motion in any direction, although other ranges of motion are possible and potentially advantageous. According to one embodiment, the links 22 have a plurality of channels 30 extending therethrough for control cables or elongate devices such as elongate tools.

The heads (i.e. the distal links) of either or both the outer sleeve 14 and the inner core 12 are steerable using three cables which are attached at, for example, 120° from each other. As can be seen in FIGS. 3A-3D, there are three small cylindrical channels 30 for cables to pass through. In the version of the device shown in FIGS. 4A and 4B, the inner link 24 has only one cable, in which case there is only one hole 34 through its center.

It will be appreciated that although the embodiment described above utilizes cables such as conductive or non-conductive wires or other flexible filamentous structure, alternative means of manipulating the limp elements, such as miniature pneumatic or hydraulic pistons or other mechanical linkages situated between individual links, can be employed without falling outside the scope of the present inventive concepts.

The links, and hence probe 10, can be made out of virtually any material, including plastic or other magnetic resonance imaging compatible material. The outer sleeve 14 may assume a broad range of diameters, typically greater than 5 mm. Similarly, inner core 12 may assume a broad range of diameters, less than the diameter of outer sleeve 14 and typically more than 3 mm. The total number of links can vary over a large range but is typically greater than 10 links.

As noted, the inner core 12 and outer sleeve 14 can be made rigid or limp using cables or other flexible filament structures. In one embodiment, outer sleeve 14 consists of a set of links 22 strung on three cables. The three cables are typically 120 degrees apart, making it possible to steer in any direction. The radius of curvature of the probe 10 is dependent on a number of factors including length of links 22 as well as mating dimensions between the ends of mating links 22. When the cables are pulled toward the back of the sleeve 14, the links 22 are pulled toward each other. When the pulling force increases, the friction force between adjacent links 22 increases until the entire outer sleeve 14 stiffens (i.e. enters the rigid mode). When the pulling force is released, the outer sleeve 14 becomes limp. Thus, the cables together with their respective tensioning assemblies, which can include, for example, their corresponding cable motors and cable pulley assemblies, comprise a locking device. The tensioning assemblies, along with the electronics for controlling the tensioning assemblies, form a means for controlling the tension on the cable. When the outer sleeve 14 is positioned one link in front of the inner core 12, and the inner core 12 is stiff, the distal link of the outer sleeve 14 can be oriented by pulling one or more of the three cables. In addition to advancing or retracting cable, the magnitude of the pulling force which is exerted on each cable can be monitored or controlled. By pulling the three cables with the same magnitude, the outer sleeve 14 becomes stiff without changing its shape.

The inner core 12, like the outer sleeve 14, consists of a set of links. According to one embodiment, in contrast to the outer sleeve 14, the inner core 12 does not need (but may optionally have) a steering ability. The inner core 12 does need the ability to change from rigid mode, to limp mode, and back. Therefore, in embodiments where the inner core 12 need not be steerable, the links of the inner core 12 may be strung on a single cable, which enables a reduced overall diameter for the probe 10.

Overview of Feeding Mechanism

Figure 5A:
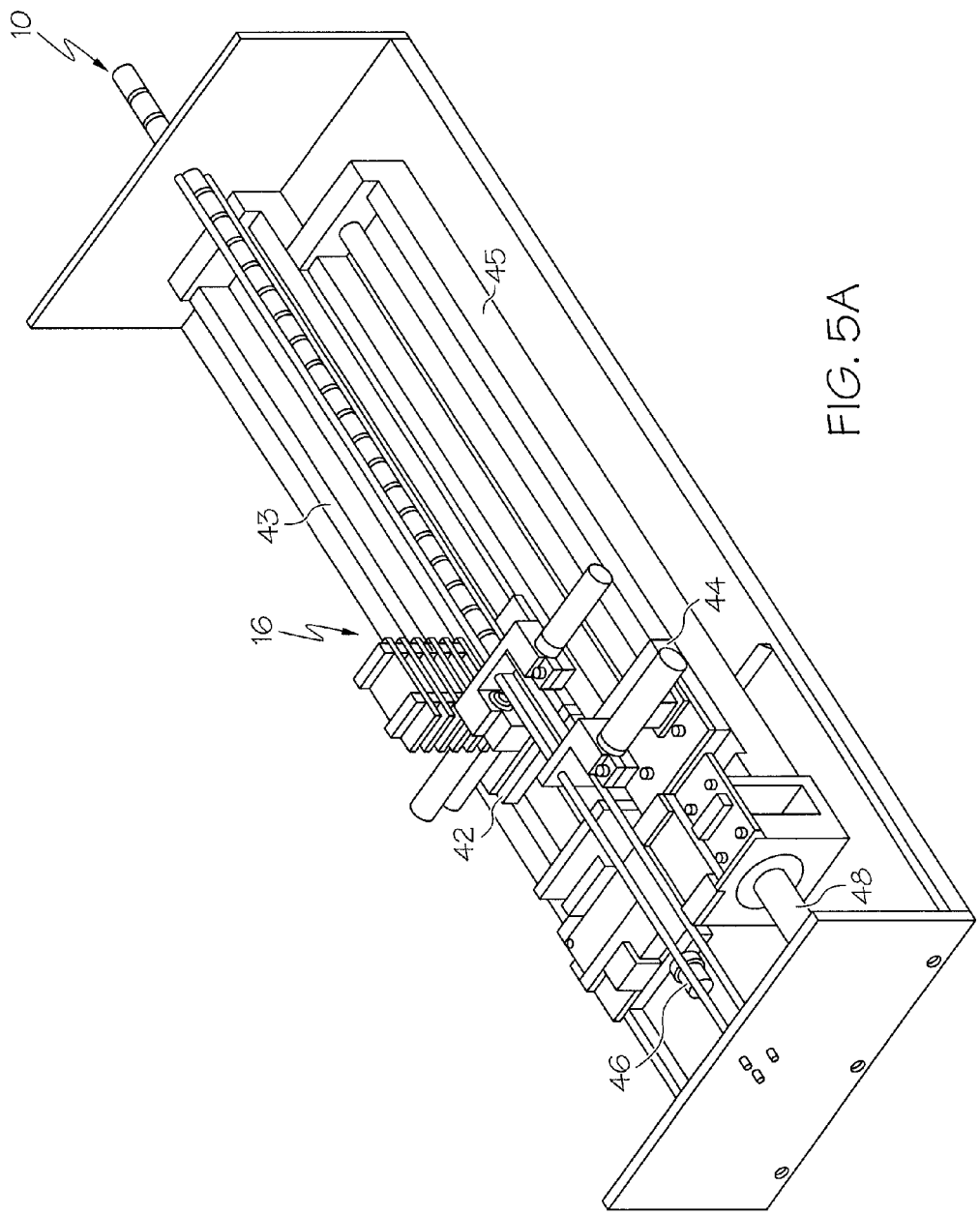
FIGS. 5A and 5B illustrates one example of a feeder mechanism, in accordance with the present inventive concepts.
Figure 5B:
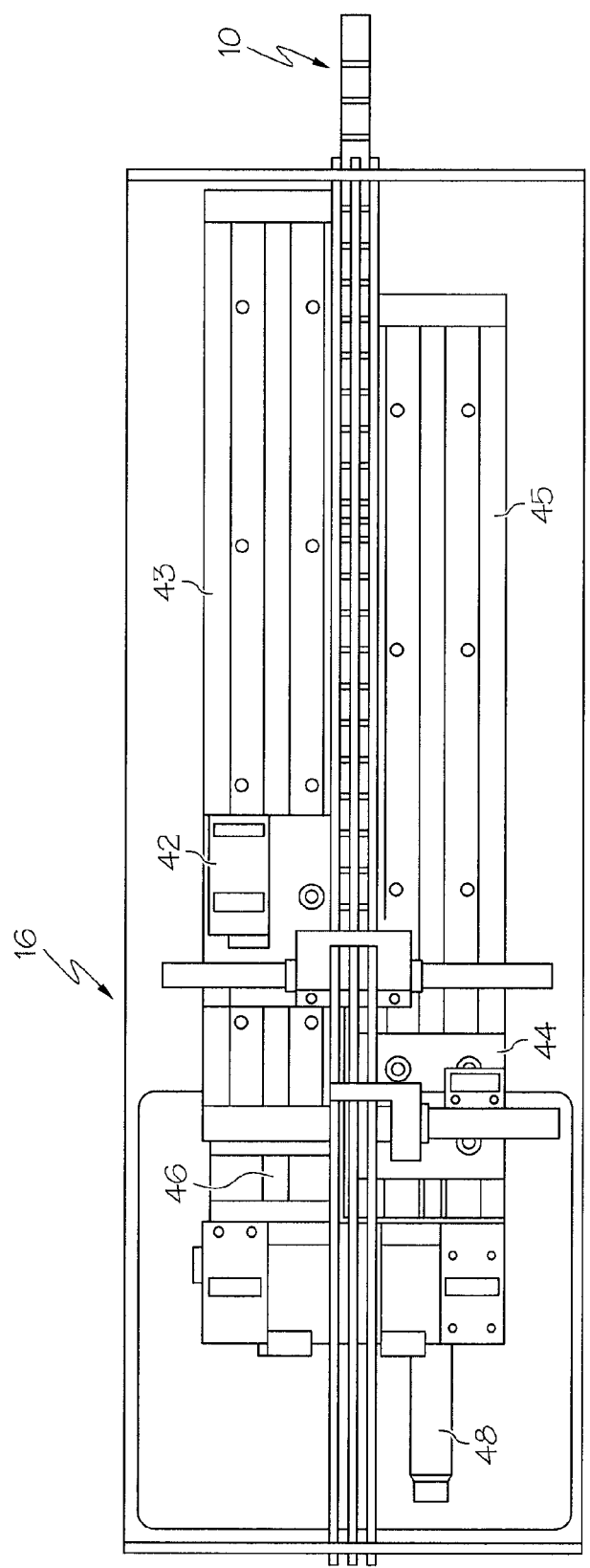

As mentioned above, a feeding mechanism 16 can be used to control the probe 10. One type of feeding mechanism 16, shown in FIGS. 5A and 5B, inserts and retracts the probe 10 into and out of, respectively, a region of interest such as the esophagus, the peritoneal space, the pericardial cavity, or another internal space of a patient. The feeder 16 has two movable carts. A first cart 42, carried in a first fixed tray 43, drives the outer sleeve 14 while a second cart 44 carried in a second fixed tray 45 drives the inner core 12. Each cart 42, 44, and hence each of the inner core 12 and outer sleeve 14, is driven independently by separate linear actuators 46, 48 respectively. The linear actuators 46, 48 may carry shaft encoders (not shown) used for position control as is known. Alternatively or additionally, motor current may be monitored to determine a value for tension in a cable used to control position. Cable tension may be monitored with one or more sensors such as a load cell. Numerous positioning and other sensors may be included to provide information relative to cable tension; cart position; probe orientation and configuration; and other system parameters. Typical sensors include but are not limited to: optical sensors; magnetic sensors such as Hall effect sensors; force and pressure sensors such as accelerometers, strain gauges and mechanical switches; and combinations of these. One or more sensors may be positioned in multiple locations including but not limited to: feeding mechanism 16, inner core 12 and outer sleeve 14.

Figure 6:
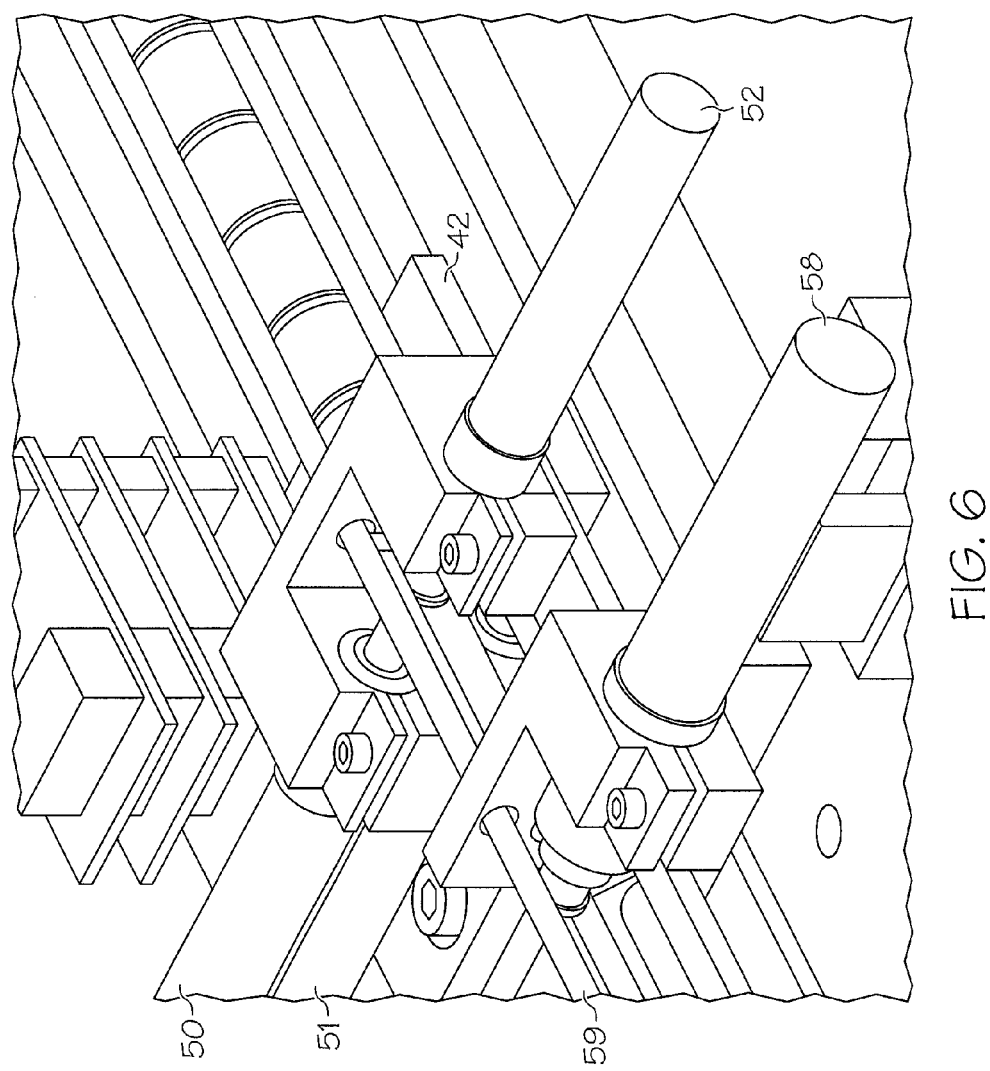
FIG. 6 illustrates devices for controlling the tension on cables, in accordance with the present inventive concepts.
Figure 7:
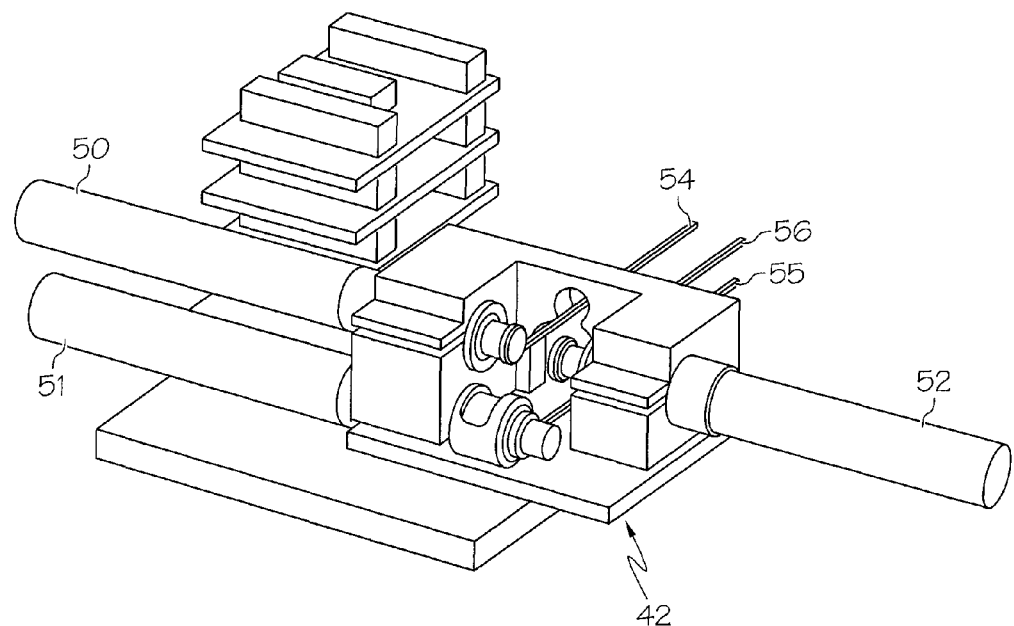
FIG. 7 illustrates devices for controlling the tension on the cables of the outer sleeve, in accordance with the present inventive concepts.
Figure 8:
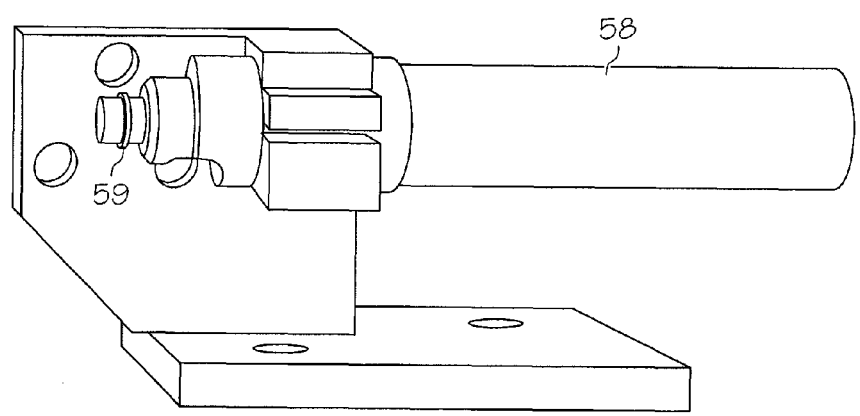
FIG. 8 illustrates a device for controlling the tension on the cable of the inner sleeve, in accordance with the present inventive concepts.

Each of the carts 42, 44 carries one or more motors necessary for controlling the cables of the inner core 12 and outer sleeve 14. For example, as seen in FIG. 6 and FIG. 7, the cart 42 carries motors 50, 51, 52 which control the tension on cables 54, 55, 56 of outer sleeve 14. As shown in FIG. 8, second cart 44 has a motor 58 for controlling the tension on cable 59 of the inner core 12. Each of the motors 50, 51, 52 and 58 may be provided with shaft encoders (not shown) used for position control as is known. In an embodiment where the inner core 12 is steerable, the inner core 12 requires two or more motors (e.g., to tension two or more cables) or another cable tensioning mechanism.

Figure 9:
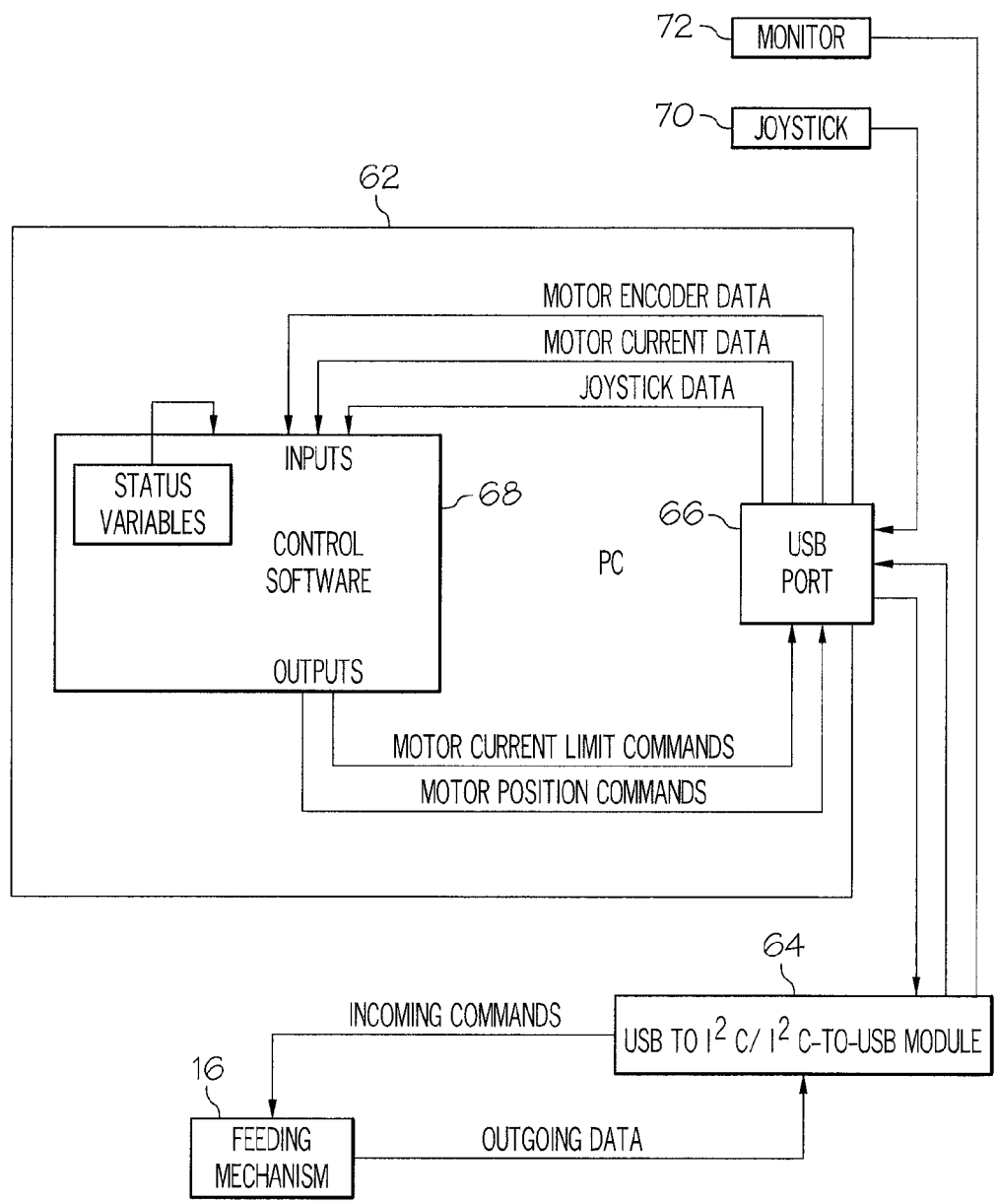
FIG. 9 is a block diagram illustrating the components of a control system and the flow of information between those components, in accordance with the present inventive concepts.
Figure 10A:
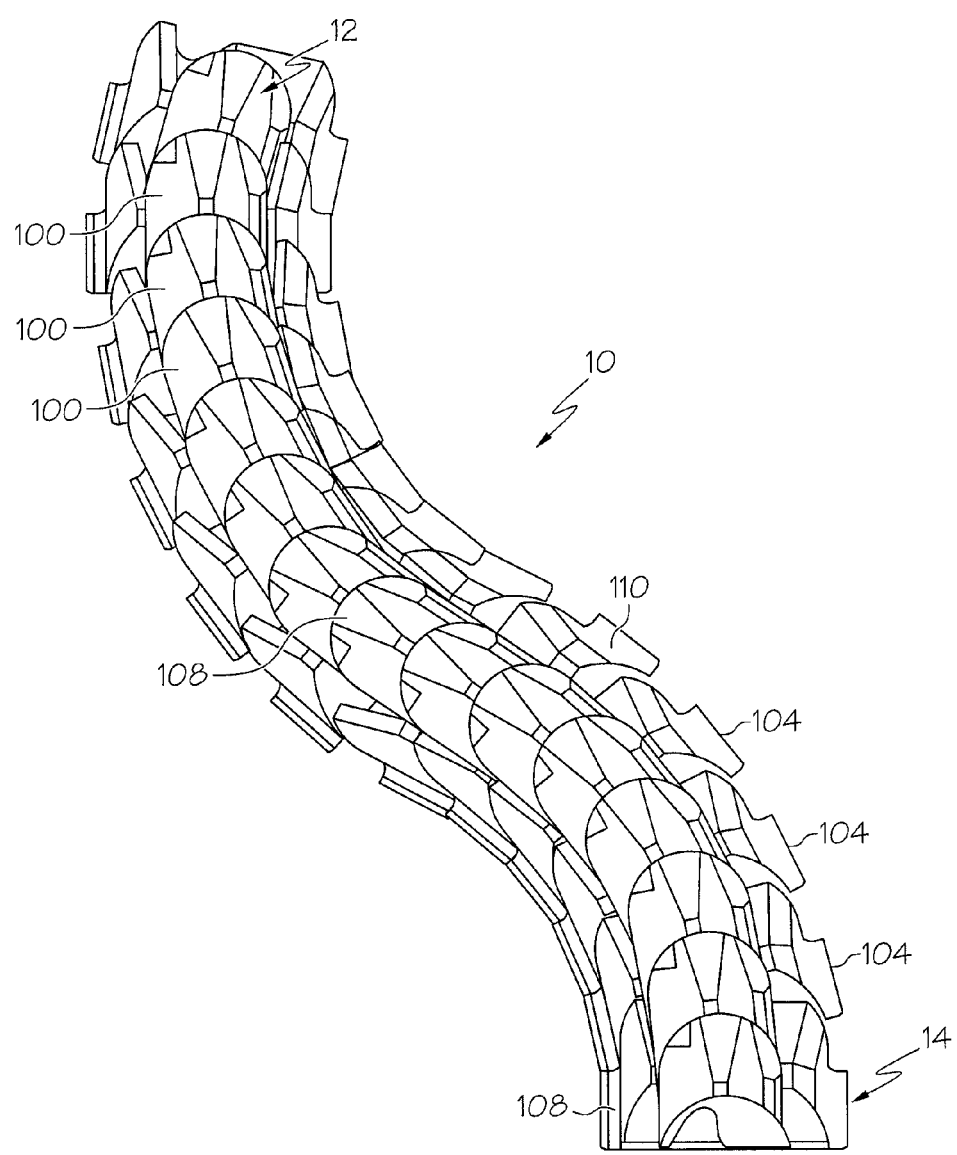
FIGS. 10A and 10B illustrate a cross section of an articulated probe according to an embodiment, in accordance with the present inventive concepts.
Figure 10B:
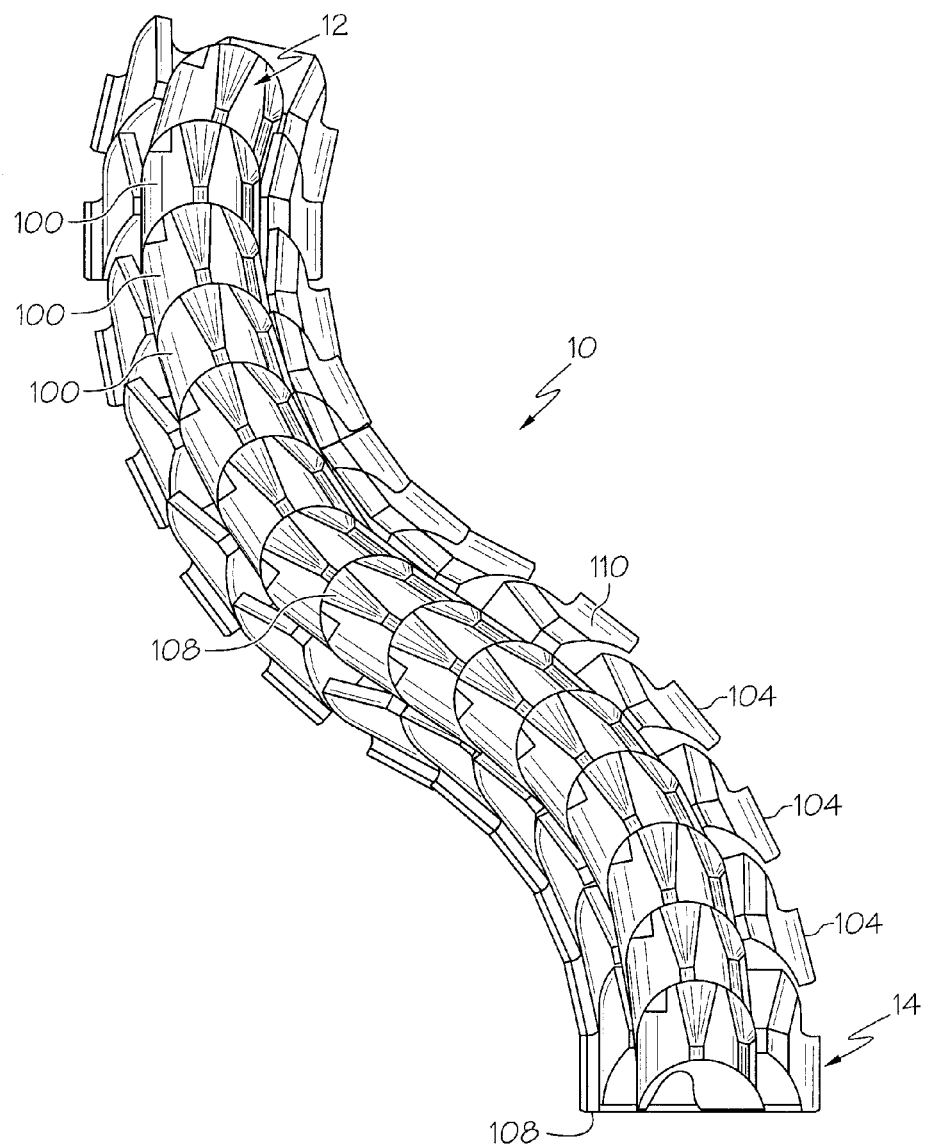

FIG. 9 is a block diagram illustrating the components of one embodiment of a control system and the flow of information between those components. The feeding mechanism 16 interfaces with a control computer 62 through a bus conversion module 64. Outgoing data from the feeding mechanism 16 is input to the module 64 for conversion to the USB and is then input to a USB port 66 on the computer 62. Incoming data to control software 68 may include motor current data, motor encoder data and/or cable tension data associated with each of the cables in the feeding mechanism 16. Alternatively or additionally, incoming data to control software 68 may include data from one or more sensors located in feeding mechanism 16, inner core 12 or outer sleeve 14. Joystick data (position data) may also be received from a joystick 70. A monitor 72 may be responsive to video data from a camera mounted on the distal end of the outer sleeve 14 and/or inner core 12 to provide visual feedback to a user regarding the position of the distal end of the probe 10. The control software 68 may output motor current limit commands and motor position commands which are input to the feeding mechanism 16.

Inner Core and Outer Sleeve

FIGS. 10A-11B illustrate an embodiment of the articulated probe 10 with the inner core 12 and the outer sleeve 14. The inner core 12 has a plurality of inner links 100 (preferably at least three, and, in some embodiments, fifty or more). The outer sleeve 14 has a plurality of outer links 104 (preferably at least three, and, in some embodiments, more preferably forty or more).

Figure 11A:
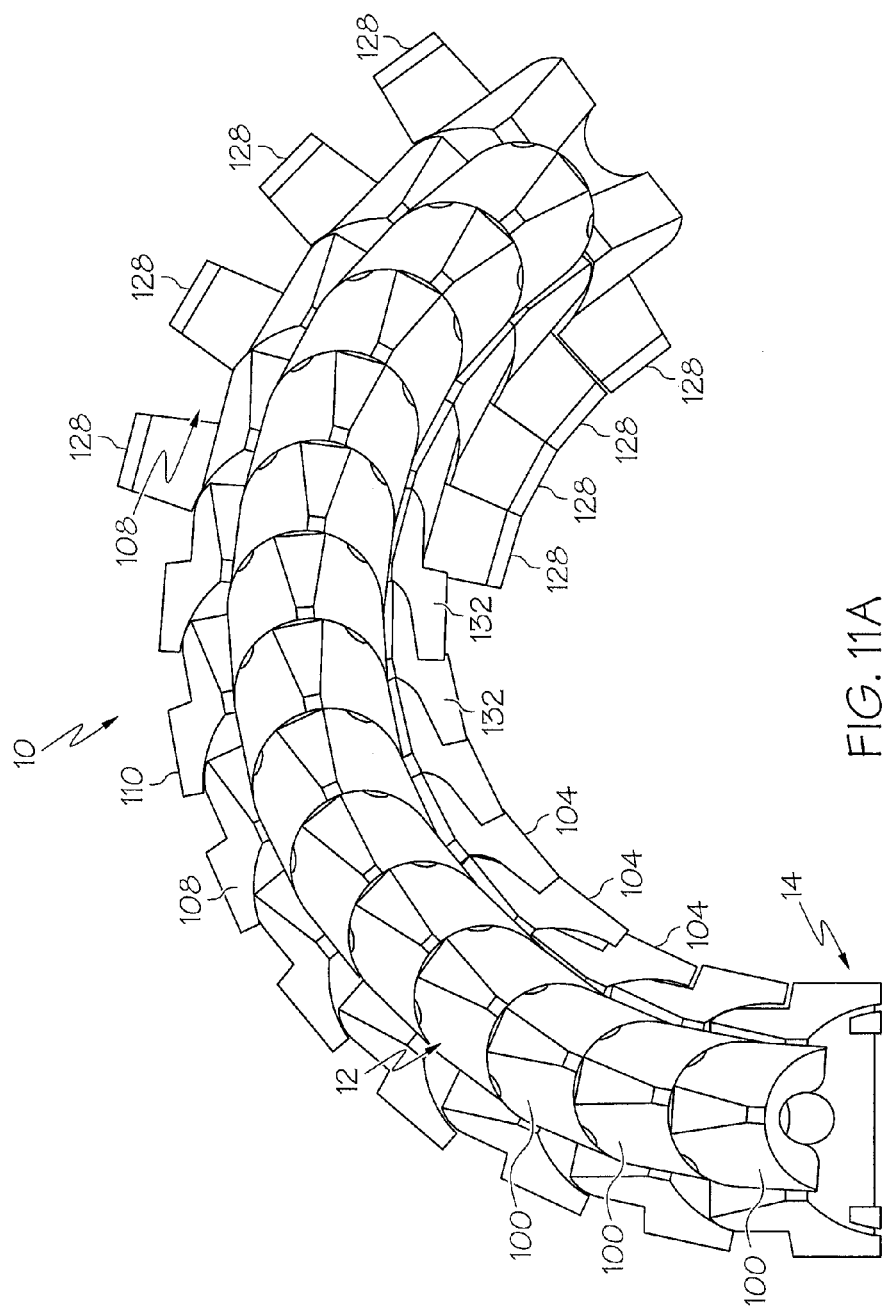
FIGS. 11A and 11B illustrate a cross section of an articulated probe according to an embodiment, in accordance with the present inventive concepts.
Figure 11B:
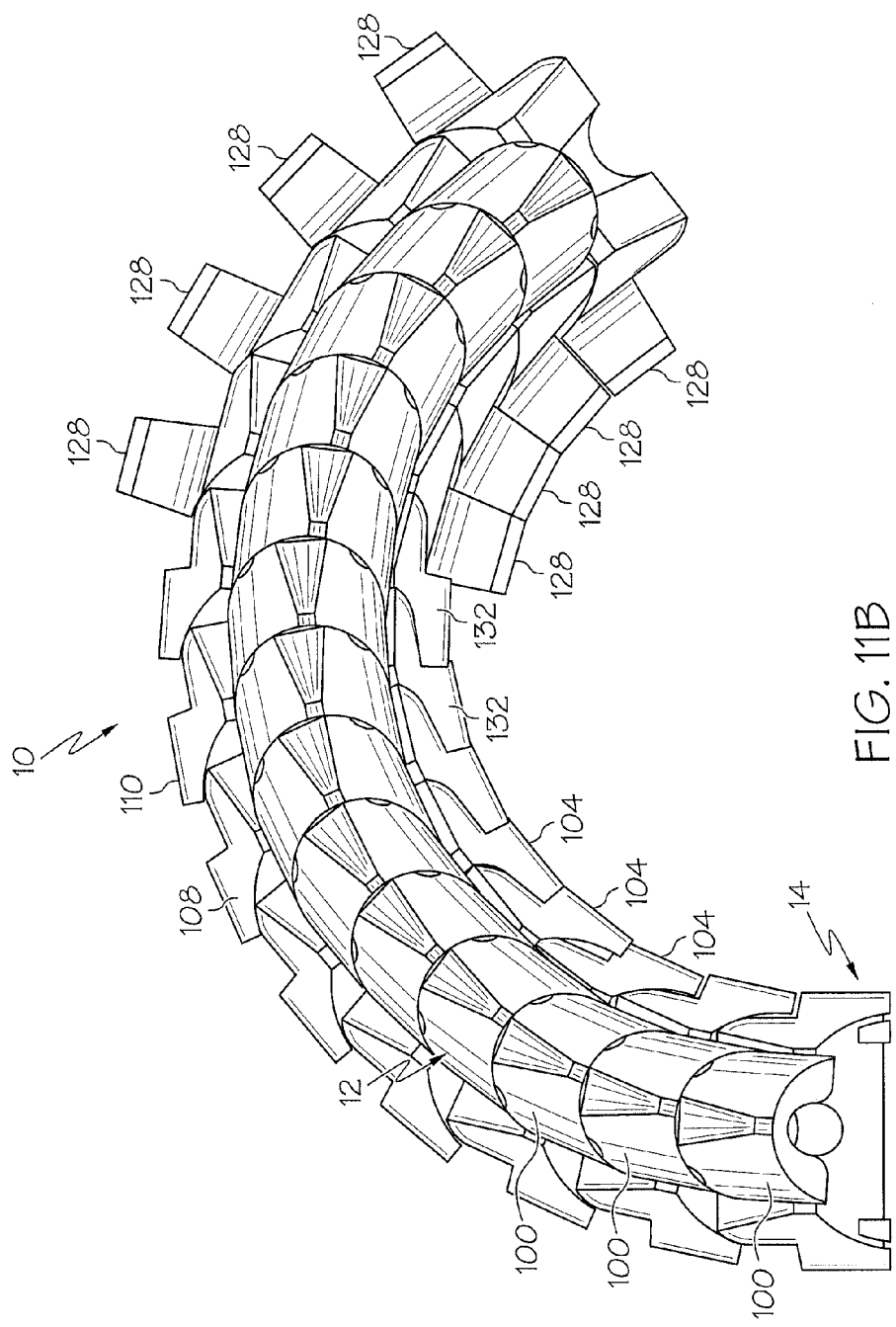

With regard to the outer links, FIGS. 14A-16J illustrate various views of presently preferred embodiments of such outer links 104, 132. These embodiments of the outer links are similar to those discussed in the overview above. However, these embodiments differ in some significant aspects from those discussed above, as well as from each other. The present embodiments of the outer links 104, 132 can be combined to form a unique outer sleeve 14, such as shown in FIG. 11A. In particular, FIGS. 16A-16K illustrate various views of outer links 104 with tool side ports 128. The tool side ports 128 can be used to receive and guide tools. FIGS. 15A-15J illustrate various views of transition outer links 132. As shown in FIG. 11A, a plurality of transition outer links 132 can be positioned adjacent an outer link 104 with tool side ports 128. The transition outer link 132 can have one or more recesses 130 that accommodates and funnels elongated members, such as tools, into the tool side port 128 of the outer link 104. For example, the inner diameter of the outer link 104, 132 preferably is in the range of 0.10-2.00 inches, and more preferably the inner diameter is approximately 0.394 inches. The outer diameter of the outer link 104, 132 preferably is in the range of 0.20-3.00 inches, and more preferably the outer diameter is approximately 0.669 inches. The outer link 104, 132 may be comprised, for example, of at least one of metals, plastics, glass, carbon fiber, etc. In a particular embodiment, the outer link 104, 132 is comprised, for example, of polyphenylsulfone (e.g., Radel® R-5100).

With regard to the inner links 100, FIGS. 17A-17I illustrate various views of presently preferred embodiments. These inner links 100 are similar to those discussed in the overview above. However, they differ in some significant aspects. The length of the inner link 100 preferably is in the range of 0.10-2.00 inches, and more preferably the length of the inner link 100 is 0.353 inches. The outer diameter of the inner link preferably is in the range of 0.01-2.00 inches, and more preferably, the inner diameter is 0.354 inches. The inner link 100 may be comprised, for example, of at least one of metals, plastics, glass, carbon fiber, etc. In a particular embodiment, the inner link 100 is comprised of plastic embedded with glass fiber (30% by weight).

The inner links 100 are configured to pivot relative to one another through a maximum pivot angle, and the outer links 104 are configured to pivot relative to one another through a maximum pivot angle, as shown for example in FIGS. 10A-13B. Preferably, the maximum pivot angle of the inner links 100 is no less than the maximum pivot angle of the outer links 104. In view of this pivoting relationship, it can be important for the links 100, 104 to be configured in such a way to avoid one or more undesired conditions such as: limiting the articulated probe 10 flexion; pinching of an elongated member that may be positioned within the links 100, 104; and problems that might occur with the advancement and retraction of the elongated member.

Figure 14A:
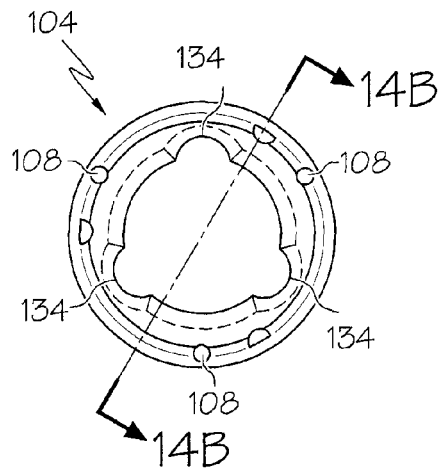
FIGS. 14A-14I illustrate various views of an outer link, according to an embodiment, in accordance with the present inventive concepts.
Figure 14B:
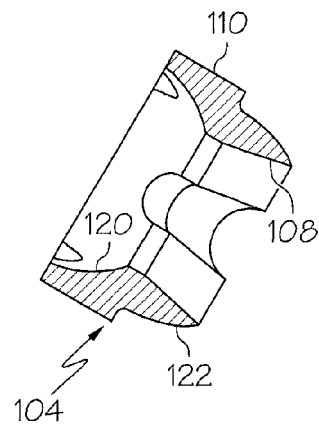
Figure 14C:
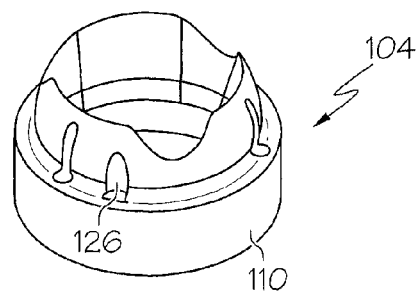
Figure 14D:
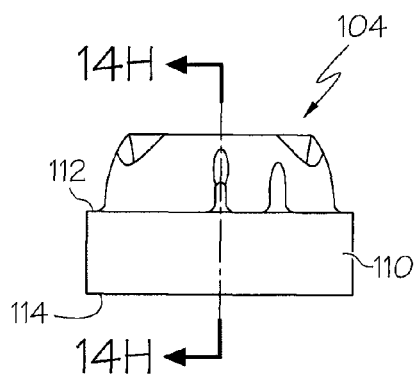
Figure 14E:
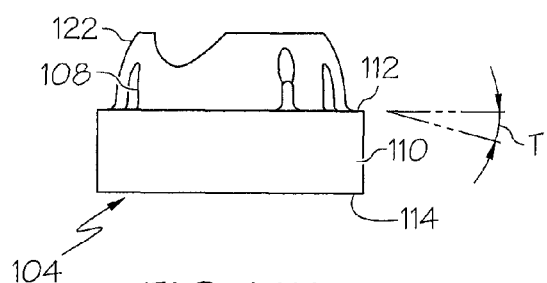
Figure 14F:
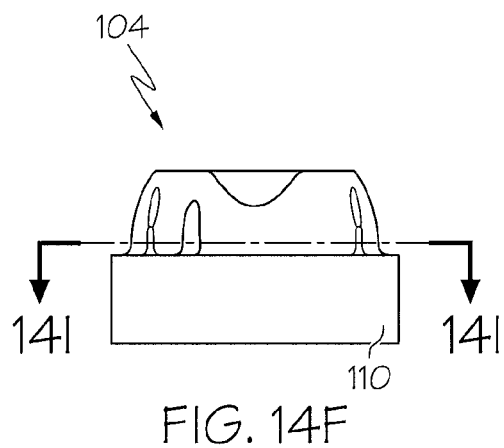
Figure 14G:
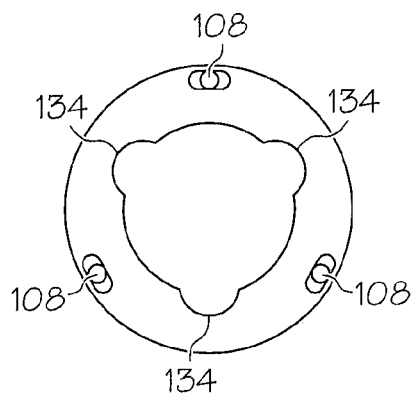
Figure 14H:
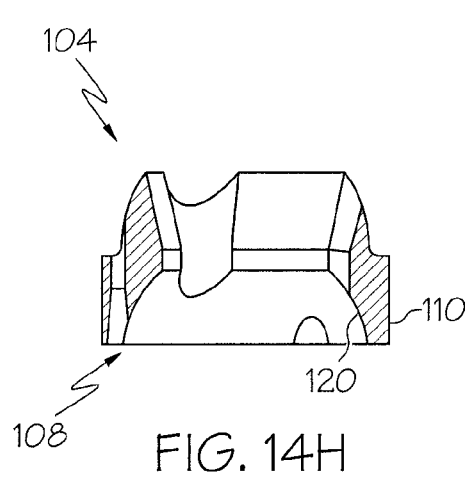
Figure 14I:
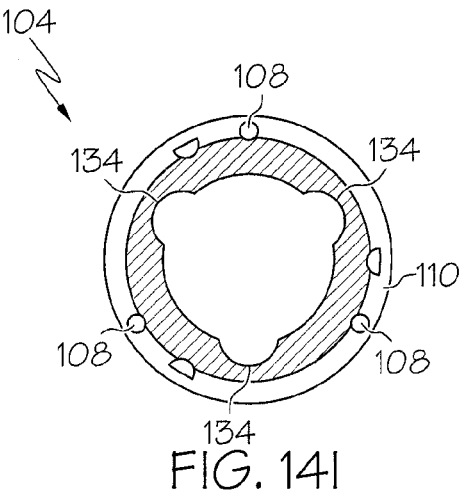
Figure 15A:
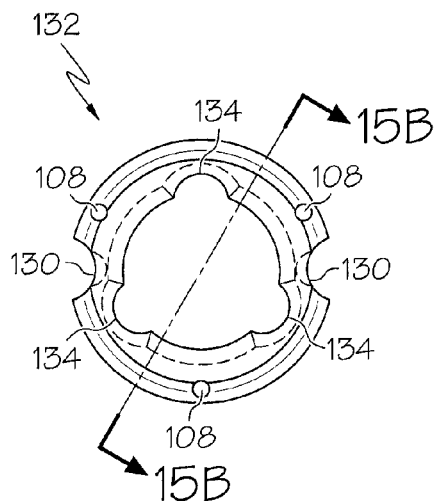
FIGS. 15A-15J illustrate various views of an outer link transition segment, according to one embodiment.
Figure 15B:
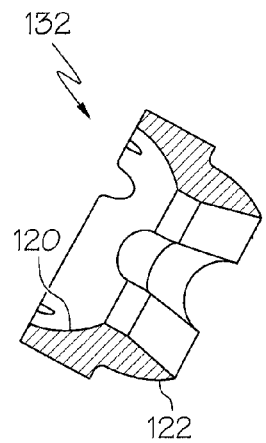
Figure 15C:
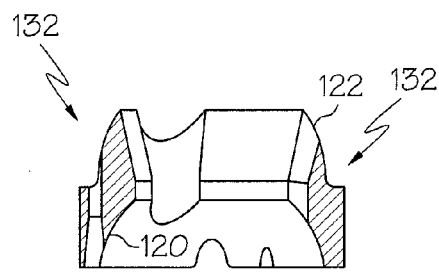
Figure 15D:
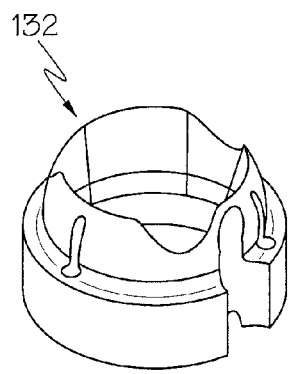
Figure 15E:
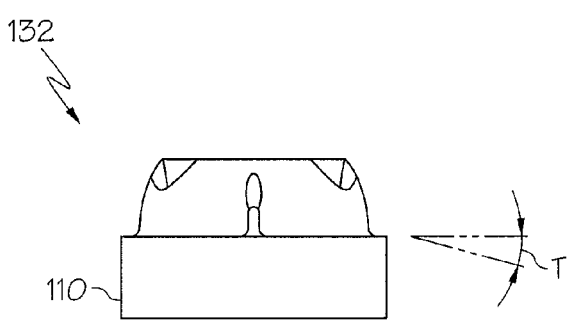
Figure 15F:
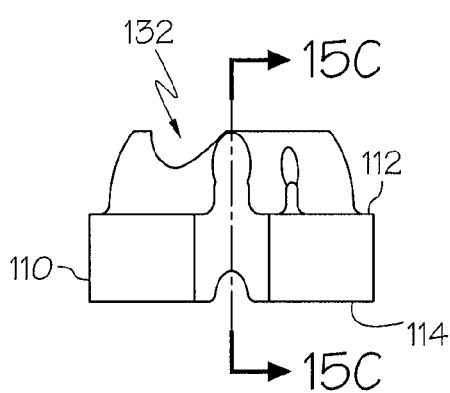
Figure 15G:
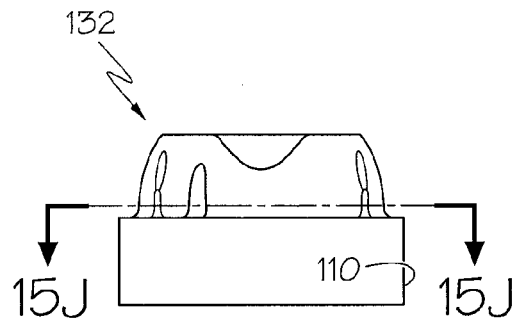
Figure 15H:
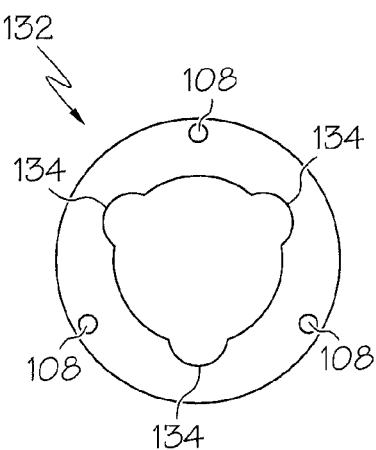
Figure 15I:
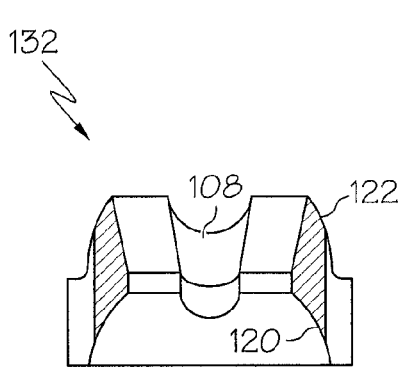
Figure 15J:
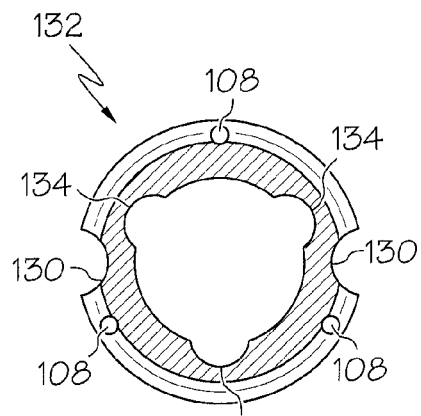
Figure 16A:
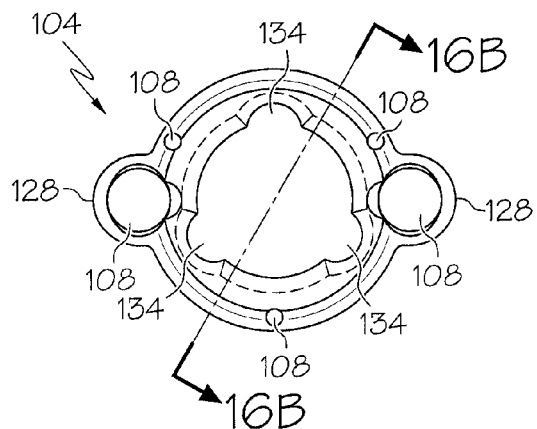
FIGS. 16A-16K illustrate various views of an outer link with tool side ports, according to an embodiment, in accordance with the present inventive concepts.
Figure 16B:
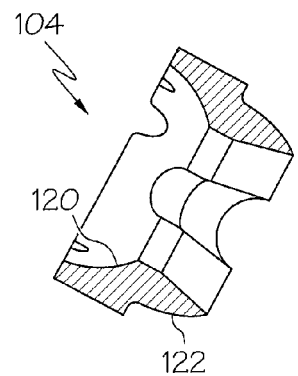
Figure 16C:
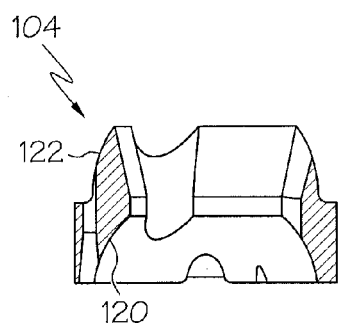
Figure 16D:
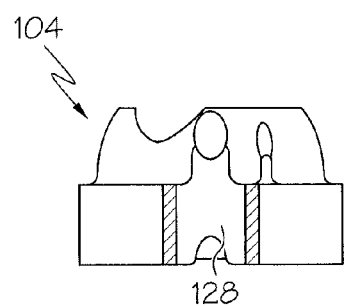
Figure 16E:
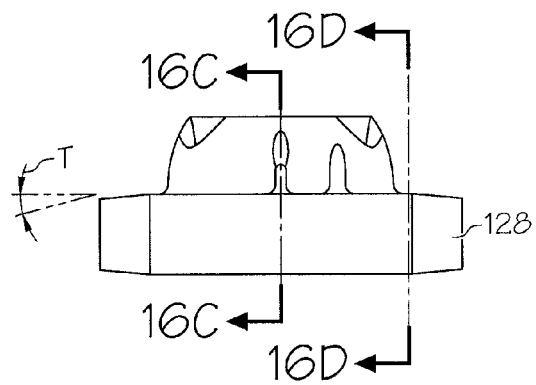
Figure 16F:
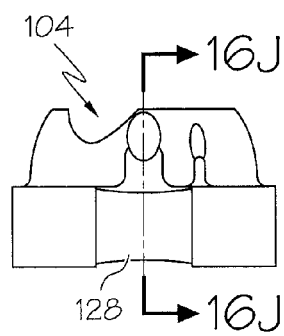
Figure 16G:
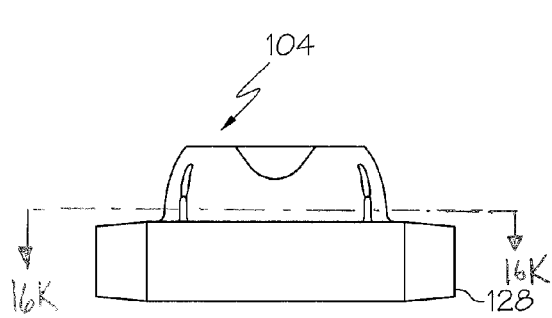
Figure 16H:
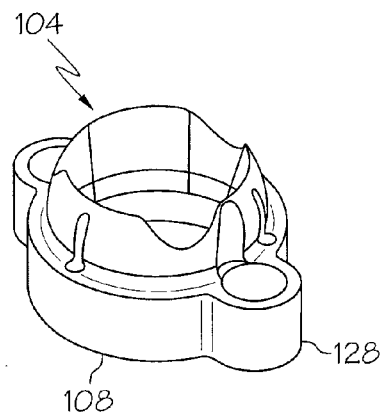
Figure 16I:
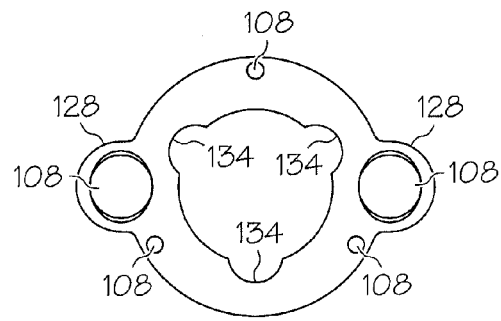
Figure 16J:
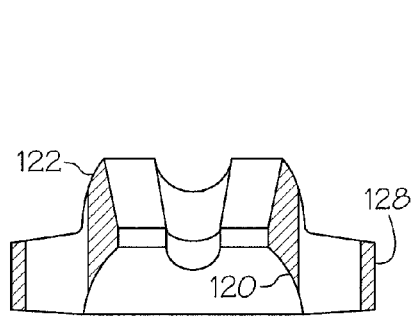
Figure 16K:
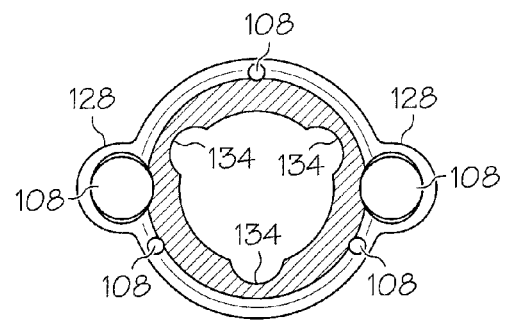
Figure 17F:
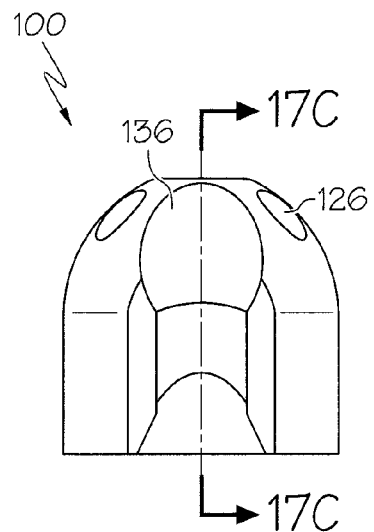
FIGS. 17 A-17I illustrate various views of an inner link, according to an embodiment, in accordance with the present inventive concepts.
Figure 17G:
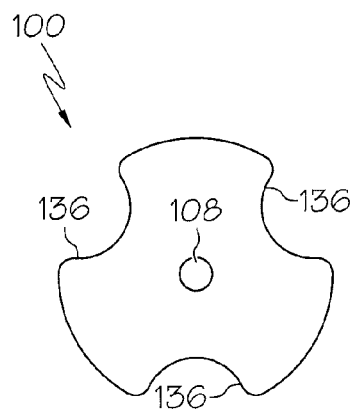
Figure 17H:
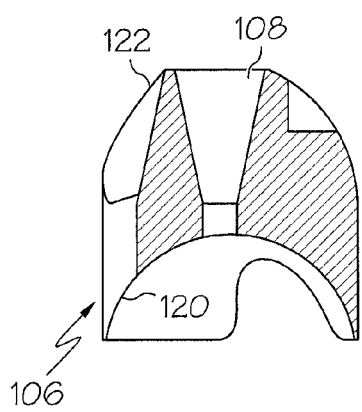
Figure 17I:
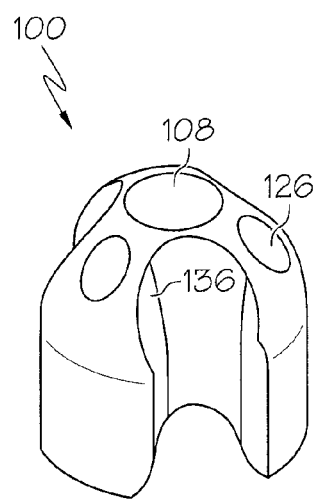
Figure 18:
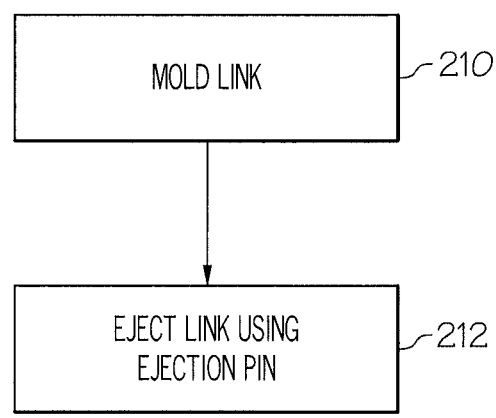
FIG. 18 is a flow chart for producing a link for an articulated probe according to an embodiment, in accordance with the present inventive concepts.

Each of the plurality of inner links 100 and/or outer links 104 may have one or more channels 108 for receiving an elongated member. Alternatively or additionally, mating recesses in inner links 100 and outer links 104 may create one or more channels between inner core 12 and outer sleeve 14. An elongated member may be any one of a tool, an inner cable 102, an outer cable 106, or an inner core 12. Typical elongate tools include but are not limited to: scissors, scalpels and other cutting tools; graspers such as tissue graspers; energy delivery elements such as tissue ablation elements, electrocautery and coagulation elements; cambers such as fiber optic cameras; heating elements; cooling elements; drug delivery devices; and combinations of these. As discussed in the overview, the tool can be used to perform various operations and one or more cables may be used to control the outer links 104 of the outer sleeve 14 and the inner links 100 of the inner core 12. The channels 108 are configured to form a semi-continuous passage from link 100, 104 to an adjacent link 100, 104 and can include a liner to facilitate reception of the elongated member. As shown in FIG. 14G, the channel 108 may have a circumferential flare. The circumferential flare avoids pinching elongated members within the channel 108 and facilitates rotation of the plurality of links 100, 104 while significantly reducing any difficulty that may be encountered by advancing or retracting an elongated member through the probe 10. Further, the channels 108 of inner links 100 and/or outer links 104 may be tapered to achieve a semi-continuous passage from link 100, 104 to link 100, 104.

According to one embodiment, the channel 108 in each of the inner links 100 and/or outer links 104 is tapered in an amount sufficient to permit the inner links 100 and/or outer links 104 to pivot through the maximum pivot angle while providing a substantially continuous surface between the channels 108 of the links 100, 104 for receiving the elongated member. More preferably, the opening and/or exit of the channel 108 can be tapered. The tapered openings and exits of the channel 108 avoid pinching elongated members within the channel 108 and significantly reduce any difficulty that may be encountered by advancing or retracting an elongated member through the probe 10. In addition, the tapered openings correlate to the radius of curvature of the probe. According to one embodiment, the taper of the channel 108 is approximately twice the maximum pivot angle. For example, the taper can be approximately 26° degrees and the maximum pivot angle can be approximately 13° degrees. The taper of the channel 108 preferably can accommodate a pivot angle of 13° degrees or greater. In sum, the tapered channels 108 are configured to provide a substantially continuous surface between the channels 108 of the links 100, 104 for the reception of the elongated member.

The inner links 100 of the inner core 12 may have the channel 108 positioned near a central axis and configured to receive an inner cable 102 (the elongated member), as shown in FIGS. 13A-B and 17A-17I. The channel 108 within the inner links 100 can have a flared opening. According to one embodiment, the flared opening is positioned off-center in relation to the central axis of the inner link 100. Positioning the flared opening off-center allows the pivot point of the inner cable 102 to change more easily when the pivot point of the inner core 12 may change due to rotation of the inner core 12 or any other form of translational displacement that may occur. Preferably, the diameter of the channels 108 of the inner links 100 is greater than the diameter of the inner cable 102, which reduces the occurrence of twisting and sawtoothing of the inner links 100. For example, if the channel 108 preferably has a diameter in the range of 0.003-0.500 inches (more preferably approximately 0.043 inches), the diameter of the inner cable 102 preferably is in the range of 0.002-1.000 inches (more preferably approximately 0.037 inches). By configuring the diameter of the inner cable 102 and channel 108 of the inner links 100 to reduce twisting and sawtoothing, the likelihood of pinching or difficulty with advancement and retraction of the elongated member is also significantly reduced. Thus, the channel 108 of the inner link 100 provides a substantially continuous surface between links 100 for the inner cable 102.

Figure 12A:
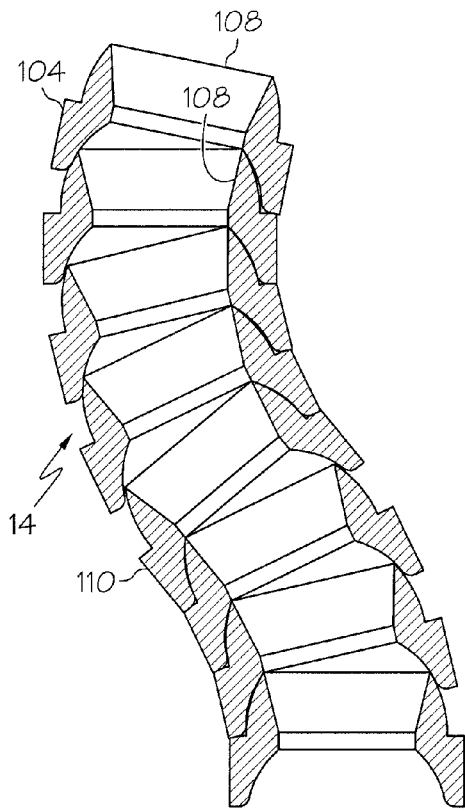
FIGS. 12A-12B illustrate a cross section of an outer sleeve according to an embodiment, in accordance with the present inventive concepts.

The outer links 104 of the outer sleeve 14 also may have the channel 108 formed therein for the reception of an elongated member, as shown for example in FIG. 12A. In this particular embodiment, the elongated member can be an inner core 12 with a plurality of inner links 100. The channel 108 is positioned within a plurality of outer links 104, each having a flared opening. As shown in FIG. 12A, the flared opening in each of the plurality of links 104 provide a substantially continuous surface between links 104 for reception of the inner core 12. The channels 108 of the outer links 104 are also tapered in an amount sufficient to permit an inner core 12 to pivot through a maximum pivot angle while providing a substantially continuous surface between the channels 108 for the inner core 12. The taper of the channels 108 also allows flexion of the inner links 100. Preferably, the inner flexion of the inner links 100 may be greater than or equal to 13° degrees. Thus, the channel 108 of the outer link 104 provides a substantially continuous surface between links 104 for the reception of the inner core 12.

A plurality of channels 108 also may be positioned near the outer surface of the outer link 104, as shown in FIGS. 14A-16K. According to one embodiment, three channels 108 are positioned approximately 120° degrees from each other around a circumference of one or more outer links 104 making up the outer sleeve 14. The channels 108 of the outer link 104 are configured to receive an elongated member in the form of outer cables 104 for controlling the outer sleeve 14. In one embodiment, a diameter of the outer cables 106 is less than a diameter of the channels 108 of the outer links 104, which reduces the occurrence of twisting and sawtoothing of the outer links 104. According one embodiment, the diameter of the outer cables 106 may be in the range of 0.002-1.000 inches, more preferably, the diameter of outer cables 106 is 0.027 inches. The diameter of the channels 108 in each outer link 104 for receiving the outer cables 106 may be in the range of 0.003-0.500 inches. In a particular embodiment, the diameter of the channels 108 in each outer link 104 are approximately 0.035 inches. By configuring the diameter of the outer cables 106 and channels 108 of the outer links 104 to reduce twisting and sawtoothing, the likelihood of pinching or difficulty with advancement and retraction of the elongated member is also significantly reduced. Thus, the channels 108 of the outer link 104 provides a substantially continuous surface between links 104 for the plurality of cables 106.

A combination of the inner link 100 and the outer link 104 also may be configured so as to provide the channel 108 for receiving an elongated member. With reference to FIGS. 14A-14I, an inner surface of the outer link 104 can have a flared indentation 134 which forms one half of a channel 108 for receiving an elongated member in the form of a tool. As shown in FIGS. 17A-17I the other half of the channel 108 is formed by flared indention 136 on the outer surface of the inner link 100. The channel 108 formed by the flared indention 136 of the inner link 100 and the flared indention 134 of the outer link 104 provides a substantially continuous surface between links 100, 104 for one or more tools.

The outer links 104 and 132 shown in FIGS. 15A-16K can both be configured to receive an elongated member in the form of a tool, cable, or other elongated device. With respect to FIGS. 11A and 16A-16K, the channels 108 of an outer link 104 can be formed by tool side ports 128. The tool side ports 128 extend out from the outer circumference of the outer link 104 and are configured with a channel 108 to receive tools, cables, or other elongated devices. As shown in FIG. 11A, the transition outer link 132 is positioned between an outer link 104 and an outer link 104 with tool side ports 128 along the length of the probe 10. According to one embodiment and as shown in FIGS. 15A-15J, the transition outer link 132 has one or more recesses 130 that accommodates and funnels tools into an outer link 104 having a tool side port 128. Accordingly, tools configured for use approximately outside the circumference of the probe 10 can be received by the channels 108 formed by the tool side ports 128 and the recesses 130 of the transition outer link 132. The channels 108 formed by the tool side ports 128 and the recesses 130 provides a substantially continuous surface between the outer links 104, 132 for one or more elongated devices.

The radius of curvature of the articulated probe 10 can depend on the pivot angle of the inner and outer links 100, 104. With respect to FIGS. 10A-12B and 14A-I, the outer sleeve 14 may include a plurality of outer links 104 having an outwardly extending flange 110. The flange 110 is configured to control the pivot angle of the outer links 104 relative to one another. Thus, characteristics of the flange 110 impact the radius of curvature of the articulated probe 10 that can be achieved.

According to one embodiment, the geometry of the flange 110 determines the degree of pivot possible between each of the outer links 104. With respect to FIGS. 14D-14E, the flange 110 can have a first engagement surface 112 and a second engagement surface 114 extending radially outward relative to a first central axis of the outer link 104. The flange 110 is configured to permit the outer links 104 to pivot relative to one another and a probe central axis through an outer maximum pivot angle until the first engagement surface 112 of a first outer link 104 and the second engagement surface 114 of a second outer link contact each other. According to one embodiment, the first engagement surface 112 and the second engagement surface 114 taper at an angle T relative to a line perpendicular to a central axis of the outer link 104. With reference to FIG. 14E, in one particular embodiment, the first engagement surface 112 tapers approximately 6.5° degrees and the second engagement surface 114 tapers approximately 6.5° degrees. According to this embodiment, the outer maximum pivot angle is no greater than approximately 13° degrees. In alternative embodiments, the taper of the first engagement surface 112 and the second engagement surface 114 may be configured so that the maximum pivot angle is greater than 13° degrees, or less than 13 degrees. Preferably, the geometry of the flange 110 is configured so that the radius of curvature of the articulated probe 10 is in the range of 10-600 mm. Thus, the geometry of the flange 110 can be used to set the maximum pivot angle of the outer links 104, which in turn impacts a range of the radius of curvature of the articulated probe 10.

The links 100, 104, 132 can be configured to reduce the occurrence of irregular or undesired forces (e.g., irregular or undesired frictional engagement forces) acting between a first and second link 100, 104. For example, as shown in FIGS. 14B, 14H, 15B, 15C, 15I, 16B, 16C, 16J, 17C, 17D, 17H, the plurality of inner links 100 and outer links 104 may include a first concave portion 120 and a first convex portion 122. A convex portion 122 of a first link 100, 104 can pivotally engage a corresponding concave portion 120 of a second link 100, 104. According to a particular embodiment, the first link 100, 104 convex portion 122 has a radius of curvature no greater than a radius of curvature of the second link 100, 104 concave portion 120. The links 100, 104 can be linked together to form an inner core 12 and outer sleeve 14. The arrangement of the links 100, 104 (a concave portion 120 pivotally engaging a corresponding convex portion 122) allows the inner core 12 and outer sleeve 14 to pivot with a wide range of motion and reduces the occurrence irregular or undesired frictional or other forces between links 100, 104 that may interfere with efficient operation of the articulated probe 10.

As demonstrated above, the physical characteristics of the various features of the inner core 12 and outer sleeve 14 affect the properties and performance of the articulated probe 10 in various ways. According to one embodiment, the geometric dimensions of one or more channels of an outer link 104 are mathematically related to one or more parameters of outer link 104. These parameters may include: the radius of an end of outer link 104; the diameter of outer link 104; the pivot angle between outer links 104; diameter of the channel such as average diameter of the channel; the channel location such as the distance of the channel from a central axis of outer link 104.

It can be advantageous to form the links in a way that facilitates smooth articulation of one link relative to the other and avoids undesired mating forces such as irregular frictional engagement between adjacent links. With respect to FIGS. 17A, 17B, 17D-17F, 17I and 18 a method for producing a link 100, 104 for an articulated probe 10 will now be described. In step 210, the link 100, 104 is molded in a molding device, including forming at least one engagement surface configured to engage an adjacent link 100, 104 in the articulated probe 10. In step 212, the link 100, 104 is ejected from the molding device by pressing at least one ejection pin, 124 (see FIG. 17E) against an ejection surface 126 of the link 100, 104 that will not engage an adjacent link 100, 104 in the articulated probe 10. As shown in FIGS. 17A, 17B, 17D-E and 17I, according to one embodiment, the ejection surface 126 is located in a recess in the link 100, 104. Strategically positioning the ejection surface 126 on a link 100, 104 ensures that the ejection surface 126 does not affect the interaction of one link 100, 104 with another such as by positioning any ejection pin imperfections away from the mating surfaces between adjacent links. Thus, the above-described procedure ensures that each link 100, 104 articulates smoothly relative to another link 100, 104.

Cables

Figure 12B:
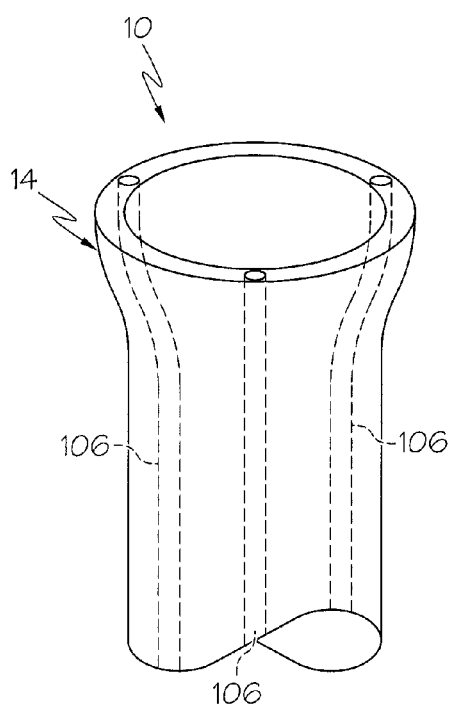

As discussed in the overview above, one or more cables may be used to control the outer links 104 of the outer sleeve 14 and the inner links 100 of the inner core 12. Further examples of cable configurations of cables are described below. In these configurations, as shown in FIG. 12B, a plurality of outer cables 106 can extend through the plurality of outer links 104. The outer cables 106 are configured to control (e.g. steer and transition between flexible and rigid) the outer sleeve 14. In an embodiment, each of the plurality of outer cables 106 has approximately the same tensile strength and/or approximately the same cross-sectional area.

Figure 13B:
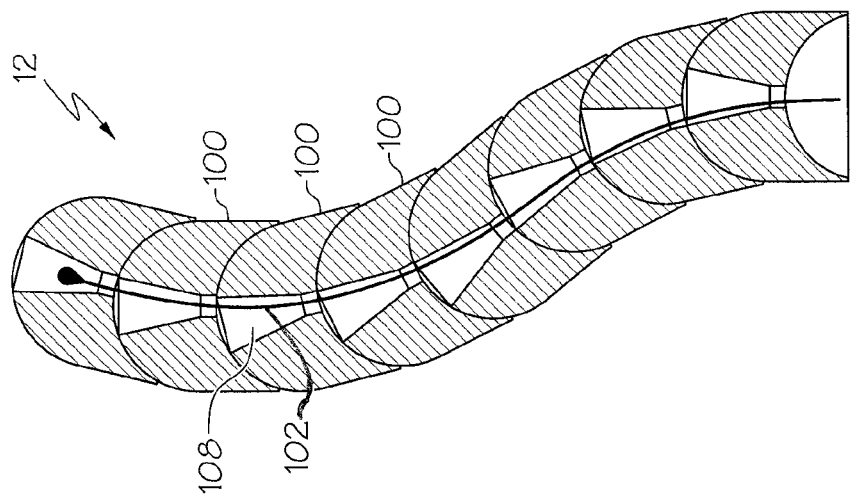
FIGS. 13A-13B illustrate a cross section of an inner core according to an embodiment, in accordance with the present inventive concepts.
Figure 13A:
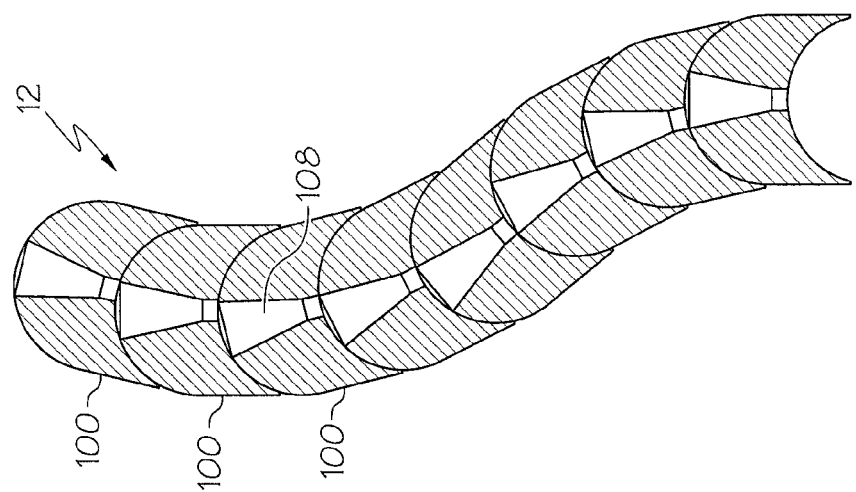

As shown in FIGS. 13A-13B, an inner cable 102 extends through the plurality of inner links 100. The inner cable 102 is configured to control the inner core 12 (e.g. transition between flexible and rigid). In an embodiment, the tensile strength and/or cross sectional area of the inner cable 102 is related to the tensile strength and/or cross sectional area of the plurality of outer cables 106.

The relationship between the tensile strength and/or cross sectional area of the inner cable 102 and the plurality of outer cables 106 provide for efficient movement and operation of the articulated probe 10. With regard to tensile strength, the inner cable 102 can have a tensile strength greater than each of the individual outer cables 106. In some embodiments, the tensile strength of the inner cable 102 is approximately equal to a combined tensile strength of the plurality of outer cables 106. In some embodiments, the tensile strength of each of the plurality of outer cables 106 is approximately 1/Nth of a tensile strength of the inner cable 102, where N is the number of outer cables 106. For example, the tensile strength of the inner cable 102 and the combined tensile strength of the outer cables 106 can be in the range of 2-500 lbs, and, in some embodiments, is about 30 pounds.

With regard to cross-sectional area, the cross-sectional area of each of plurality of outer cables 106 can be approximately 1/Nth of a cross-sectional area of the inner cable 102, where N is the number of outer cables. This relationship is particularly, though not exclusively, important in a configuration where the cables 102, 106 are formed of the same material and/or when the probe diameter is minimized.

The material forming the inner and outer cables 102, 106 can impact the configuration of the cables. The inner cable 102 and the plurality of outer cables 106 may be comprised of the same material, which, in some embodiments, can be at least one of steel, polyethylene (UHMW-ultra-high-molecular-weight), plastic, nylon and fluorocarbons, with steel being more preferred in some embodiments. The inner cable 102 and the plurality of outer cables 106 can be formed from by a monofilament or braided technique. However, the desired tensile strength relationships can also be achieved by using different materials for the inner cable 102 and the outer cables 106.

In sum, the inner cables 102 and outer cables 106 used to control the inner core 12 and outer sleeve 14 can have various characteristics. These characteristics include, but are not limited to the tensile strength, the cross-sectional area and the composition of the cables 102, 106. Configuring the cables based on desired characteristics and relationships with respect to the inner cable 102 and the outer cables 106 determine the stability and other performance parameters of the articulated probe 10.

While the preferred embodiments of the devices and methods have been described in reference to the environment in which they were developed, they are merely illustrative of the principles of the inventive concepts. Modification or combinations of the above-described assemblies, other embodiments, configurations, and methods for carrying out the invention, and variations of aspects of the inventive concepts that are obvious to those of skill in the art are intended to be within the scope of the claims. In addition, where this application has listed the steps of a method or procedure in a specific order, it may be possible, or even expedient in certain circumstances, to change the order in which some steps are performed, and it is intended that the particular steps of the method or procedure claim set forth here below not be construed as being order-specific unless such order specificity is expressly stated in the claim.

Introduction Device

An introduction device 330, such as that shown in FIGS. 19-27, can be configured to support, stabilize and guide an articulated probe, such as the articulated probe 10 described above, to a region of interest. The region of interest may be a lumen, a patient's body, a mechanical device, a building, or any other open or closed environment in which the probe 10 can be used. In clinical applications, typical regions of interest include but are not limited to: the esophagus and other locations within the gastrointestinal tract; the pericardial space; the peritoneal space; and combinations thereof.

Figure 24:
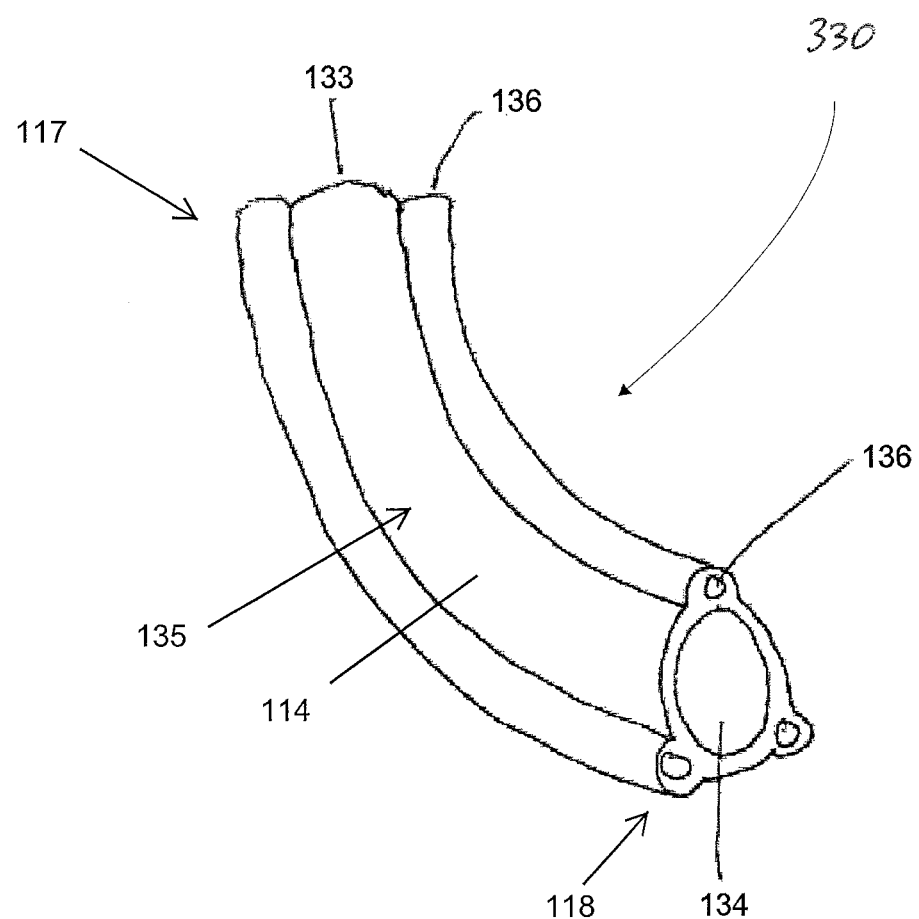
FIG. 24 illustrates a perspective view of an embodiment of an introduction device, in accordance with the present inventive concepts.

As shown in FIG. 24, the introduction device 330 includes hollow tube 114, which includes a lumen or other hollow passageway that is surrounded by luminal walls forming a support member 135. The lumen and support member 135 extend between an entrance 133 positioned at a proximal end 117 and an exit 134 positioned at a distal end 118. The introduction device 330 can be configured to improve access to regions of interest and provide for fast, safe and/or accurate advancement of the articulated probe 10.

The entrance 133 of the introduction device 330 is configured to receive an articulated probe 10. The entrance 133 guides the articulated probe 10 so that the articulated probe 10 comes into close proximity or contact with the support member 135. For example, the entrance 133 may guide an articulated probe 10 from a feeding mechanism 16 into proximity with the support member 135. Accordingly, the entrance 133 guides the articulated probe 10 into the introduction device 330 and into proximity with the support member 135.

Figure 22:
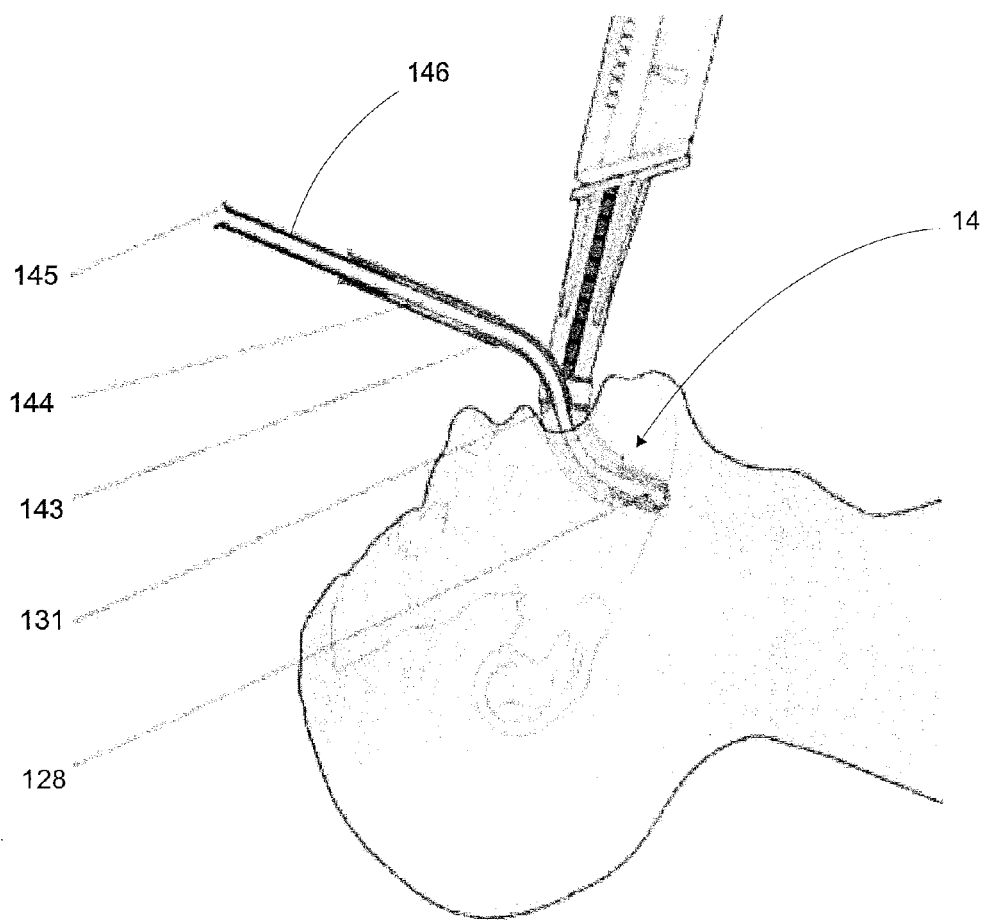
FIG. 22 illustrates a side cross-sectional view of an embodiment of an introduction device having a tool port and attached to a feeding mechanism, in accordance with the present inventive concepts.

The exit 134 of the introduction device 330 is configured to receive the articulated probe 10 from the lumen of introduction device 330. In addition, the exit 134 introduces the articulated probe 10 into a region of interest. For example, the exit 134 may guide the articulated probe 10 from the introduction device 330 into a region of interest such as a body lumen, an esophagus as shown in FIG. 22, a subxiphoid space, a colon, or an intracranial space. Thus, the exit 134 facilitates introduction of the articulated probe 10 into a region of interest.

The support member 135 can have any configuration that is capable of supporting or otherwise resisting movement of an articulated probe 10. For example, the support member 135 can be either rigid or flexible. In an example embodiment where the support member is rigid, the support member 135 may be formed from a rigid material, such as machined metal or molded plastic. In an example embodiment where the support member is flexible, the support member 135 may be formed from one or more flexible materials and can include one or more internal malleable members configured to plastically deform so as to maintain an operator formed shape of introduction device 330 or a portion thereof. In other embodiments, the support member can be configured so as to be elastically deformable.

Several possible configurations of the support member 135 are shown in FIGS. 20-27. The support member 135 can be an axially curved member as shown, for example, in FIGS. 20-27. Alternatively, the support member 135 may be a straight or substantially straight member (not shown). According to one embodiment, the support member 135 has a cylindrical shape, such as a hollow tube 114. As shown in FIG. 24, the cylindrical shaped support member 135 has an internal diameter. The internal diameter of the support member 135 is larger than the outer diameter of the articulated probe 10. Preferably, the support member 135 diameter is determined by the following formula:

$$ID \geq l_2 + R_1 - R_1 \cos\left[\sin^{-1}\left[\frac{l_1}{2R_1}\right]\right]$$

where $l_1$ is the segment length, $l_2$ is the segment diameter, and $R_1$ is the inner radius of the introducer.

In some embodiments, the introduction device 330 can have an outer diameter that is smaller than the diameter of an opening of the region of interest in which the probe 10 will be used.

According to one embodiment and as shown in FIGS. 20-23, the support member 135 can be formed from two opposed and elongated curved surfaces 115a, 115b separated by gap 116. In some embodiments, the concave side of one curved surface 115a opposes the concave side of the other curved surface 115b so that, in combination, the curved surfaces 115a, 115b encompass, or otherwise partially surround and guide the articulated probe 10. Alternatively, a single, elongated curved surface may be used. The support member 135 may have a collar 131 disposed circumferentially about the two elongated curved surfaces 115a, 115b so as to secure the two elongated curved surfaces 115a, 115b, and maintain them at a desired distance apart from each other, and thereby control the width of the gap 116 and the internal diameter of support member 135. The collar 131 can use an interference fit to remain attached to the two elongated curved surfaces 115a, 115b or it may be attached using a fastener or an adhesive. Introduction device 330 may include one or more side channel tool ports 141, constructed and arranged to receive a tool shaft or a guide tube for a tool shaft. Side channel tool ports may be similar or dissimilar (e.g. different diameters, stiffnesses, etc), such as to accommodate similar or dissimilar tools and/or tool shafts. Collar 131 may be rotatably attached to support member 135 such as to allow repositioning of tools passing through the side channel tool ports 141. Collar 131 may be rotatably attached to support member 135 such as to allow one, two, or more, degrees of freedom of rotation of tool ports 141. In one embodiment, collar 131 provides a single degree of freedom, rotating about the outer diameter of introduction device 330.

Figure 26:
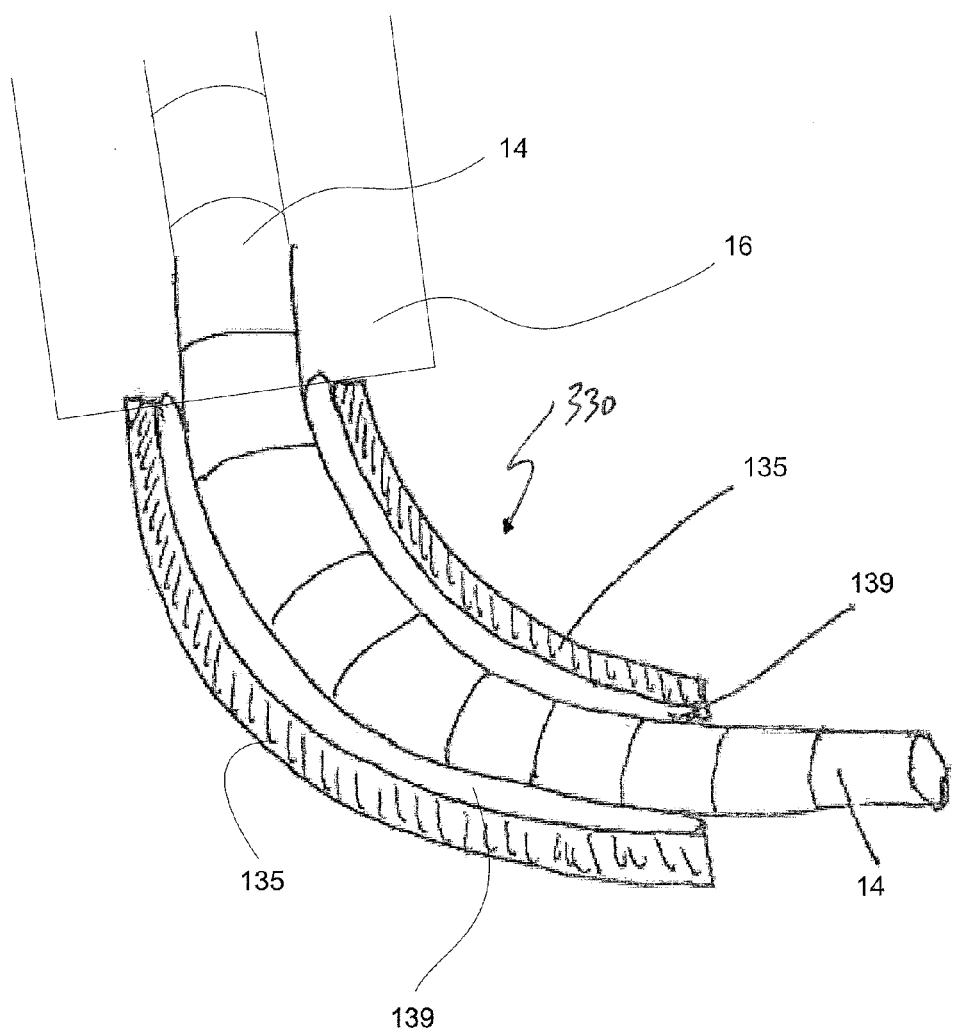
FIG. 26 illustrates a side perspective view of an embodiment of an introduction device, in accordance with the present inventive concepts.

According to one embodiment as shown in FIG. 26, a clamp 139 is located on support member 135. The clamp 139 further minimizes potential motion of articulated probe 10 and thus further stabilizes the articulated probe 10 as it is positioned within a region of interest. The clamp 139 may be any clamp that can be located proximate articulated probe 10 and/or support member 135 such as to limit motion of probe 10, such as when a force is applied to a distal portion of probe 10. Clamp 139 may be of various forms including a lever, a cam, an expandable member such as a balloon; a piston such as a hydraulic or pneumatic piston; an electromagnetically activated actuator such as a solenoid; and combinations of these. Clamp 139 can be configured to apply a force on a portion of outer sleeve 14 such as a force applied to an area of at least 1 mm², at least 10 mm² or at least 100 mm². In some embodiments, the clamp 139 comprises a balloon that can be controllably expanded and contracted, such as via one or more controls, not shown but preferably on a proximal portion of probe 10, feeder mechanism 16, and/or a control unit for probe 10. Delivery or removal of one or more fluids (e.g. air), such as through an inflation lumen, not shown but in fluid communication with clamp 139, can causes expansion and contraction, respectively, of clamp 139. When the balloon is in its expanded state, the outer surface of the balloon exerts pressure on the outer surface of the articulated probe 10. This minimizes the ability of the articulated probe 10 to move both radially and axially relative to the support member 135, stabilizing probe 10 within the introduction device 330. Alternatively or additionally, clamp 139 may be constructed and arranged to minimize the ability of the articulated probe 10 to rotate relative to the support member and/or introduction device 330. Stabilization of probe 10 may be of particular importance when manipulating the distal portion of probe 10 within a body cavity such as the esophagus. Stabilization of probe 10 may also be of particular importance when manipulating one or more tools passed through or alongside probe 10, such as when a tool applies a force to a tissue surface such as the esophageal wall of a patient. Accordingly, the support member 135 is configured to support and guide an articulated probe 10 both during advancement to one or more regions of interest as well as and thereafter such as during tool manipulation.

As shown in FIG. 24, the introduction device 330 may have at least one channel 136 that extends along the longitudinal axis of the support member 135. The channel 136 can be integral with an outside wall of the hollow tube 114 of introduction device 330. The channel 136 is configured to allow a filament 202*a*, not shown but described in reference to FIG. 25, such as a tool shaft guide tube or a tool shaft, to pass through the channel 136. Accordingly, filament 202*a*, and tools attached thereto, can also be introduced into a region of interest via the introduction device 330. Introduction device 330 may be rigid, flexible, or include both rigid and flexible portions. Introduction device 330 may include a malleable, or plastically deformable, member (not shown), which can be configured to allow introduction device 330 to be bent, twisted or otherwise reshaped such that the new configuration is maintained by a supporting force of the malleable member. In one embodiment, introduction device 330 has a corrugated construction permitting flexing while maintaining one or more internal lumen diameters.

Figure 19:
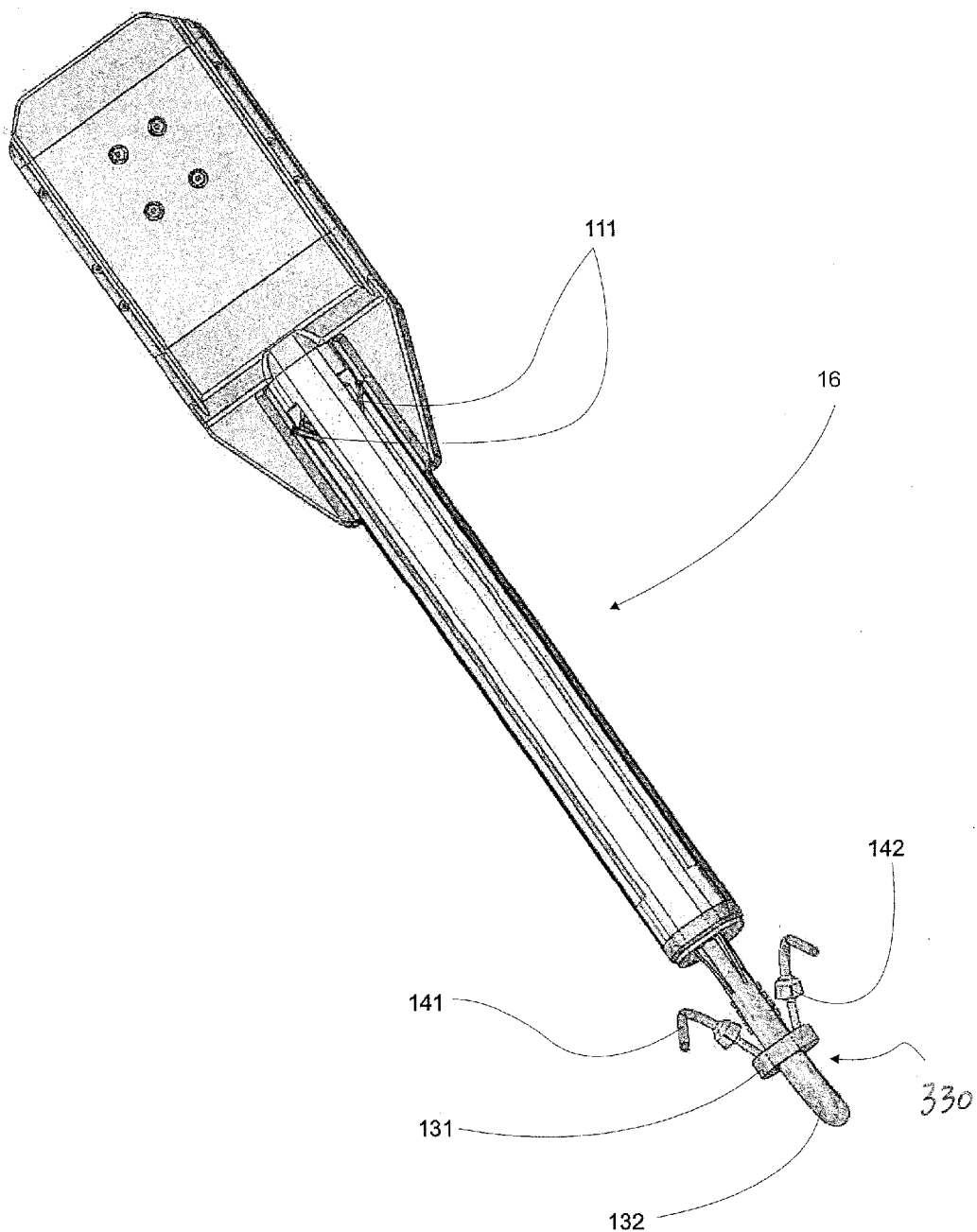
FIG. 19 illustrates a top view of an embodiment of the introduction device attached to a feeding mechanism, in accordance with the present inventive concepts.
Figure 20:
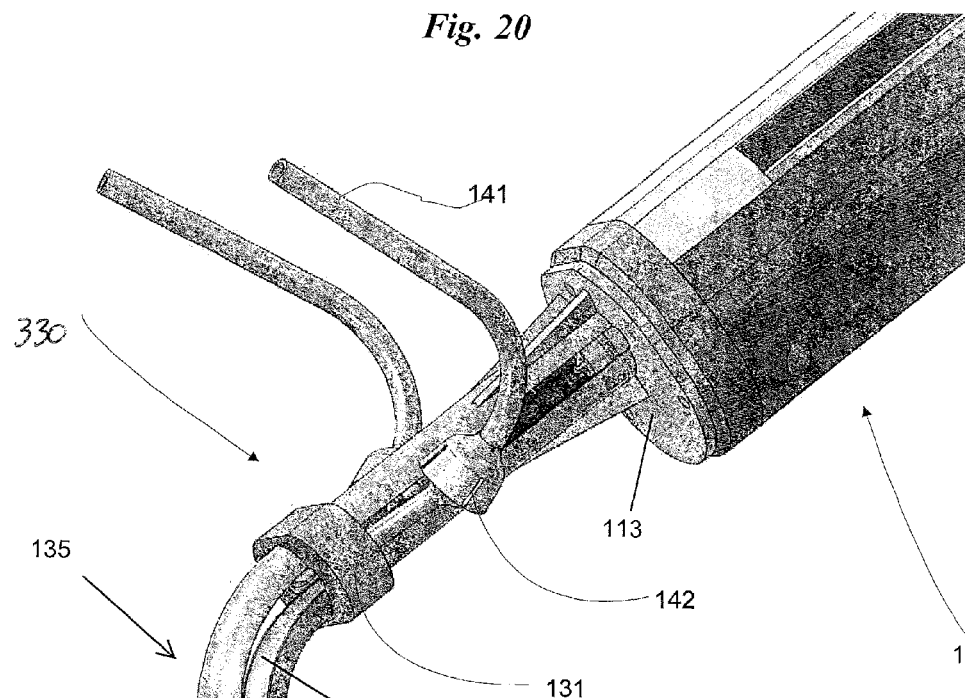
FIG. 20 illustrates a side perspective view of the embodiment of the introduction device illustrated in FIG. 19, in accordance with the present inventive concepts.
Figure 21:
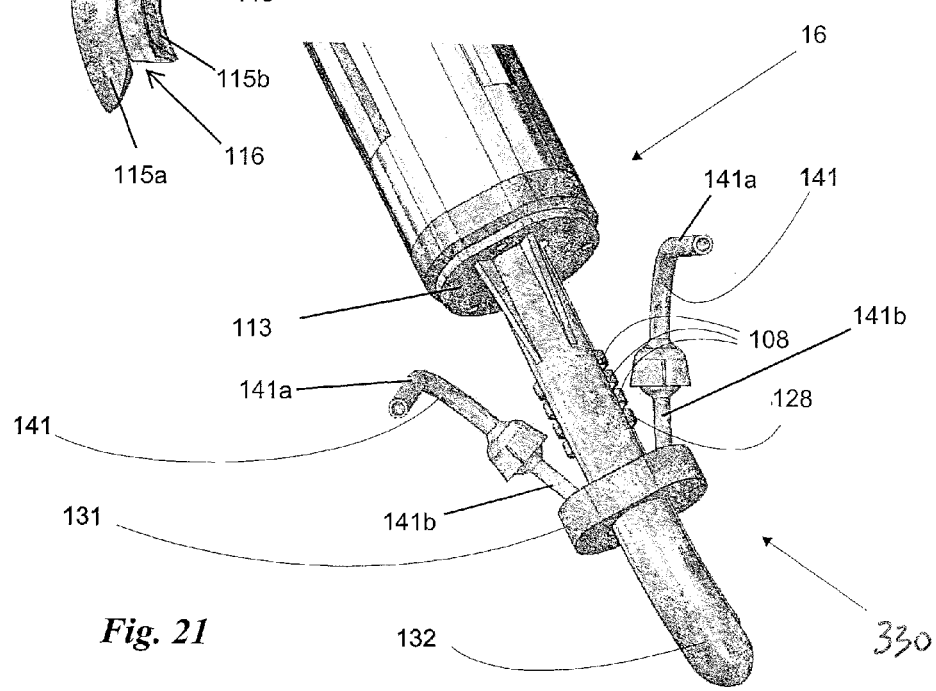
FIG. 21 illustrates a view of the embodiment of the introduction device illustrated in FIG. 19, in accordance with the present inventive concepts.

The introduction device 330 may include several configurations for guiding a filament 202*a* (see FIG. 25) such as a tool guide tube or a tool shaft, to a tool side port 128 located on a distal portion of articulated probe 10. As shown in FIGS. 19-21, the introduction device 330 may include a side channel tool port 141. As shown in FIG. 22, the introduction device 330 may include multiple coaxial tubes including tool tube 143*a*, 143*b* which slidingly receives, or otherwise communicates with, tube 144. In some embodiments, tool tube 143*a*, 143*b* is more rigid than tube 144 such that tube 144 flexes and tool tube 143*a*, 143*b* remains relatively rigid when a tool shaft or other filamentous device that has been inserted into tube 144, has a load applied to it.

FIGS. 19-21 depict an embodiment in which the side channel tool port 141 comprises a first section 141*a* and a second section 141*b*. A joint 142 is positioned between the first section 141*a* and the second section 141*b*. Preferably, the joint 142 is a spherical joint, a hinged joint, or combinations thereof. Alternatively or in addition to joint 142, first section 141*a* and/or second section 141*b* may be flexible or deformable, or may include flexible or deformable sections. The joint 142 allows rotation, or articulation, of the first section 141*a* relative to the second section 141*b*. Rotation of the first section 141*a* may also allow the corresponding tool 201*a*, 201*b* (see FIG. 25) to rotate, such as to allow an operator to position or reposition the proximal end of a tool without positioning or repositioning introduction device 330 or outer sleeve 14.

Figure 23:
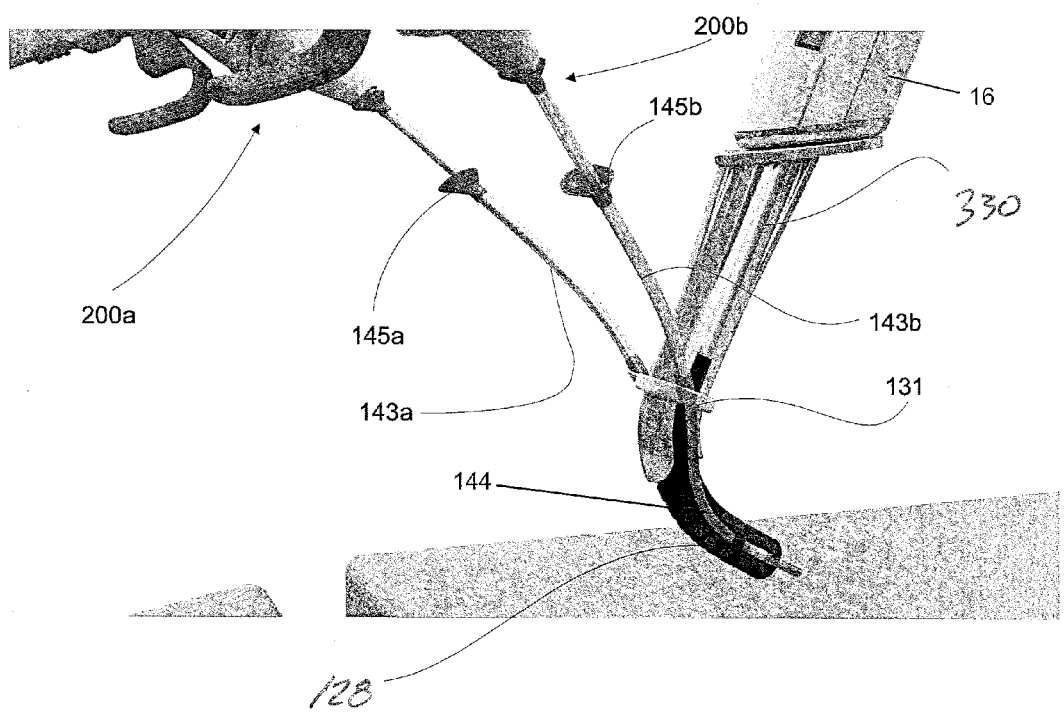
FIG. 23 illustrates a side perspective view of an embodiment of an introduction device having a pair of tool ports and attached to a feeding mechanism, in accordance with the present inventive concepts.

According to another embodiment, FIGS. 22 and 23 illustrate a rigid tube 143 for guiding a filament 202*a* to a tool side port 128 located on a distal portion of articulated probe 10. A flexible tube 144 may be disposed inside the rigid tube 143. According to the embodiment shown in FIG. 23, the rigid tube 143*a*, 143*b* has a tool funnel 145*a*, 145*b*, configured to readily and atraumatically introduce tools into the rigid tube 143*a*, 143*b*.

Figure 25:
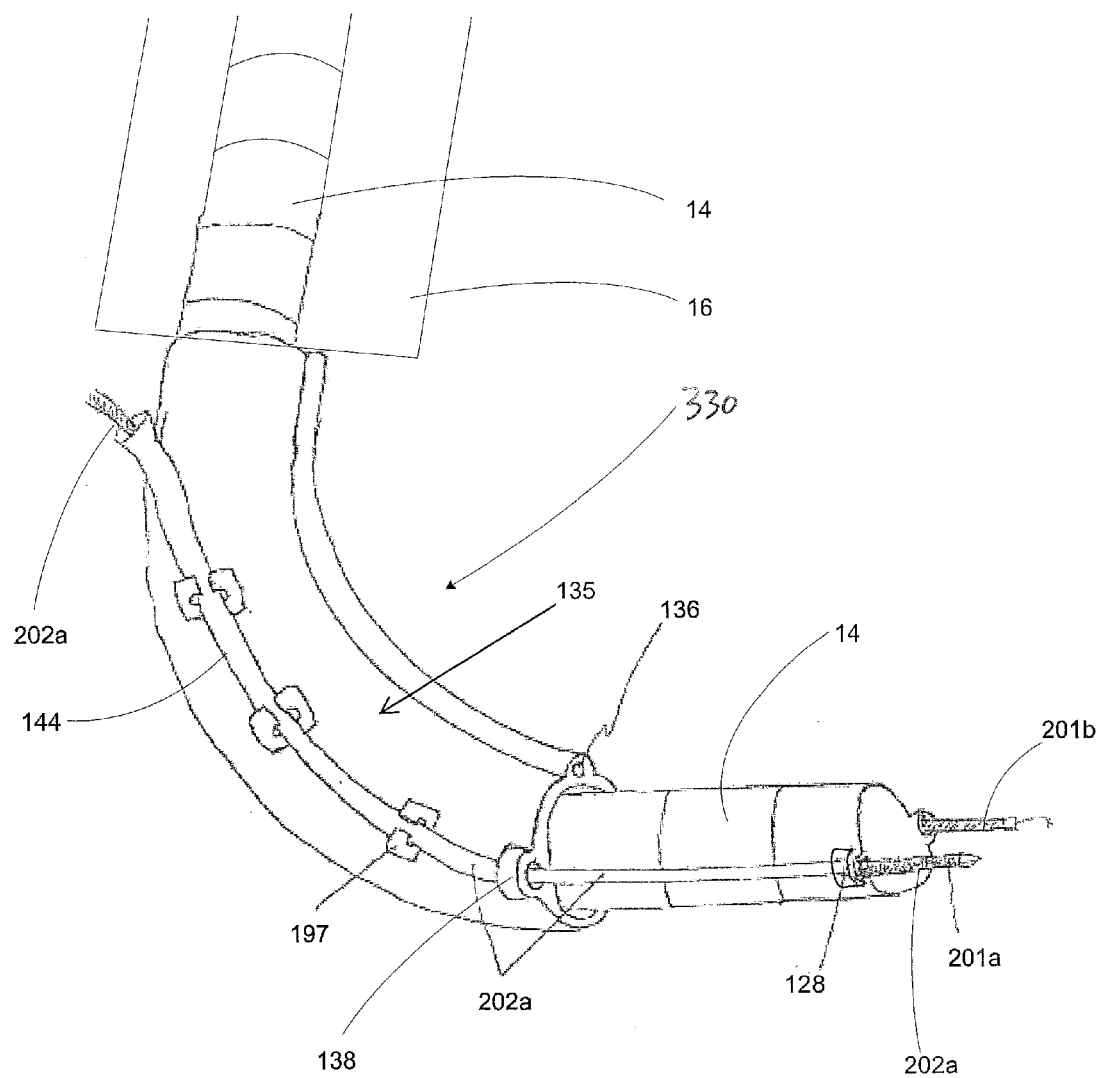
FIG. 25 illustrates a side perspective view of an embodiment of an introduction device, in accordance with the present inventive concepts.

FIG. 25 illustrates a flexible tube 144 attached to an outer surface of introduction device 330 and extending along a longitudinal axis of the introduction device 330. The flexible tube 144 is configured to guide or otherwise provide a support for filament 202*a* so that it can be guided into a tool side port 128 located on an outer surface of the articulated probe 10. The flexible tube 144 can be secured, for example snap-fit, to the outer surface of introduction device 330 using "c"-shaped supports 197 located on the outer surface of introduction device 330. Alternatively or additionally, supports 197 may be a closed-loop configuration such that flexible tube 144 can be slidingly received therethrough. In the snap-fit configuration, supports 197 are constructed and arranged to allow flexible tube 144 to be inserted through the application of a light pressing force relatively orthogonal to the outer surface of introduction device 330. Supports 197 may be further configured to allow flexible tube 144 to be detached through the application of a slight tension force in a direction away from the outer surface of introduction device 330. The flexible tube 144 is configured to guide a filament 202*a* along the body of the introduction device 330 and through a side channel 138 positioned on the outer surface of introduction device 330. The side channel 138 is configured to allow a filament 202*a*, such as a tool guide tube or a tool shaft, to pass through the side channel 138. The side channel 138 guides a filament 202*a* into a tool side channel 128 located on an outer link of the articulated probe 10. The filament 202*a* passes through both the side channel 138 located on the outer surface of introduction device 330 and the side channel 128 located on the probe 10. Thus, the introduction device 330 facilitates the introduction of tools passed through the side channel of the introducer 138 and side channel 128 of the articulated probe 10. Flexible tube 144 may be fixedly attached to side channel 138 (e.g. with adhesive or a mechanical fastener). Alternatively, flexible tube 144 may be allowed to slide through side channel 138.

Figure 27:
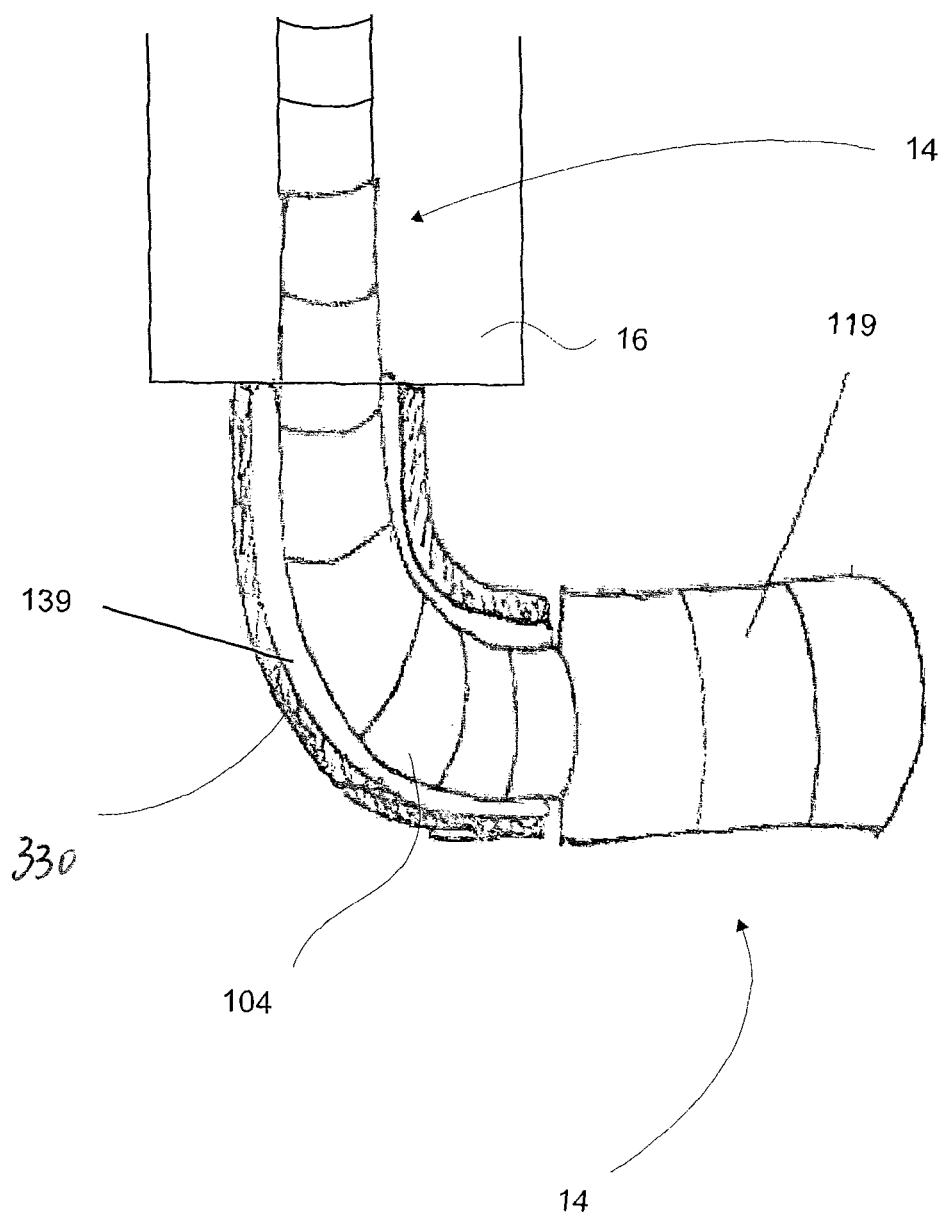
FIG. 27 illustrates a side perspective view of an embodiment of an introduction device, in accordance with the present inventive concepts.

FIG. 27 shows an introduction device 330 in which the probe 10 has several distal outer links 119 on its distal end that are larger than the outer links 104 on a more proximal portion of articulated probe 10. The outer links 119 may be larger in diameter than an opening of the introduction device 330 such that a proximal side of one of the distal outer links 119 can contact the distal end 118 of the introduction device 330. In this configuration, because the diameter of the outer links 119 is greater than the opening of the introduction device 330, the articulated probe 10 cannot fully retract into the introduction device 330. The smaller outer links 104 may be constructed and arranged to have a smaller radius of curvature than that of the larger outer links 119, for example in a case where the introduction device 330 has a smaller radius of curvature than that of the larger outer links 119. The larger outer links 119 can be advanced forward of introduction device 330, or simply steered. Larger outer links 119 can provide numerous advantages including improved stability when one or more forces are applied to the distal end of the outer sleeve 14.

Figure 28:
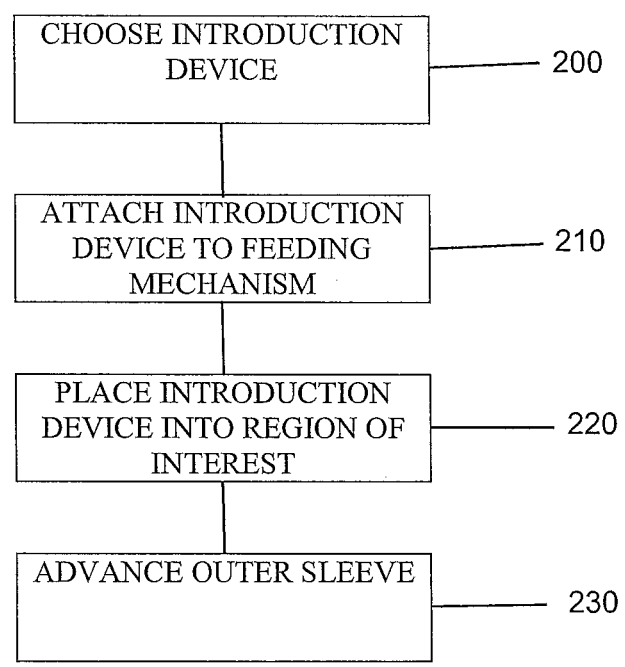
FIG. 28 illustrates a flow chart of a method of introducing an articulated probe, in accordance with the present inventive concepts.

Referring to FIG. 28, a method of introducing an articulated probe to a region of interest is illustrated. In STEP 200, an introduction device is chosen, such as an introduction device of the configuration described herein in connection with FIGS. 19 through 27. The introduction device can be chosen based on one or more parameters such as a parameter associated with the region to be accessed by the articulated probe. In a particular embodiment, the articulated probe is used on a patient and the introduction device is chosen based on patient anatomy, such as the esophageal geometry of the patient. Numerous forms and geometries of introduction devices may be made available to an operator such as a clinician, such as in a kit form for patient and/or application specific selection. In STEP 210, the introduction device 330 is attached to a feeding mechanism 16. Specifically, the proximal end 117 of the introduction device 330 is attached to the feeding mechanism 16. According to one embodiment shown in FIGS. 20 and 21, the introduction device 330 has an attachment surface 113. The attachment surface 113 can be permanently attached or integral to the feeding mechanism 16 or can be removably attached to the feeding mechanism 16. The feeding mechanism 16 can be any feeding mechanism known in the art for feeding an articulated probe 10. Preferably, the feeding mechanism 16 is the feeding mechanism shown in FIGS. 5A and 5B and described above, and used to independently cause both an inner core 12 and outer sleeve 14 of probe 10 to transition from rigid to flexible states; as well as independently advance and retract the inner core 12 and outer sleeve 14. The articulated probe 10 can be fed and pre-loaded from the feeding mechanism 16 into the introduction device 330, such as when both an inner core 12 and outer sleeve 14 of probe 10 are in a flexible state.

In STEP 220, a distal portion of introduction device 330 is placed into a region of interest such as a location internal to a patient. In one method, outer sleeve 14 may be advanced into introduction device 330 (e.g. until the distal end of outer sleeve 14 is proximate the distal end of introduction device 330), prior to placing introduction device 330 into the patient. Subsequently, both the introduction device 330 and outer sleeve 14 are advanced to the region of interest simultaneously. In a different method, outer sleeve 14 is advanced into and/or through introduction device 330 after the distal end 118 of introduction device 330 has been placed into the patient. Outer sleeve 14 may be advanced through introduction device 330 at an accelerated rate, such as a rate faster than is used during surgical or other high-precision manipulations.

The accelerated rate may be achieved by increasing the speed of cable tensioning (inner core and outer sleeve transitioning from flexible to rigid states) and/or cart movement (advancement and retraction of the inner core and outer sleeve) of probe 10, as has been described in detail herein. Alternatively or additionally, outer sleeve 14 may be advanced through introduction device 330 and/or with probe device 10 in a flexible state (e.g. outer sleeve in a flexible state or inner core and outer sleeve in flexible states). These accelerated advancements of probe 10 through introduction device 330 simplify use of probe 10, and greatly reduce procedure time.

In STEP 230, outer sleeve 14 is advanced into the patient, in a direction that is away from the distal end of introduction device 330, such as been described in detail hereabove. When the region of interest is a lumen, the introduction device 330 may work in conjunction with a retractor, such as a mouth retractor. The size and shape of the introduction device 330 may vary based on the region of interest. In the case of a body lumen region of interest, the size and shape of the introduction device 330 may vary based on the anatomy, size, and shape of the patient or the body lumen of the patient.

In an alternative embodiment, introduction device 330 may be inserted into a patient or other region of interest prior to attachment to the feeder mechanism 16. Subsequent to insertion, introduction device 330 may be attached to the feeder mechanism 16 and distal end of outer sleeve 14 advanced through introduction device 330 and into the region of interest.

While the preferred embodiments of the devices and methods have been described in reference to the environment in which they were developed, they are merely illustrative of the principles of the inventive concepts. Modification or combinations of the above-described assemblies, other embodiments, configurations, and methods for carrying out the invention, and variations of aspects of the inventive concepts that are obvious to those of skill in the art are intended to be within the scope of the claims. In addition, where this application has listed the steps of a method or procedure in a specific order, it may be possible, or even expedient in certain circumstances, to change the order in which some steps are performed, and it is intended that the particular steps of the method or procedure claim set forth here below not be construed as being order-specific unless such order specificity is expressly stated in the claim.

We claim:

1. An introduction assembly for an articulated probe, comprising:
    a feeding mechanism having at least one actuator for directly controlling at least one of a shape or articulation of the articulated probe; and
    an introduction device having a proximal end exclusively at and extending from the feeding mechanism, wherein the introduction device has a rigid unitary structure from the proximal end extending from the feeding mechanism to an output end, and is configured to receive the articulated probe and provide a supporting force to the articulated probe, wherein the articulated probe extends from the feeding mechanism to the output end of the introduction device, wherein the feeding mechanism controls a movement of the articulated probe relative to the introduction device, wherein the rigid unitary structure of the introduction device includes a lumen that is curved and smooth, wherein the articulated probe comprises a plurality of proximal links a plurality of distal links, and at least one distal outer link, wherein the at least one distal outer link has a width that is greater than a width of the lumen of the introduction device, wherein the feeding mechanism drives the plurality of proximal links and the plurality of distal links of the articulated probe through the curved smooth lumen of the rigid unitary structure of the introduction device, and wherein the width of the at least one distal outer link permits the at least one distal outer link to contact a distal end of the introduction device and further prevents the at least one distal outer link from retracting into the curved smooth lumen of the rigid unitary structure of the introduction device in response to the feeding mechanism driving the plurality of proximal links and the plurality of distal links of the articulated probe through the curved smooth lumen of the rigid unitary structure of the introduction device.

2. The introduction assembly of claim 1, wherein the introduction device is further configured to guide the articulated probe into a region of interest.

3. The introduction assembly of claim 2, wherein the region of interest is selected from the group consisting of: the esophagus; the gastrointestinal tract; the pericardial space; the peritoneal space; and combinations thereof.

4. The introduction assembly of claim 1, wherein the introduction device is connected to the feeding mechanism.

5. The introduction assembly of claim 4, wherein the introduction device is configured to be disconnected from the feeding mechanism.

6. The introduction assembly of claim 1, wherein the introduction device further comprises:
    a support member configured to support the articulated probe;
    an entrance positioned at the proximal end of the support member configured to guide the articulated probe into proximity with the support member; and
    an exit positioned at a distal end of the support member configured to guide the articulated probe from the support member into a region of interest.

7. The introduction assembly of claim 1, further comprising a tool shaft guide.

8. The introduction assembly of claim 7, wherein the tool shaft guide is configured to perform one or more of the following functions:
 slidingly receive a shaft of a tool; guide the shaft of a tool; provide a supporting force for a tool; and combinations thereof.

9. The introduction assembly of claim 7, further comprising a collar attaching the tool shaft guide to the introduction device.

10. The introduction assembly of claim 7, wherein the tool shaft guide is rotatably attached to the introduction device.

11. The introduction assembly of claim 10, wherein the tool shaft guide is rotatably attached to the introduction device with one degree of freedom.

12. The introduction assembly of claim 10, wherein the tool shaft guide is rotatably attached to the introduction device with multiple degrees of freedom.

13. The introduction assembly of claim 7, further comprising a second tool shaft guide.

14. The introduction assembly of claim 13, wherein the first tool shaft guide comprises a first geometry and the second tool shaft guide comprises a second geometry different than the first geometry.

15. The introduction assembly of claim 7, wherein the tool shaft guide comprises multiple coaxial tubes.

16. The introduction assembly of claim 15, wherein the tool shaft guide comprises a first tube comprising a first rigidity and a second tube comprising a second rigidity different than the first rigidity.

17. The introduction assembly of claim 16, wherein the first tube slidingly receives the second tube.

18. The introduction assembly of claim 17, wherein the first tube rigidity is greater than the second tube rigidity.

19. The introduction assembly of claim 7, wherein the tool shaft guide comprises a proximal end and a tapered opening positioned on the proximal end.

20. The introduction assembly of claim 7, wherein the tool shaft guide comprises a first portion and a second portion.

21. The introduction assembly of claim 20, wherein the tool shaft guide further comprises a joint connecting the first portion and the second portion.

22. The introduction assembly of claim 21, wherein the joint is selected from the group consisting of: a spherical joint; a hinged joint; and combinations thereof.

23. The introduction assembly of claim 7, wherein the tool shaft guide comprises a bend portion constructed and arranged to allow an operator to modify the geometry of the tool shaft guide.

24. The introduction assembly of claim 23, wherein the bend portion comprises a plastically deformable material.

25. The introduction assembly of claim 1, wherein the plurality of proximal links and plurality of distal links are at least one of inner links or outer links.

26. The introduction assembly of claim 1, wherein at least one of the plurality of proximal links comprises a first diameter, and at least one of the plurality of distal links comprises a second diameter, wherein the first diameter is less than the second diameter.

27. The introduction assembly of claim 26, wherein the plurality of distal links are constructed and arranged to remain external to the introduction device.

28. The introduction assembly of claim 26, wherein the introduction device comprises a distal end, and wherein one or more of the plurality of proximal links are constructed and arranged to pass through the introduction device distal end.

\* \* \* \* \*

UNITED STATES PATENT AND TRADEMARK OFFICE
CERTIFICATE OF CORRECTION

PATENT NO. : 9,649,163 B2  Page 1 of 1
APPLICATION NO. : 13/884407
DATED : May 16, 2017
INVENTOR(S) : Ian J. Darisse et al.

It is certified that error appears in the above-identified patent and that said Letters Patent is hereby corrected as shown below:

In the Claims

Claim 1, Column 24, Line 25, please insert a --,-- after "proximal links" and before "a plurality of".

Signed and Sealed this
Twelfth Day of December, 2017

Joseph Matal
*Performing the Functions and Duties of the*
*Under Secretary of Commerce for Intellectual Property and*
*Director of the United States Patent and Trademark Office*